US006290973B1

(12) United States Patent
Hawkins et al.

(10) Patent No.: US 6,290,973 B1
(45) Date of Patent: Sep. 18, 2001

(54) IMMUNOLOGICAL ADJUVANT COMPOUNDS, COMPOSITIONS, AND METHODS OF USE THEREOF

(75) Inventors: Lynn D. Hawkins, Concord; Sally T. Ishizaka, Weston; Michael Lewis, Andover; Pamela McGuiness, Metheun; Anneliese Nault, North Billerica; Jeffrey Rose, Chelmsford, all of MA (US); Daniel P. Rossignol, Mahwah, NJ (US)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/496,152

(22) Filed: Feb. 1, 2000

Related U.S. Application Data

(60) Provisional application No. 60/118,131, filed on Feb. 1, 1999.

(51) Int. Cl.[7] .................. A61K 45/00; A61K 39/295; A61K 39/00; C07C 261/00
(52) U.S. Cl. .................. 424/278.1; 424/201.1; 424/184.1; 558/159
(58) Field of Search ................. 424/278.1, 184.1, 424/201.1; 514/159

(56) References Cited

U.S. PATENT DOCUMENTS

| 5,904,925 | * | 5/1999 | Exner .................. 424/282.1 |
| 5,961,970 | * | 10/1999 | Lowell .................. 424/93.1 |
| 5,985,284 | * | 11/1999 | Lowell .................. 424/234.1 |
| 6,146,632 | * | 11/2000 | Momin et al. .................. 424/184.1 |
| 6,165,502 | * | 12/2000 | Oleske et al. .................. 424/450 |
| 6,180,111 | * | 1/2001 | Stein et al. .................. 424/249.1 |

FOREIGN PATENT DOCUMENTS

WO93/04672  3/1993  (WO).
WO95/11700  5/1994  (WO).

OTHER PUBLICATIONS

Inoue K., 1968, Chemical and Pharmaceutical Bulletin, vol. 16, No. 1, "Immunological Studies of Phospholipids. II. Syntheses of Cardiolipin and its Analogues", pp. 76–81.

Duralsky A.A. et al, Mar. 19, 1998, Tetrahedron Letters, NL, Elsevier Science Publishers, Amsterdam, vol. 39, No. 12, "Synthesis of Isotopically Labelled Cardiolipins"; pp. 1607–1610.

Jain M. K. et al, 1986, Biochim. Biophys. Acta (BBACAQ, 00063002); vol. 860 (3); "Effect of the Structure of Phospholipid on the Kinetics of Intravesicle Scooting of Phospholipase A2", pp. 462–474.

Inoue K et al, 1969, Chem. Phys. Lipids (CPLIA4); vol. 3, "Immunochemical Studies of Phospholipids, IV. Reactivities of Antiserum Against Natural Cardiolipin and Synthetic Cardiolipin Analogs–Containing Antigens". pp. 70–7.

Inoue K. et al, 1967, Chem. Phys. Lipids (CPLIA4), vol. 1 (4); "Immunochemical Studies of Phospholipids. I. Reactivity of Various Synthetic Cardiolipin Derivatives with Wassermann Antibody", the whole document.

Gregoriadies G et al, Aug. 1, 1996, Journal of Controlled Release, NL, Elsevier Science Publishers B.V. Amsterdam, vol. 41 No.1/02, "Liposomes As Immunological Adjuvants and Vaccine Carriers", pp. 49–56.

Vogel F.R., Jan. 1, 1995, Annals of the New York Academy of Sciences, "Immunologic Adjuvants for Modern Vaccine Formulations", pp. 153–160.

Gregoriadies G et al, Aug. 1, 1996, Journal of Controlled Release, NL, Elsevier Science Publishers B.V. Amsterdam, vol. 41 No.1/02, "Liposomes As Immunological Adjuvants and Vaccine Carriers", pp. 49–56.

Weissig V. et al, 1990, Wiss Z. Martin Luther Univ. Halle–Wittenberg, Math. Naturwiss. Reihe (WMHMAP), 01381504), vol. 39(6), "Functionalized Lipsomes with Immunological Adjuvant Effects", pp. 101–109.

P. Hoffmann, K.–H. Wiesmuller, J. Metzger, G. Jung, and W.G. Bessler. "Induction of Tumor Cytotoxicity in Murine Bone Morrow–Derived Macrophages by Two Synthetic Lipopeptide Analogues." *Biol. Chem. Hoppe–Seyler*, 1989, 370, 575–582.

K.–H. Wiesmuller, G. Jung, and G. Hess. "Novel low–molecular–weight synthetic vaccine against foot–and–mouth disease containINg a potent B–cell and macrophage activator." *Vaccine*, 1989, 7, 29–33.

K.–H. WiEsmuller, W.G. Bessler, and G. Jung. "Solid phase peptide synthesis of lipopeptide vaccines eliciting epitope–specific B–, T–helper and T–killer cell response."*Int. J. Peptide Protein Res.* 1992, 40, 255–260.

J.–P. Defoort, B. Nardelli, W. Huang, D.D. Ho, and J.P. Tam. "Macromolecular assemblage in the design of a synthetic AIDS vaccine." *Proc. Natl. Acad. Sci. USA*, 1992, 89, 3879–3883.

T. Toyokuni, B. Dean, S. Cai, D. Boivin, S. Hakomori, and A.K. Singhal. "Synthetic Vaccines: Synthesis of a Dimeric TN Antigen–Lipopeptide Conjugate That Elicits Immune Responses against Tn–Expressing Glycoproteins," *J. Am. Chem. Soc.* 1994, 116, 395–396.

(List continued on next page.)

*Primary Examiner*—Deborah C. Lambkin
(74) *Attorney, Agent, or Firm*—Hale and Dorr LLP

(57) ABSTRACT

The present invention is directed to novel compounds that function as immunological adjuvants when co-administered with antigens such as vaccines for bacterial and viral diseases, to novel adjuvant formulations which include at least one of the adjuvant compounds of the invention, to novel immunostimulatory compositions which comprise an antigen and at least one of the adjuvant compounds of the invention, and to methods for the immunization of an animal by co-administration of a compound of the invention with an antigen against which the animal is to be immunized.

13 Claims, 6 Drawing Sheets

OTHER PUBLICATIONS

F. Reichel, P.R. Ashton, and G.–J. Boons. "Synthetic carbohydrate–based vaccines: synthesis of an L–glycero–D–manno–heptose antigen–T–epitope–lipopeptide conjugate," *Chem. Commun.* 1997, 2087–2088.

H. Kamitakahara, T. Suzuki, N. Nishigori, Y. Suzuki, O. Kanie, and C.–H. Wong. "A Lysoganglioside/Poly–L–glutamic Acid Conjugate as a Picomolar Inhibitor of Influenza Hemagglutinin." *Angew. Chem. Int. Ed.* 1998, 37, 1524–1528.

W. Dullenkopf, G. Ritter, S.R. Fortunato, L.J. Old, and R.R. Schmidt, "Synthesis of a Structurally Defined Antigen–Immunostimulant Combination for use in Cancer Vaccines," *Chem. Eur. J.* 1999, 5, 2432–2438.

* cited by examiner

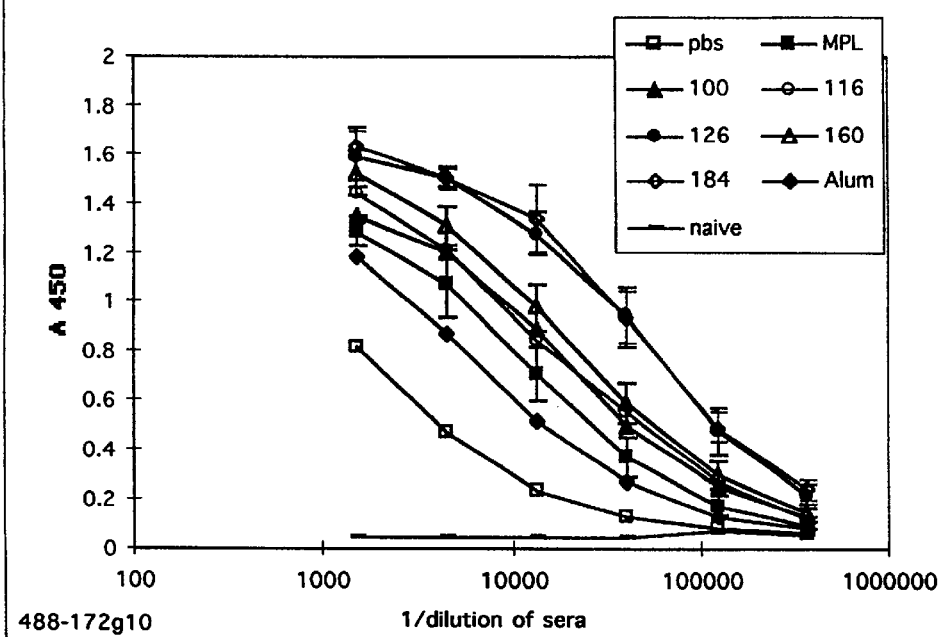

IMMUNOLOGICAL ADJUVANT COMPOUNDS, COMPOSITIONS, AND METHODS OF USE THEREOF

This application claims benefit of No. 60/118,131 Feb. 1, 1999.

BACKGROUND OF THE INVENTION

Vaccines have proven to be successful, highly acceptable methods for the prevention of infectious diseases. They are cost effective, and do not induce antibiotic resistance to the target pathogen or affect normal flora present in the host. In many cases, such as when inducing anti-viral immunity, vaccines can prevent a disease for which there are no viable curative or ameliorative treatments available.

Vaccines function by triggering the immune system to mount a response to an agent, or antigen, typically an infectious organism or a portion thereof that is introduced into the body in a non-infectious or non-pathogenic form. Once the immune system has been "primed" or sensitized to the organism, later exposure of the immune system to this organism as an infectious pathogen results in a rapid and robust immune response that destroys the pathogen before it can multiply and infect enough cells in the host organism to cause disease symptoms.

The agent, or antigen, used to prime the immune system can be the entire organism in a less infectious state, known as an attenuated organism, or in some cases, components of the organism such as carbohydrates, proteins or peptides representing various structural components of the organism.

In many cases, it is necessary to enhance the immune response to the antigens present in a vaccine in order to stimulate the immune system to a sufficient extent to make a vaccine effective, i.e., to confer immunity. Many protein and most peptide and carbohydrate antigens, administered alone, do not elicit a sufficient antibody response to confer immunity. Such antigens need to be presented to the immune system in such a way that they will be recognized as foreign and will elicit an immune response. To this end, additives (adjuvants) have been devised which immobilize antigens and stimulate the immune response.

The best known adjuvant, Freund's complete adjuvant, consists of a mixture of mycobacteria in an oil/water emulsion. Freund's adjuvant works in two ways: first, by enhancing cell and humoral-mediated immunity, and second, by blocking rapid dispersal of the antigen challenge (the "depot effect"). However, due to frequent toxic physiological and immunological reactions to this material, Freund's adjuvant cannot be used in humans.

Another molecule that has been shown to have immunostimulatory or adjuvant activity is endotoxin, also known as lipopolysaccharide (LPS). LPS stimulates the immune system by triggering an "innate" immune response—a response that has evolved to enable an organism to recognize endotoxin (and the invading bacteria of which it is a component) without the need for the organism to have been previously exposed. While LPS is too toxic to be a viable adjuvant, molecules that are structurally related to endotoxin, such as monophosphoryl lipid A ("MPL") are being tested as adjuvants in clinical trials. Currently, however, the only FDA-approved adjuvant for use in humans is aluminum salts (Alum) which are used to "depot" antigens by precipitation of the antigens. Alum also stimulates the immune response to antigens.

Thus, there is a recognized need in the art for compounds which can be co-administered with antigens in order to stimulate the immune system to generate a more robust antibody response to the antigen than would be seen if the antigen were injected alone or with Alum.

SUMMARY OF THE INVENTION

In one aspect, the present invention is directed to novel compounds that function as immunological adjuvants when co-administered with antigens such as vaccines for bacterial and viral diseases.

In a second aspect, the present invention is directed to novel adjuvant formulations which comprise at least one of the adjuvant compounds of the invention.

In a third aspect, the invention is directed to novel immunostimulatory compositions which comprise an antigen and at least one of the adjuvant compounds of the invention.

In another aspect, the present invention is directed to methods for the immunization of an animal by co-administration of a compound of the invention with an antigen against which the animal is to be immunized.

BRIEF DESCRIPTION OF THE DRAWINGS

FIG. 6 is a graph illustrating the results of serum titration analysis for determining amounts of antibody produced in response to tetanus toxoid in the absence and presence of compounds 100, 116, 126, 160 and 184 of the invention.

DETAILED DESCRIPTION OF THE PREFERRED EMBODIMENTS

Figure 1:
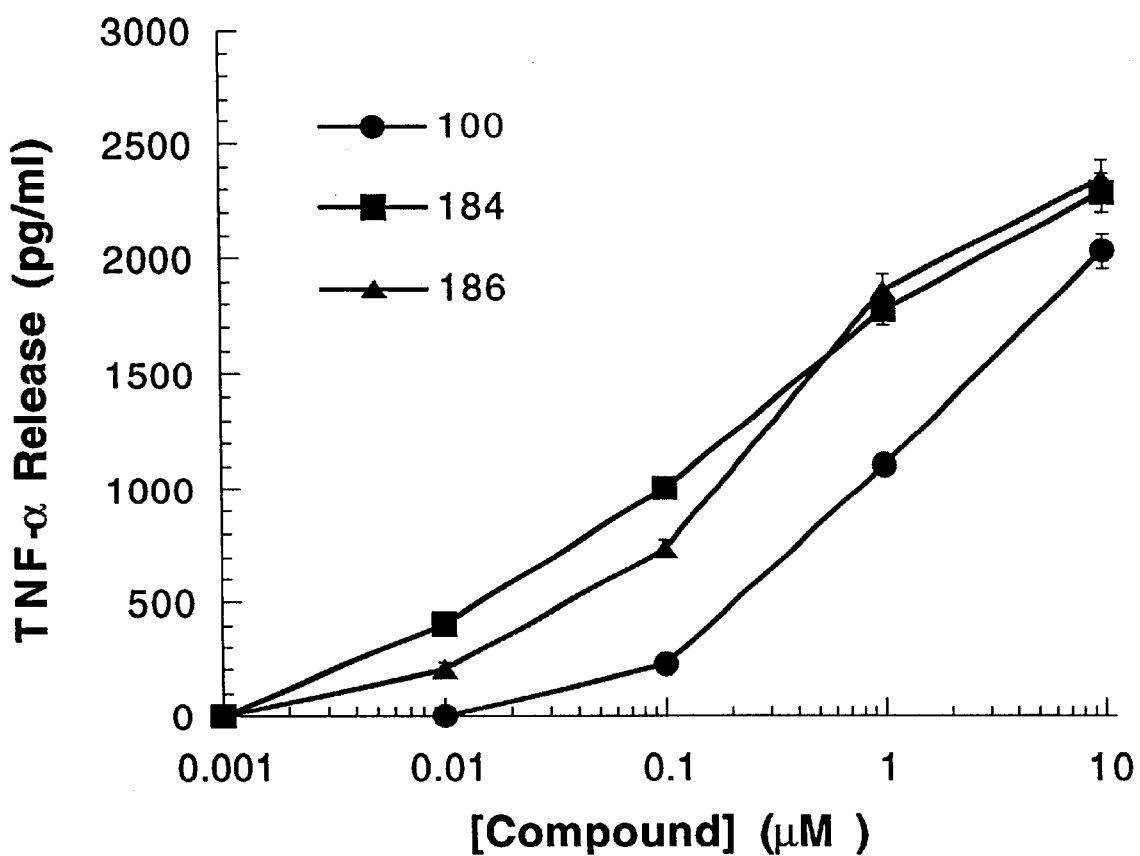
FIG. 1 is a graph that shows the results of an in vitro assay for induction of cytokine release by compounds 100, 184 or 186 of the invention.

The present invention is directed in part to novel compounds of formula 1

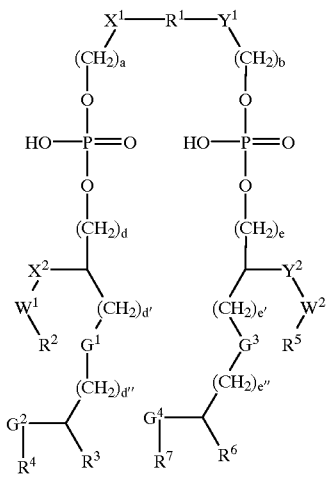

wherein:

$R^1$ is selected from the group consisting of (a) C(O);

(b) C(O)—$C_{1-14}$ alkyl-C(O), wherein said $C_{1-14}$ alkyl is optionally substituted with hydroxy, $C_{1-5}$ alkoxy, $C_{1-5}$ alkylenedioxy, $C_{1-5}$ alkylamino, or $C_{1-5}$-alkyl-aryl, wherein said aryl moiety of said $C_{1-5}$-alkyl-aryl is optionally substituted with $C_{1-5}$ alkoxy, $C_{1-5}$ alkylamino, $C_{1-5}$ alkoxy-amino, $C_{1-5}$ alkylamino-$C_{1-5}$ alkoxy, —O—$C_{1-5}$ alkylamino-$C_{1-5}$ alkoxy, —O—$C_{1-5}$ alkylamino-C(O)—$C_{1-5}$ alkyl C(O)OH, —O—$C_{1-5}$ alkylamino-C(O)—$C_{1-5}$ alkyl-C(O)-$C_{1-5}$ alkyl;

(c) $C_2$ to $C_{15}$ straight or branched chain alkyl optionally substituted with hydroxy or alkoxy; and (d) —C(O)—$C_{6-12}$ arylene-C(O)— wherein said arylene is optionally substituted with hydroxy, halogen, nitro or amino;

a and b are independently 0, 1, 2, 3 or 4;

d, d', d", e, e' and e" are independently an integer from 1 to 4;

$X^1$, $X^2$, $Y^1$ and $Y^2$ are independently selected from the group consisting of null, oxygen, NH and N(C(O)$C_{1-4}$ alkyl), and N($C_{1-4}$ alkyl)$_2$;

$W^1$ and $W^2$ are independently selected from the group consisting of carbonyl, methylene, sulfone and sulfoxide;

$R^2$ and $R^5$ are independently selected from the group consisting of:

(a) $C_2$ to $C_{20}$ straight chain or branched chain alkyl which is optionally substituted with oxo, hydroxy or alkoxy, (b) $C_2$ to $C_{20}$ straight chain or branched chain alkenyl or dialkenyl which is optionally substituted with oxo, hydroxy or alkoxy;

(c) $C_2$ to $C_{20}$ straight chain or branched chain alkoxy which is optionally substituted with oxo, hydroxy or alkoxy;

(d) —NH—$C_2$ to $C_{20}$ straight chain or branched chain alkyl, wherein said alkyl group is optionally substituted with oxo, hydroxy or alkoxy; and (e)

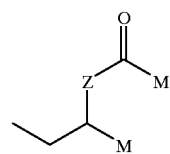

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;

$R^3$ and $R^6$ are independently selected from the group consisting of $C_2$ to $C_{20}$ straight chain or branched chain alkyl or alkenyl optionally substituted with oxo or fluoro;

$R^4$ and $R^7$ are independently selected from the group consisting of C(O)$C_2$ to $C_{20}$ straight chain or branched chain alkyl or alkenyl; $C_2$ to $C_{20}$ straight chain or branched chain alkyl; $C_2$ to $C_{20}$ straight chain or branched chain alkoxy; $C_2$ to $C_{20}$ straight chain or branched chain alkenyl; wherein said alkyl, alkenyl or alkoxy groups can be independently and optionally substituted with hydroxy, fluoro or $C_1$ to $C_5$ alkoxy;

$G^1$, $G^2$, $G^3$ and $G^4$ are independently selected from the group consisting of oxygen, methylene, amino, thiol, —NHC(O)—, and —N(C(O)$C_{1-4}$alkyl)—;

or $G^2R^4$ or $G^4R^7$ may together be a hydrogen atom or hydroxyl;

or a pharmaceutically acceptable salt thereof, with the proviso that the compounds are not

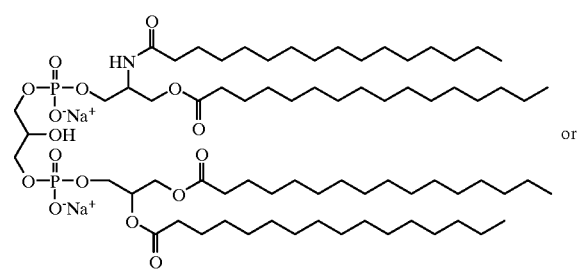

or

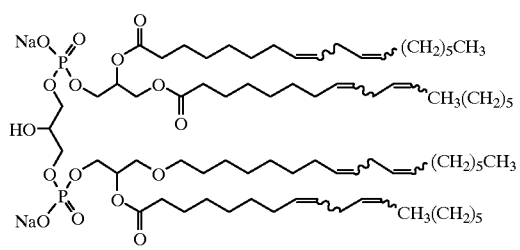

The present invention also encompasses immunological adjuvant formulations comprising a compound of formula 1

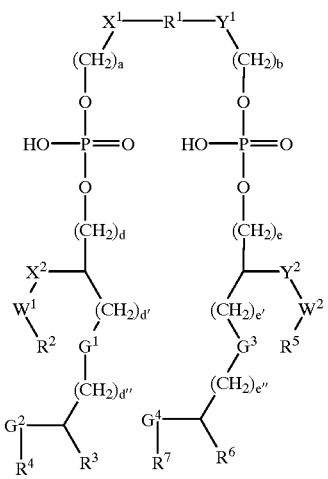

wherein:

$R^1$ is selected from the group consisting of (a) C(O);

(b) C(O)—$C_{1-14}$ alkyl-C(O), wherein said $C_{1-4}$ alkyl is optionally substituted with hydroxy, $C_{1-5}$ alkoxy, $C_{1-5}$ alkylenedioxy, $C_{1-5}$ alkylamino, or $C_{1-5}$-alkyl-aryl, wherein said aryl moiety of said $C_{1-5}$-alkyl-aryl is optionally substituted with $C_{1-5}$ alkoxy, $C_{1-5}$ alkylamino, $C_{1-5}$ alkoxy-amino, $C_{1-5}$ alkylamino-$C_{1-5}$ alkoxy, —O—$C_{1-5}$ alkylamino-$C_{1-5}$ alkoxy, —O—$C_{1-5}$ alkylamino-C(O)—$C_{1-5}$ alkyl C(O)OH, —O—$C_{1-5}$ alkylamino-C(O)—$C_{1-5}$ alkyl-C(O)—$C_{1-5}$ alkyl;

(c) $C_2$ to $C_{15}$ straight or branched chain alkyl optionally substituted with hydroxy or alkoxy; and (d) —C(O)—$C_{6-12}$ arylene-C(O)— wherein said arylene is optionally substituted with hydroxy, halogen, nitro or amino;

a and b are independently 0, 1, 2, 3 or 4;

d, d', d", e, e' and e" are independently an integer from 1 to 4;

$X^1$, $X^2$, $Y^1$ and $Y^2$ are independently selected from the group consisting of null, oxygen, NH and N(C(O)$C_{1-4}$ alkyl), and N($C_{1-4}$ alkyl)$_2$;

$W^1$ and $W^2$ are independently selected from the group consisting of carbonyl, methylene, sulfone and sulfoxide;

$R^2$ and $R^5$ are independently selected from the group consisting of:

(c) $C_2$ to $C_{20}$ straight chain or branched chain alkyl which is optionally substituted with oxo, hydroxy or alkoxy, (d) $C_2$ to $C_{20}$ straight chain or branched chain alkenyl or dialkenyl which is optionally substituted with oxo, hydroxy or alkoxy;

(c) $C_2$ to $C_{20}$ straight chain or branched chain alkoxy which is optionally substituted with oxo, hydroxy or alkoxy;

(d) —NH—$C_2$ to $C_{20}$ straight chain or branched chain alkyl, wherein said alkyl group is optionally substituted with oxo or alkoxy; and (e)

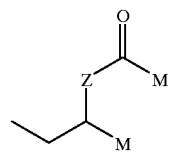

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;

$R^3$ and $R^6$ are independently selected from the group consisting of $C_2$ to $C_{20}$ straight chain or branched chain alkyl or alkenyl optionally substituted with oxo or fluoro;

$R^4$ and $R^7$ are independently selected from the group consisting of C(O)$C_2$ to $C_{20}$ straight chain or branched chain alkyl or alkenyl; $C_2$ to $C_{20}$ straight chain or branched chain alkyl; $C_2$ to $C_{20}$ straight chain or branched chain alkoxy; $C_2$ to $C_{20}$ straight chain or branched chain alkenyl; wherein said alkyl, alkenyl or alkoxy groups can be independently and optionally substituted with hydroxy, fluoro or $C_1$ to $C_5$ alkoxy;

$G^1$, $G^2$, $G^3$ and $G^4$ are independently selected from the group consisting of oxygen, methylene, amino, thiol, —NHC(O)—, and —N(C(O)$C_{1-4}$ alkyl)—;

or $G^2R^4$ or $G^4R^7$ may together be a hydrogen atom or hydroxyl;

or a pharmaceutically acceptable salt thereof;

and at least one additional component.

In preferred compounds of the invention, one or more of the following is present: each of a and b is 2; each of $X^1$ and $Y^1$ is NH; $R^1$ is C(O) or C(O)—$C_{1-4}$ alkyl-C(O); each of d' and e' is 1; each of d" and e" is 1; X is O or NH, more preferably NH; and W is C(O); or each of d' and e' are 2.

In further preferred embodiments, R' is a C(O)$C_{1-4}$ alkyl-C(O), wherein said $C_{1-4}$ alkyl is substituted, for example with a $C_{1-5}$ alkoxy group;

In a most preferred embodiment, the invention is directed to compounds ER 803022, ER 803058, ER 803732, ER 804053, ER 804057, ER 804058, ER 804059, ER 80442, ER 804680 and ER 804764, and compositions containing these compounds.

The invention is also directed to novel immunostimulatory compositions which include an antigen and an immunological adjuvant formulation of the invention as disclosed above.

Also provided are methods for the immunization of an animal by co-administration of a compound of the invention or an adjuvant formulation of the invention with an antigen against which the animal is to be immunized.

Definitions

Carbonyl, as used herein, is a (C=O) moiety.

Dicarbonyl, as used herein, is a moiety with the structure (C=O)-alkyl-(C=O) or (C=O)-aryl-(C=O), which is bonded to a molecule through the carbon atoms of both of the terminal carbonyl moieties.

Oxo, as used herein, is a =O group.

Alkyl ester, as used herein, is a moiety with the structure O—(C=O)-alkyl, which is bonded to a molecule through the non-double bonded oxygen of the ester group.

Alkenyl ester, as used herein, is a moiety with the structure O—(C=O)-carbon chain, where the carbon chain contains a carbon-to-carbon double bond, which is bonded to a molecule through the non-double bonded oxygen of the ester group.

The term "alkylene" means a bivalent straight chain or branched alkyl hydrocarbon group.

The term "alkenylene" means a bivalent straight chain or branched hydrocarbon group having a single carbon to carbon double bond.

The term "dialkenylene" means a bivalent unsaturated straight chain or branched chain hydrocarbon group having two carbon to carbon double bonds.

The term "arylene" refers to a bivalent aromatic group.

The abbreviation "Boc" as used herein means t-butyloxycarbonyl.

As used herein with reference to compounds and compositions of the invention, the term "type 1" refers to those compounds of the invention corresponding to formula I above where the values of a and b are the same; the values of d and e are the same; the values of d' and e' are the same; the values of d" and e" are the same; $X^1$ and $Y^1$ are the same; $X^2$ and $Y^2$ are the same; $W^1$ and $W^2$ are the same; $R^2$ and $R^1$ are the same; $G^1$ and $G^3$ are the same; $R^3$ and $R^6$ are the same; $G^2$ and $G^4$ are the same; and $R^4$ and $R^7$ are the same. "Type 2", as used herein, refers to compounds or compositions corresponding to formula I where any one or more of the following applies: the values of a and b are different, the values of d and e are different, the values of d' and e' are different; the values of d" and e" are the same; $X^1$ and $Y^1$ are different; $X^2$ and $Y^2$ are different; $W^1$ and $W^2$ are different; $R^2$ and R5 are different; $G^1$ and $G^2$ are different; $R^3$ and $R^6$ are different; or $R^4$ and $R^7$ are different.

All patents, patent applications, and publications referred to herein are incorporated by reference in their entirety. In case of a conflict in terminology, the present specification is controlling.

General Synthetic Methods

1. Synthesis of Diamide Compounds

In general, a 2-amino-1,3-dihydroxypropane or (±) serinol is transformed into the 2-azido compound by reaction with trifluoromethanesulfonyl azide followed by protection as the per-acetate for easy manipulation. The resulting compound is deacetylated, followed by reaction with an appropriately activated primary alcohol of a diol moiety. The primary alcohol moiety of the product of this reaction is then protected, e.g., by using TBDPSCl, followed by reaction with phosgene and then allyl alcohol, to yield a fully protected diol. The protected diol is then treated to cleave the protecting group from the primary alcohol. The unprotected alcohol is reacted with a properly functionalized phosphorylating reagent with formula (11) as indicated in the Examples, to form a phosphate ester compound. The azido moiety of the product is reduced, and then reacted with an activated acyl acid to form an amide. The protected terminal amine on the functionalized phosphate is deprotected, and subsequently reacted with a phosgene or a dicarboxylic acid in the presence of a dehydrating agent, such as EDC. The phosphate groups of the resulting compound are then deprotected, yielding a racemic amide.

2. Synthesis of Chiral Diamide Compounds of Type 1

In general, a chiral amino acid ester with the desired structure is protected with a benzimidate ester. The protected compound is reacted with a reducing agent, e.g., DIBAL or the like, to reduce the acid moiety of the amino acid to an alcohol. The resulting alcohol compound is reacted with an appropriately activated primary alcohol of a diol moiety, followed by cleavage of the benzimidate protecting group, yielding an amino-diol. The diol is then reacted with an appropriate acid chloride to yield a diol-amide.

The diol-amide is then reacted with a properly functionalized phosphorylating reagent at the free primary hydroxyl group. The resulting compound is esterified at the secondary alcohol group with an appropriate acyl moiety. The N-BOC group is then cleaved from the amino group introduced by phosphorylating reagent (11), yielding a phosphate ester compound with a free primary amine. This product is then reacted with phosgene or a dicarboxylic acid in the presence of a dehydrating agent, to yield a diamide product. The protected phosphate groups of the diamide product are then deprotected, typically with palladium (0) and phenylsilane.

3. Synthesis of Chiral Diamide Compounds of Type 2

Chiral diamide compounds of Type 2 are synthesized essentially as described for chiral diamide compounds of Type 1, up to the point just after cleavage of the protecting group from the primary amine group of the phosphate ester compound. At this point, a dicarboxylic acid which has one of the acid moieties protected is reacted with the primary amine group, to yield a monoamide. The protecting group on the other carboxylic acid is then cleaved, providing a free carboxylic acid which can then be reacted with a primary amine from an alternative, appropriately substituted phosphate system, in the presence of a dehydrating agent to yield a diamide of type 2, which can then be treated to deprotect the phosphate group or groups to yield a desired compound of the invention.

In the special case of chiral urea compounds of type 2 of the invention, the primary amino group of the N-BOC amino group of the phosphate ester is deprotected and then reacted with trichloromethyl chloroformate or the like, in order to form an isocyanate compound. The isocyanate is then reacted with a primary amine from an alternative, appropriately substituted phosphate system to yield a urea product of type 2. This product can then be treated to deprotect the phosphate group or groups.

4. Glycerol Diamide Analogs

These compounds of the invention have an ester moiety attached to the carbon which is beta to the phosphate group, instead of an amide moiety.

In general, these compounds are prepared by the etherification of a protected chiral glycerol with an activated primary alcohol of a diol moiety, followed by esterification of the secondary alcohol moiety and subsequent deprotection of the glycerol moiety, to yield a new diol. The primary hydroxyl group of the diol is then protected, and the secondary hydroxyl group is condensed with an acyl moiety to yield a diester. The primary hydroxyl is deprotected, followed by esterification with a phosphorylating agent, of which compound (11), below is exemplary. Following deprotection of the amine group introduced by the phosphorylating agent, the product is reacted with phosgene or a dicarboxylic acid using a dehydrating agent such as EDC. Subsequent deprotection of the phosphate groups yield compounds of the invention.

In the synthesis described generally above, the substituent at $R^1$ of the compounds of the invention can easily be varied by utilizing different dicarboxylic acid compounds. Such acids can be coupled to the amine group of the phosphate ester intermediate of the reaction scheme outlined above, either using a dehydrating agent such as EDC, or by activating the dicarboxylic acid by synthesizing, e.g., the corresponding diacid chloride.

The substituents represented by variables $R^2$ and $R^5$ in formula I above can easily be varied by utilizing an appropriate activated acid or acid chloride in the amidation or esterification reaction of the heteroatom represented by X or Y in formula I.

The substituents represented by variables $R^3$ and $R^6$ of formula I can be varied by using an intermediate containing the desired number of carbon atoms which also contains an activated carbon functionality, e.g., a halogen or sulfonate ($OSO_2CH_3$, $OSO_2CF_3$, $OSO_2CH_2C_6H_4$—p—$CH_3$) which can be reacted with the azido diol, amino alcohol, or glycerol starting materials.

The substituents represented by variables $R^4$ and $R^7$ in formula I above can be varied by using an appropriate activated acid or acid chloride in the esterification of the secondary hydroxyl group used in the reaction schemes outlined above.

The values of a and b in compounds of formula I can be varied by using the appropriate N-BOC-protected amino alcohol when synthesizing the phosphorylating reagent, exemplified by compound (11) below. The values of variables d and e in compounds of formula I can be modified by using the appropriate 2-aminodiol or 2-hydroxydiol starting materials.

Adjuvant and Vaccine Formulation and Administration

The present invention is also directed to adjuvant formulations comprising adjuvant compounds of the invention, as well as vaccine and other immunostimulatory formulations which comprise the adjuvant compounds of the invention. Methods for the stimulation of an immune response to a particular antigen are also within the scope of the invention.

The host animals to which the adjuvant and adjuvant-containing vaccine formulations of the present invention are usefully administered include human as well as non-human mammals, fish, reptiles, etc.

Typically, an antigen is employed in mixture with the adjuvant compounds of the invention. In other formulations of the adjuvant of the present invention, it may be useful in some applications to employ an antigen covalently linked to an amino, carboxyl, hydroxyl and/or phosphate moiety of the adjuvant compounds of the invention. The specific formulation of therapeutically effective compositions of the present invention may thus be carried out in any suitable manner which will render the adjuvant bioavailable, safe and effective in the subject to whom the formulation is administered.

The invention broadly contemplates therapeutic adjuvant formulations, which may for example comprise (i) at least one therapeutically effective antigen or vaccine; and (ii) at least one adjuvant compound according to the invention.

Such therapeutic composition may for example comprise at least one antigenic agent selected from the group consisting of:

(A) live, heat killed, or chemically attenuated viruses, bacteria, mycoplasmas, fungi, and protozoa;

(B) fragments, extracts, subunits, metabolites and recombinant constructs of (A);

(C) fragments, subunits, metabolites and recombinant constructs of mammalian proteins and glycoproteins;

(D) tumor-specific antigens; and (E) nucleic acid vaccines.

The therapeutic composition may therefore utilize any suitable antigen or vaccine component in combination with an adjuvant compound of the invention, e.g., an antigenic agent selected from the group consisting of antigens from pathogenic and non-pathogenic organisms, viruses, and fungi, in combination with an adjuvant compound of the invention.

As a further example, such therapeutic compositions may suitably comprise proteins, peptides, antigens and vaccines which are pharmacologically active for disease states and conditions such as smallpox, yellow fever, distemper, cholera, fowl pox, scarlet fever, diphtheria, tetanus, whooping cough, influenza, rabies, mumps, measles, foot and mouth disease, and poliomyelitis. In the resulting vaccine formulation, comprising (i) an antigen, and (ii) at least one adjuvant compound of the invention the antigen and adjuvant compound are each present in an amount effective to elicit an immune response when the formulation is administered to a host animal, embryo, or ovum vaccinated therewith.

In further embodiments, the compounds of the invention may be covalently bonded to vaccine antigens, for example through an amino, carbonyl, hydroxyl or phosphate moiety. The compounds of the invention may be bonde, Methods of linking the adjuvant compositions of the invention to vaccine antigens are understood by persons of ordinary skill in the art in view of this disclosure. The adjuvant compositions may be linked to vaccines by any of the methods described in P. Hoffman et al., *Biol. Chem. Hoppe-Sayler,* 1989, 370:575–582; K. -H. Wiesmuller et al., *Vaccine,* 1989, 7:29–33; K. -H Wiesmuller et al., *Int. J. Peptide Protein Res.,* 1992, 40:255–260; J. -P. Defourt et al., *Proc. Natl. Acad. Sci.* 1992, 89:3879–3883; T. Tohokuni et al., *J. Am. Chem. Soc.,* 1994, 116:395–396; F. Reichel, Chem. Commun., 1997, 2087–2088; H. Kamitakahara, *Angew. Chem. Int. Ed.* 1998, 37:1524–1528; W. Dullenkopf et al., *Chem. Eur. J.,* 1999, 5:2432–2438; all of which are hereby incorporated by reference.

The resulting vaccine formulations, including (i) an antigen, and (ii) an adjuvant compound, are usefully employed to induce an immunological response in an animal, by administering to such animal the vaccine formulation, in an amount sufficient to produce an antibody response in such animal.

The modes of administration may comprise the use of any suitable means and/or methods for delivering the adjuvant, adjuvant-containing vaccine, or adjuvant and/or antigen to one or more corporeal loci of the host animal where the adjuvant and associated antigens are immumostimulatively effective. Delivery modes may include, without limitation, parenteral administration methods, such as subcutaneous (SC) injection, transcutaneous, intranasal (IN), ophthalmic, transdermal, intramuscular (IM), intradermal (ID), intraperitoneal (IP), intravaginal, pulmonary, and rectal administration, as well as non-parenteral, e.g., oral, administration.

The dose rate and suitable dosage forms for the adjuvant and vaccine compositions of the present invention may be readily determined by those of ordinary skill in the art without undue experimentation, by use of conventional antibody titer determination techniques and conventional bioefficacy/biocompatibility protocols, and depending on the particular antigen or therapeutic agent employed with the adjuvant, the desired therapeutic effect, and the desired time span of bioactivity.

The adjuvant of the present invention may be usefully administered to the host animal with any other suitable pharmacologically or physiologically active agents, e.g., antigenic and/or other biologically active substances.

Formulations of the invention can include additional components such as saline, oil, squalene, oil-water dispersions, liposomes, and other adjuvants such as QS-21, muramyl peptides, Freunds's incomplete adjuvant, and the like.

SYNTHETIC EXAMPLES

All reaction products in the synthetic methods described below gave satisfactory NMR spectra and thin layer chromatography profiles on silica gel. All chromatography was performed on silica gel and the elution monitored by thin layer chromatography. All completed reactions were determined by thin layer chromatographic analysis. All reactions were run under nitrogen at room temperature unless otherwise specified. All reaction solvents were anhydrous unless otherwise noted. The typical work-up for the chemical reactions described below includes aqueous washings, drying over anhydrous sodium sulfate and removal of solvent under reduced pressure.

Example 1

Succinate-1

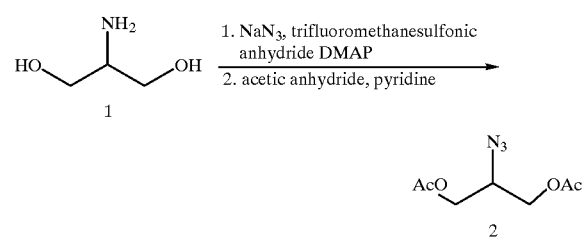

To a solution of sodium azide (107.67 g) in 250 mL of water was added 300 mL of methylene chloride. The mixture was cooled to 0° C. and trifluoromethanesulfonic anhydride (57 mL) was added dropwise at a 0.32 mL/minute rate. The mixture was stirred for an additional 6 hours at 0° C. and stored at −20° C. for 72 hours. The mixture was warmed to 10° C. followed by extraction with methylene chloride in a Teflon™ separatory funnel. The combined organic layers were dried (magnesium sulfate). The above suspension was slowly filtered into a stirred solution of (±)-2-amino-1,3-dihydroxypropane (1) (9.89 g) in methanol (200 mL) and 4-N,N-dimethylaminopyridine (DMAP, 54 g) at 10° C. The resultant reaction mixture was stirred for 17 hours at room temperature.

The solvent was removed under reduced pressure and the residue dissolved in pyridine (200 mL) and cooled to 0° C. Acetic anhydride (50 mL) was added dropwise and the mixture stirred for 20 hours at room temperature. Additional acetic anhydride (20 mL) was added and after 4 hours, the mixture was poured onto ice and worked up in the usual manner. Chromatography gave 16 g of diacetate (2) as an oil.

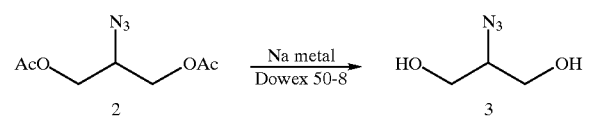

The diacetate (2) (16 g) was dissolved in methanol (150 mL) and sodium metal (2.0 g) was slowly added. The mixture was stirred for 90 minutes and Dowex™ 50-8 resin was added until the pH was less than or equal to 7. The mixture was filtered followed by concentration of the filtrate and chromatography to give 6.73 g of the diol (3).

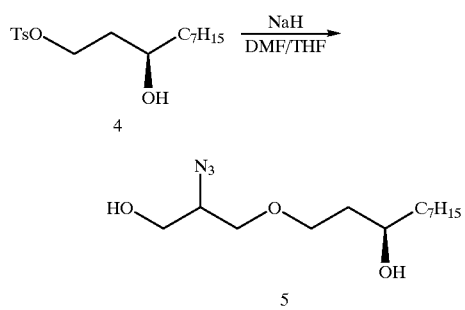

To a suspension of sodium hydride (1.24 g of a 60% oil dispersion washed three times with hexanes and dried under nitrogen) in dimethylformamide (DMF, 200 mL) was added dropwise the azido-diol (3) (6.73 g) in THF (100 mL), followed by the dropwise addition of 3-R-hydroxy-1-O-tosyl-1-decanol (4) (tosylate, 9.44 g) in THF (100 mL). The mixture was stirred for 16 hours, diluted with methanol (200 mL), stirred with Amberlite™ 125 H$^+$ or 25 minutes and concentrated to dryness. Chromatography gave 4.37 g of (5).

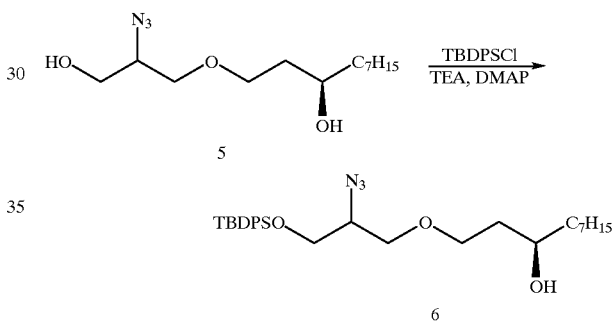

To a solution of the diol (5) (5.32 g) in methylene chloride (30 mL) was added triethylamine (TEA, 6 mL) and DMAP (trace), followed by t-butyldiphenylsilyl chloride (TBDPSCl, 5 mL) and the mixture was stirred overnight. The mixture was worked up as usual. Chromatography gave 3.6 g of secondary alcohol (6) as an oil.

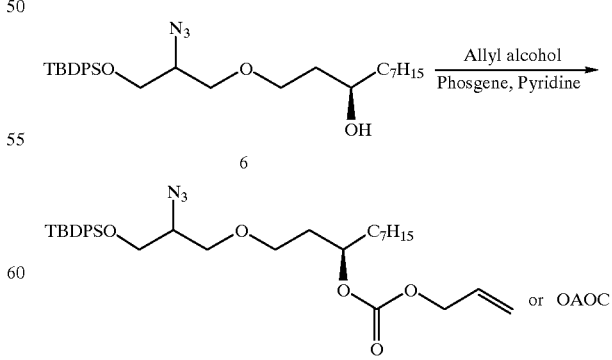

To a solution of the secondary alcohol (6) (2.95 g) in toluene (30 mL) was added pyridine (1.8 mL) followed by a slow addition of phosgene (4.5 mL of a 1.93 M solution in toluene) at 0° C. After stirring at 0° C. for 20 minutes, allyl alcohol (3.1 mL) was added dropwise. After an additional stirring for 60 minutes at room temperature, the reaction was worked up in the usual way. Chromatography gave 3.24 g of protected alcohol (7) as an oil.

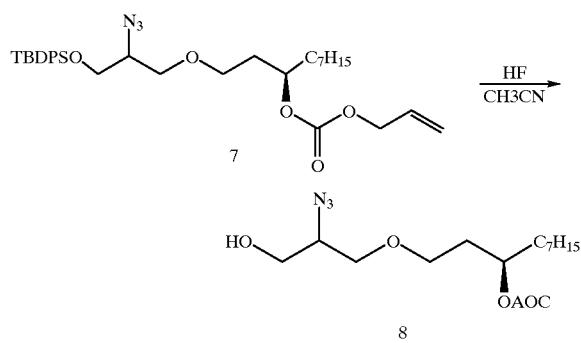

To a solution of protected alcohol (7) (1.29 g) in methylene chloride (3 mL) was added hydrofluoric acid (HF, 4 mL) in acetonitrile (12 mL). The mixture was stirred overnight and worked up in the usual way. Chromatography gave 150 mg of the alcohol (8) as an oil.

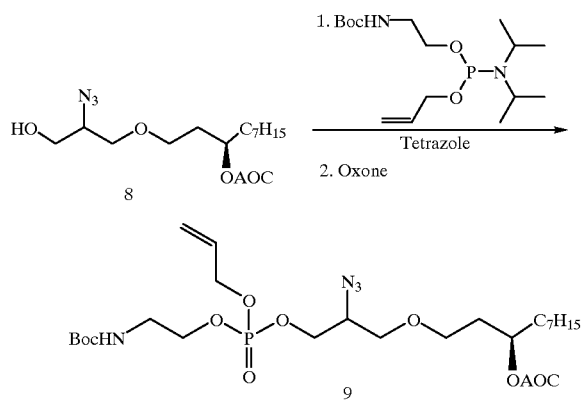

To a solution of alcohol (8) (150 mg) in methylene chloride (0.6 mL) was added tetrazole (74 mg) and the phosphorylating reagent (11) (175 mg). After 30 minutes, oxone (323 mg) in a cooled THF (0.5 mL)-water (0.5 mL) solution was added to the cooled reaction mixture. After 3 hours, the reaction was worked up in the usual way. Chromatography gave 242 mg of (9) as an oil.

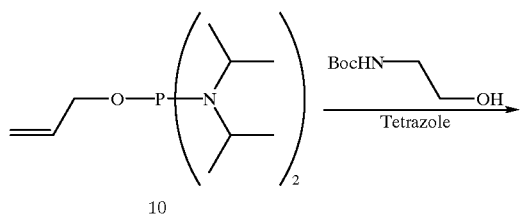

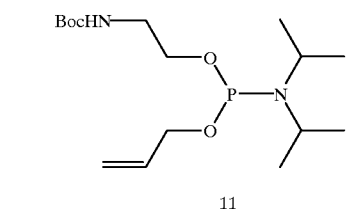

To make phosphorylating reagent 11, to a solution of distilled diisopropylamine (9.0 mL) in methylene chloride was added tetrazole (4.51 g) at room temperature followed by stirring for 1.5 hours. Allyl phosphorodiamidite (10) (20.5 mL) was added dropwise at a 6.5 mL/hour rate followed by stirring for an additional 3 hours. N-Boc-2-aminoethanol (10.36 g) in methylene chloride (50 mL) was added to the above reaction mixture dropwise at a 8.4 mL/hour rate followed by stirring for an additional 18 hours. The white suspension was filtered through Celite 545 with two 20 mL washings with methylene chloride. The filtrate was concentrated followed by the suspension and filtering of the residue with hexanes (200 mL). The resulting hexanes filtrate was concentrated to dry and azeotroped with 2, 10-mL portions of toluene to provide the crude product (11) (21.54 g) as an oil.

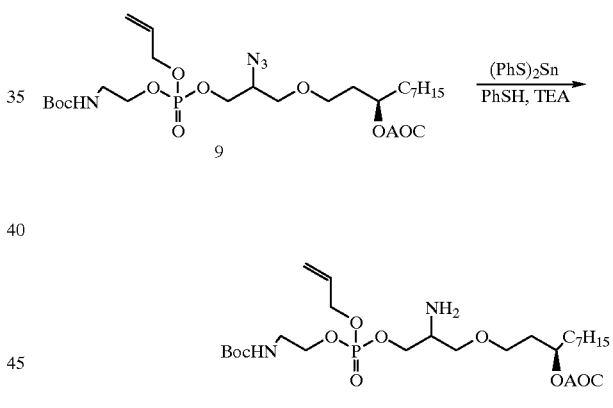

To a suspension of dithiophenol tin (1.3 g) in methylene chloride (7.8 mL) was added thiophenol (400 μL) followed by TEA (543 μL). The reaction mixture was stirred at room temperature for 15 minutes followed by stopping the stirring and allowing the residue to settle to the bottom of the flask. 1.0 mL of the above solution was added to a solution of the azide (9) (242 mg) in methylene chloride (0.5 mL) and allowed to stir for 30 minutes. Quenching with 0.1 N NaOH followed by the usual work-up afforded 193.1 mg of the amine (12) as an oil.

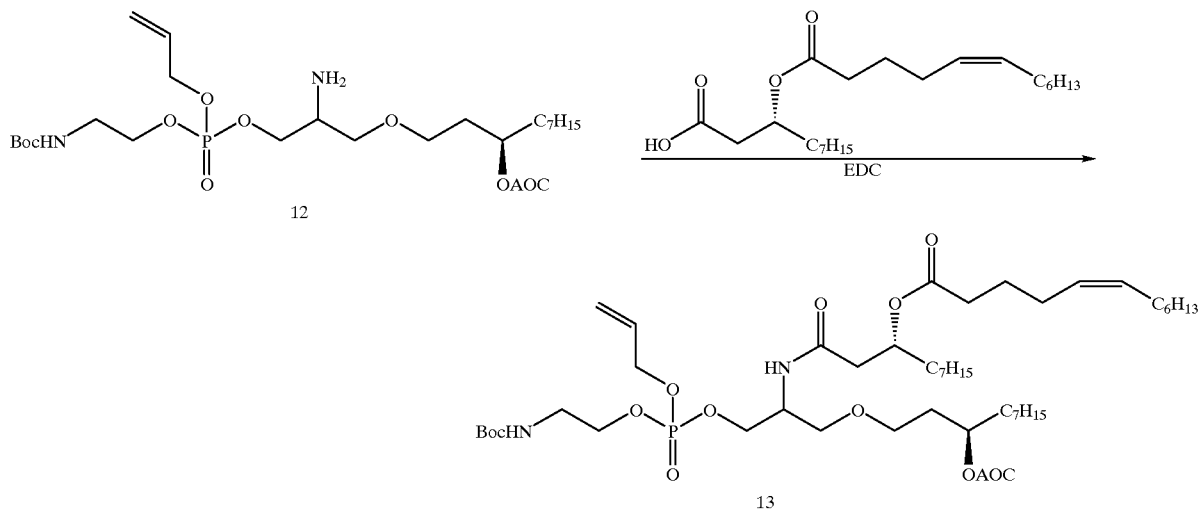

To a dried solution of the amine (12) (193 mg) and acyl acid (which can be made according to Christ et al., U.S. Pat. No. 5,530,113) (132 mg) in methylene chloride was added 1-(3-dimethylaminopropyl)-3-ethylcarbodiimide hydrochloride (EDC, 93 mg). After stirring at room temperature for 90 minutes the reaction was quenched and processed in the usual way to provide 232 mg of protected phosphate (13) as an oil.

To a solution of the protected phosphate (13) (232 mg) in methylene chloride (1 mL) was added triethylsilane (TES, 120 µL) and trifluoroacetic acid (TFA, 1.2 mL) followed by stirring for 30 minutes. The TFA was removed under reduced pressure followed by azeotroping with 3, 5-mL portions of toluene. 20 mL of methylene chloride was added and the mixture was worked up in the usual manner to give 174 mg of free amine (14) as an oil.

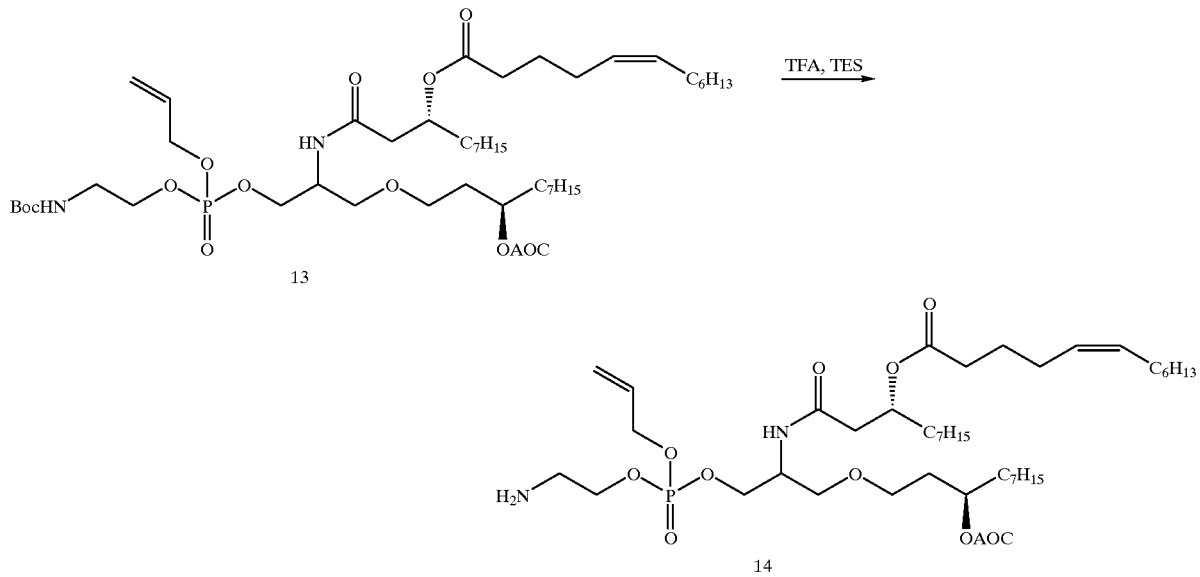

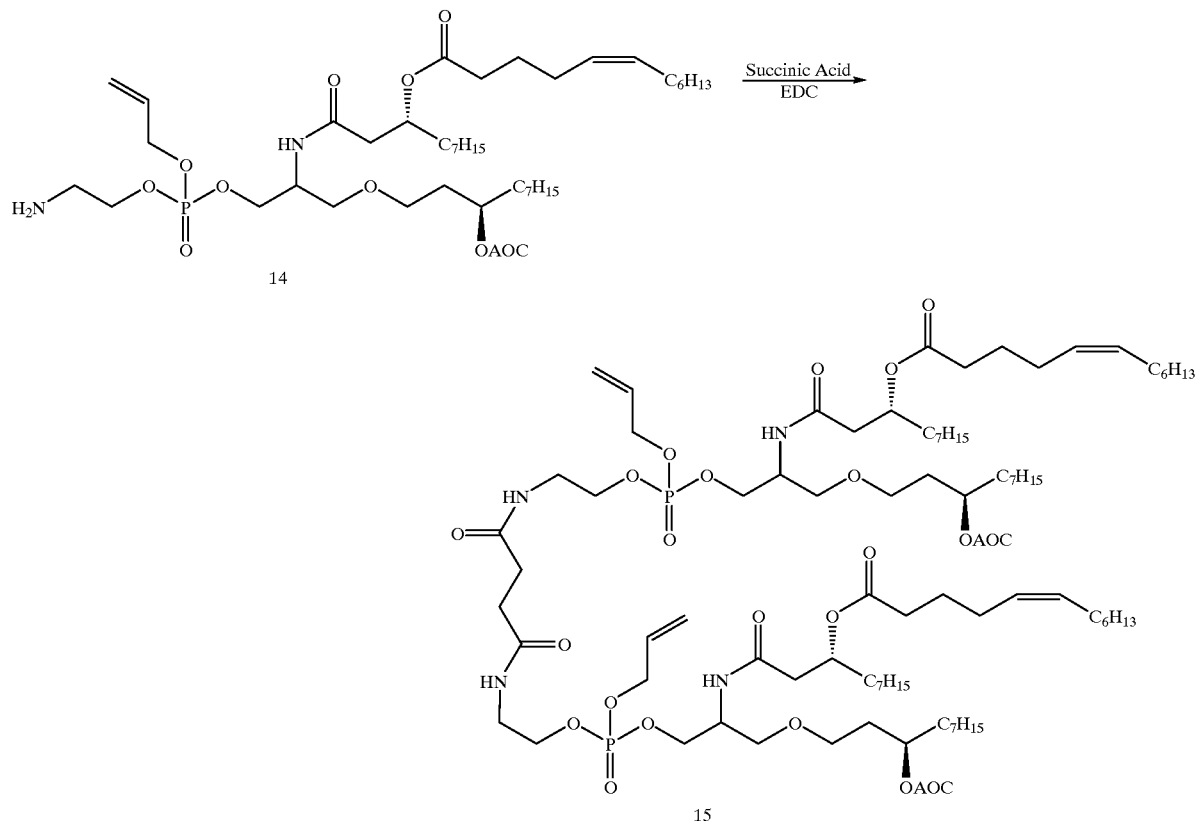
To a dried solution of the free amine (14) (174 mg) in methylene chloride (0.5 mL) was added succinic acid (12.1 mg) and EDC (59 mg). After 1 hour, the reaction was worked up in the usual manner. Chromatography gave 143.1 mg of blocked diphosphate (15) as an oil.
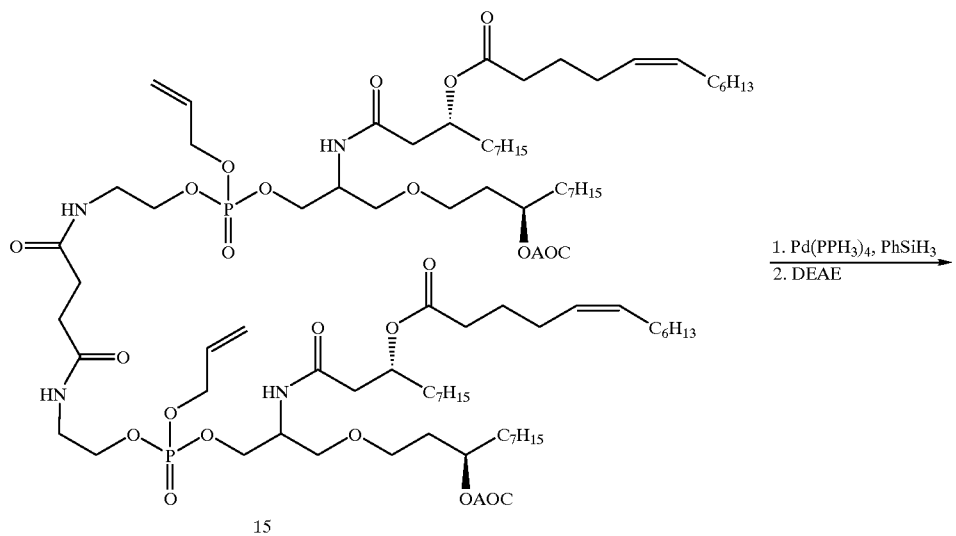

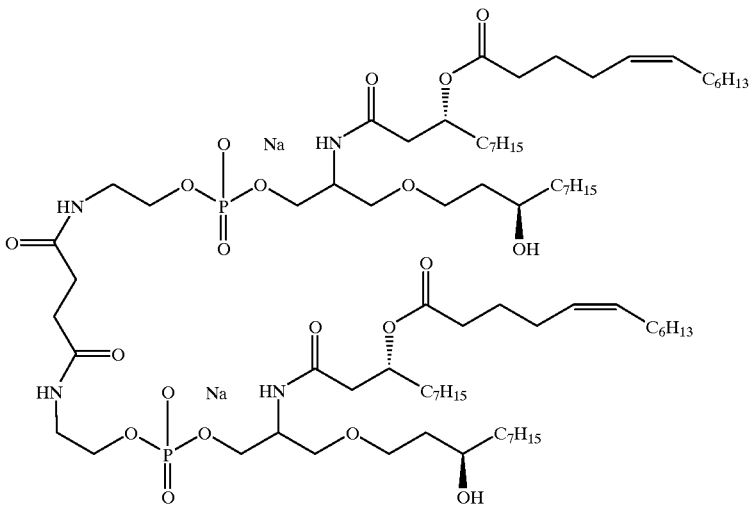

16

To a solution of blocked diphosphate (15) (177.9 mg) in degassed chloroform (1.7 mL) in a dry box was first added phenylsilane (PhSiH$_3$, 50 μL) and then tetrakis-triphenylphosphine palladium (0) (Pd(PPH$_3$)$_4$, 70 mg). After 1 hour, the reaction was removed from the box and chloroform: methanol: water, 2:3: 1, was added and the mixture stirred for 1 hour. It was poured onto a diethylamino-ethylcellulose (DEAE) chromatography column. Elution of the column with a linear gradient of 0.0 M to 0.1 M ammonium acetate in chloroform: methanol: water, 2:3:1, extraction of the desired fractions with an equal volume of chloroform, concentration to dryness and the addition of 0.1 N NaOH (175 μL) followed by lypholization gave 136.2 mg of (16) as a white solid.

Example 2
Chiral Malonate-Type 1

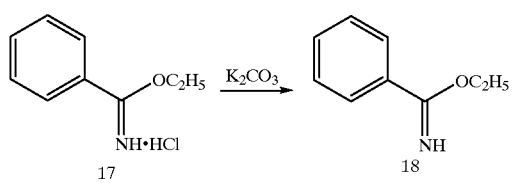

To a cooled solution of potassium carbonate (165 g) in water (575 mL) was added methylene chloride (200 mL) followed by ethyl benzimidate hydrochloride (17) (100 g) after which time the mixture was stirred for 8 minutes. The layers were separated and the aqueous layer extracted with methylene chloride. The organic layers were combined, dried and the solvent removed under reduced pressure to give 83 g of (18).

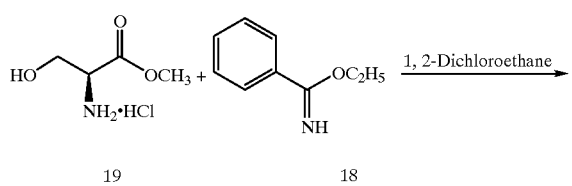

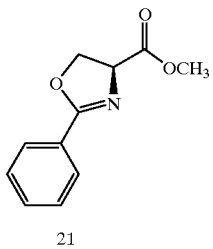

21

To a solution of L-serine methyl ester hydrochloride (19) (41.6 g) in 1,2-dichloroethane (450 mL) was added ethyl benzimidate (18) (36 g). The mixture was heated to reflux for 20 hours, cooled, filtered through diatomaceous earth, and concentrated to dryness to give 56 g of ethyl ester (21) as a white solid.

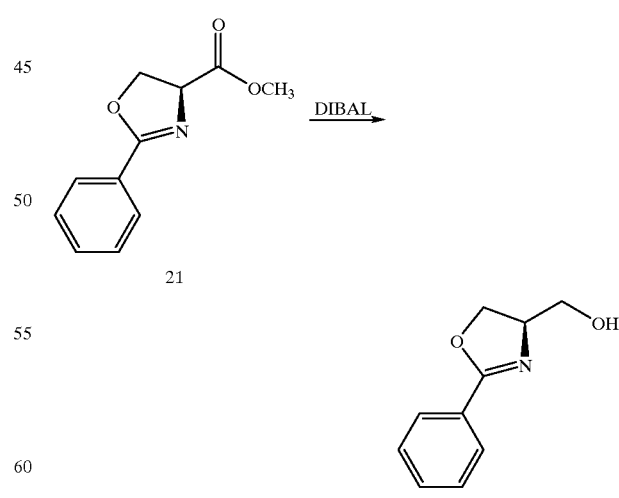

To an ice cold solution of ethyl ester (21) (56 g) in THF (500 mL) was added dropwise diisobutylaluminum hydride (DIBAL, 545 mL of a 1 M solution in hexane). The mixture was allowed to warm to room temperature overnight and then carefully poured onto an aqueous solution of Rochelle's salt (500 g in 1.0 L water). The mixture stirred for 1 hour and worked up in the usual manner. Chromatography gave 25.5 g of alcohol (22) as a white solid.

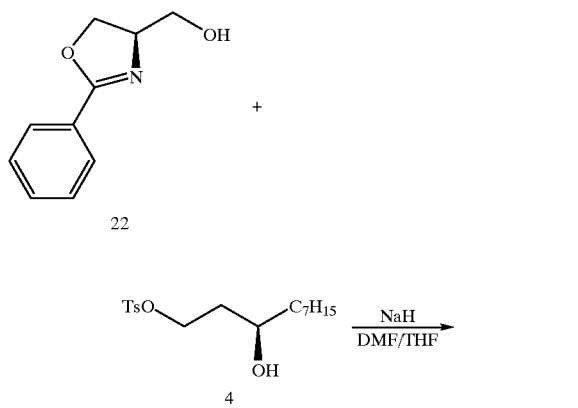

To a suspension of washed sodium hydride (5.3 g of a 60% oil dispersion) in DMF (200 mL) was added the alcohol (22) (24 g) in 250 mL of THF. After 30 minutes, the tosylate (4) was added in 250 mL of THF over 2.5 hours and stirred overnight. The mixture was cooled in ice, methanol was added, the solvent removed under reduced pressure and chromatographed to give

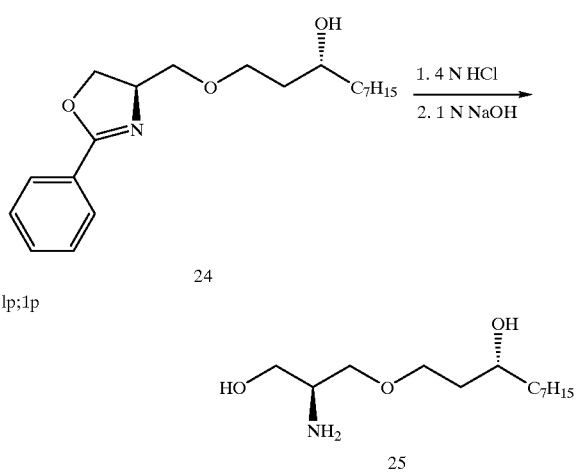

1p;1p

The alcohol (24) (4.3 g) was dissolved in 4 N aqueous hydrochloric acid and heated to reflux for 20 hours. The mixture was cooled, filtered, extracted with ether, made basic with sodium hydroxide and extracted twice with chloroform. The combined chloroform layers were dried and the solvent removed to give 2.88 g of diol (25) as an oil.

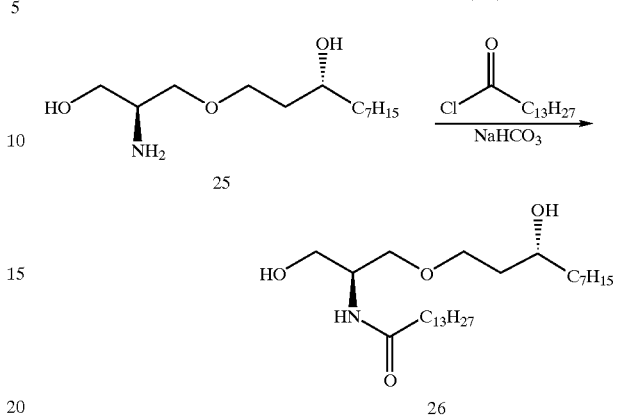

The diol (25)(2.88 g) was dissolved in saturated aqueous sodium bicarbonate (45 mL) and THF (25 mL) and allowed to stir for five minutes. Myristoyl chloride (3.4 mL) was added dropwise over a 25-minute period after which time the reaction mixture was allowed to stir for an additional hour. The reaction was worked up in the usual manner and chromatographed to give 3.07 g of alcohol (26) as an oil.

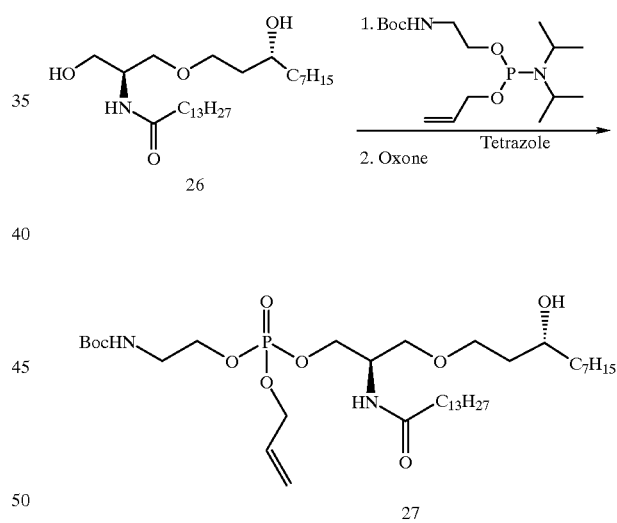

To a solution of the alcohol (26) (1.78 g) in methylene chloride (140 mL) was added tetrazole (683 mg), followed by the phosphorylating reagent (11) (1.6 mL). After 30 minutes, the mixture was cooled in ice, and THF (105 mL) was added followed by an oxone solution (3 g in 90 mL of water). After 5 minutes, the ice bath was removed and the mixture stirred for 30 minutes. The reaction was worked up in the usual manner and chromatographed to give 2.99 g of alcohol (27) as an oil.

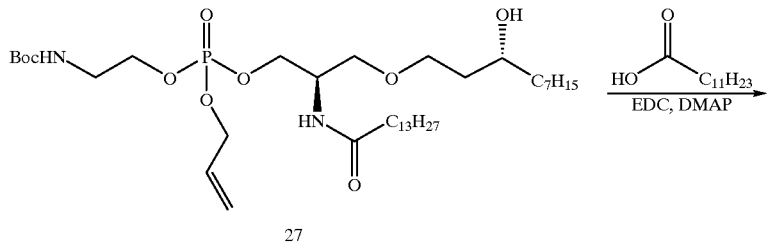

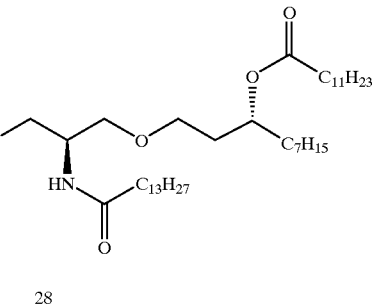

To a solution of the alcohol (27) (3.9 g) in methylene chloride (126 mL) was added EDC (10.8 g), DMAP (66 mg) and dodecyl acid (1.62 g) and stirred overnight. Additional acid (1.6 g), EDC (1 g) and DMAP (0.5 g) was added. After 3 hours, the reaction was worked up in the usual manner and chromatographed to give 2.07 g of N-BOC-protected amine (28).

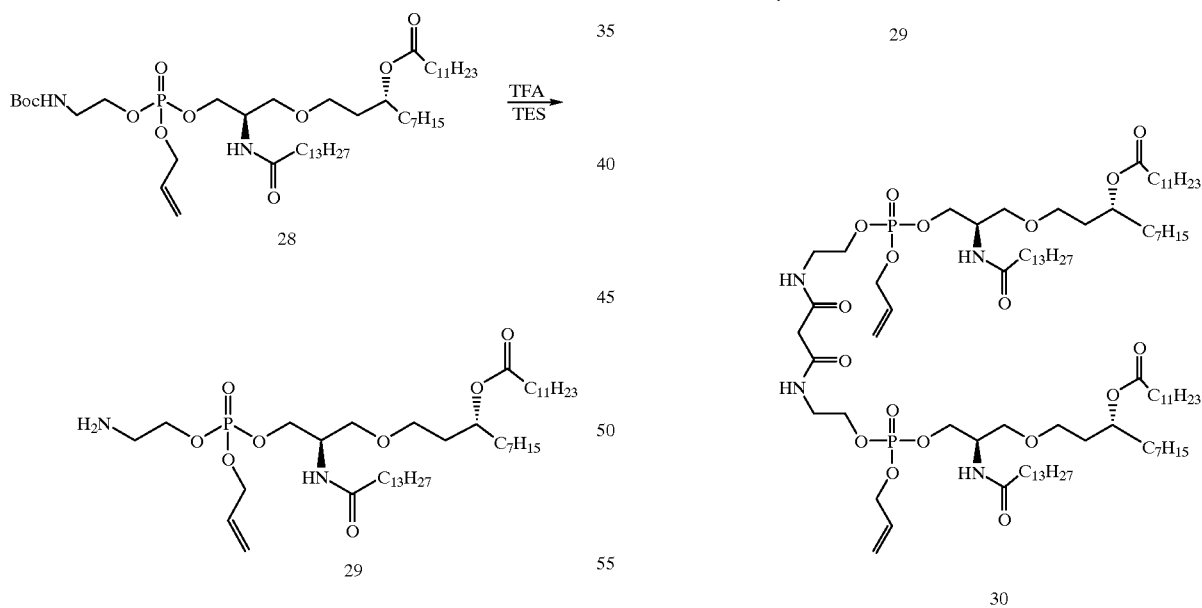

To a solution of the N-BOC-protected amine (28)(187.3 mg) in methylene chloride (1.5 mL) was added TES (240 μL) and TFA (300 μL) and the mixture stirred for 45 minutes. Toluene was added and the solvent removed under reduced pressure. The residue was dissolved in methylene chloride and worked up in the usual manner to give 154 mg of amine (29) as an oil.

To an ice cold solution of the amine (29) (75.6 mg) and malonic acid (4.8 mg) in methylene chloride (0.5 mL) was added EDC (27 mg), followed by removal of the cooling bath. After 1 hour, a trace of DMAP was added. After 2.5 hours, the mixture was directly chromatographed to give 54.1 mg of dimer product (30).

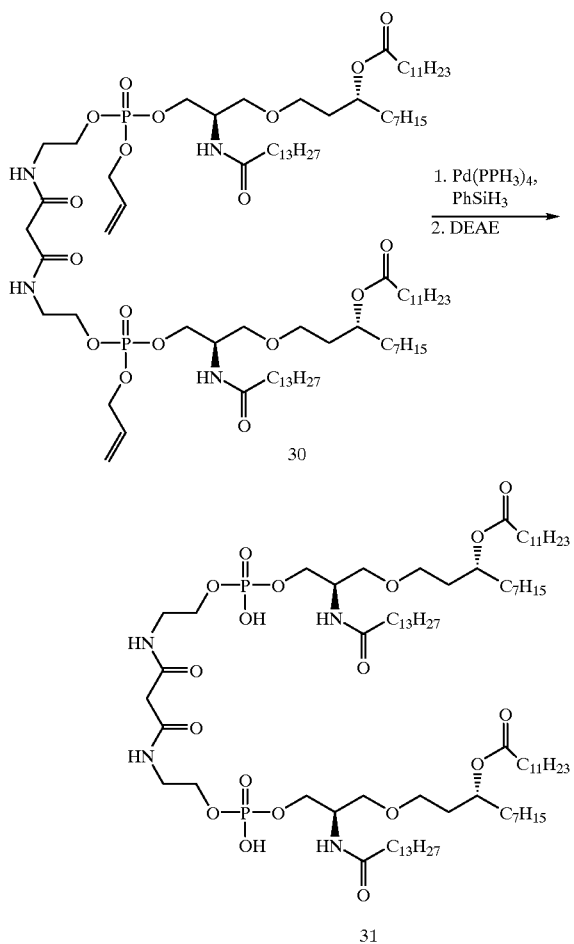

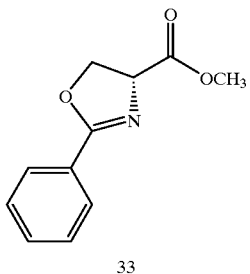

To a solution of D-serine methyl ester hydrochloride (32) (25 g) in dichloroethane (270 mL) was added ethyl benzimidate (20) (24 g). After 20 hours at reflux, the mixture was cooled to room temperature, filtered through diatomaceous earth and the solvent removed under reduced pressure to give 34 g of methyl ester (33) as a white solid.

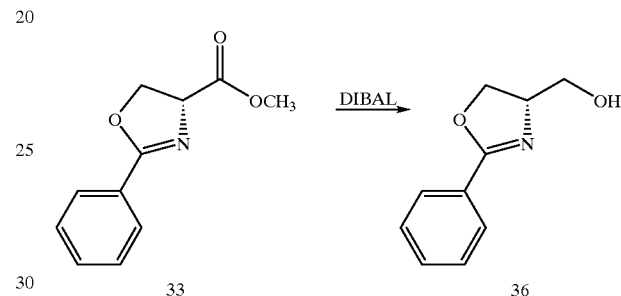

To a solution of the dimer (30) (54 mg) in degassed chloroform (2 mL) was added PhSiH$_3$ (14 μL) and Pd(PPh$_3$)$_4$ (18 mg) followed by removal of the cooling bath. After 1 hour, the reaction was quenched with chloroform:methanol:water (2:3:1) and poured onto a DEAE cellulose chromatography column and chromatographed to give a semi-solid. The solid was dissolved in sterile water and 0.1 N aqueous sodium hydroxide (306 μL) was added and the mixture lyophilized to yield white solid (31) (25 mg).

To a ice cold solution of the methyl ester (33) (34 g) in THF (300 mL) was added dropwise a solution of DIBAL in hexane (1.0 M, 322 mL). The mixture was allowed to warm to room temperature overnight and then carefully poured into an aqueous solution of Rochelle's salt. The mixture was then stirred for 1 hour and worked up. Chromatography gave 18.6 g of alcohol (36) as a white solid.

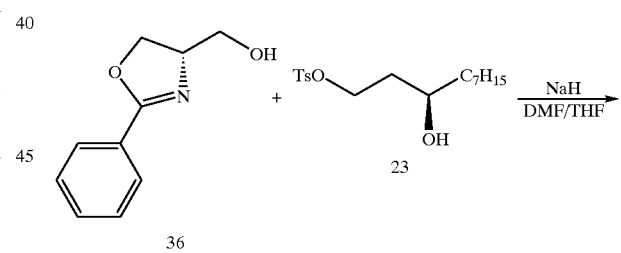

Example 3

Chiral Malonate-Type 2

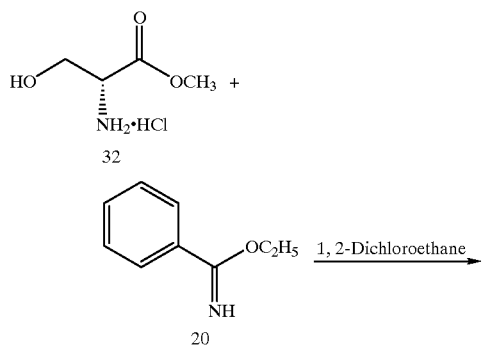

To a suspension of washed sodium hydride (4 g of a 60% oil suspension) in DMF (100 mL) was added a solution of the alcohol (36) (8.6 g) in THF (40 mL). The mixture was stirred for 1 hour and a solution of the tosylate (23) (17.5 g) in THF (40 mL) was added. The mixture was stirred overnight and then additional tosylate (23) was added (5 g) and stirred for another 4 hours. Methanol was added to the cooled reaction mixture, the solvent was removed under reduced pressure, and the residue was chromatographed to give 1.03 g of alcohol (37) as a solid.

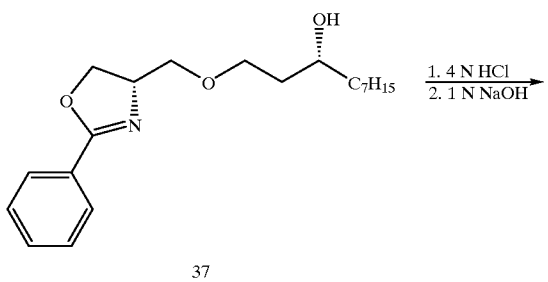

37

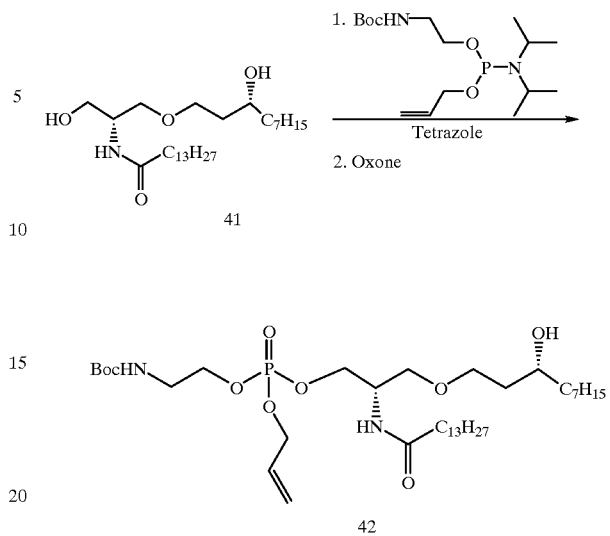

41

42

To a solution of the amide-diol (41) (531 mg) in methylene chloride (40 mL) was added tetrazole (203 mg) and the mixture was stirred for 5 minutes. Then phosphorylating reagent (11) (482 mg) was added. After 20 minutes, additional phosphorylating reagent (11) (100 mg) was added and after an additional 20 minutes, 100 mg more was added. After an additional 20 minutes, 50 mg more was added. After 20 minutes, the mixture was poured into a cold solution of THF (30 mL)/oxone (1.07 g)/water (30 mL). The mixture was stirred at 0° C. for 5 minutes, and then 20 minutes at room temperature after which time the reaction was worked up in the usual manner. Chromatography gave 852 mg of phosphate alcohol (42) as an oil.

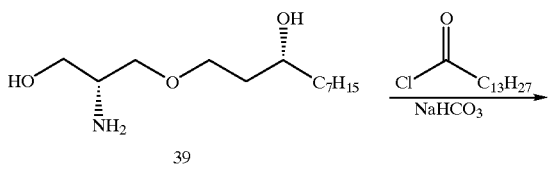

39

The alcohol (37) (1.03 g) was dissolved in 4 N aqueous hydrochloric acid (25 mL) and the mixture was heated to 100° C. for 20 hours. Additional hydrochloric acid (5 mL) was added and the reflux continued for 6 hours. The mixture was cooled, washed with ether, made basic with 1 N aqueous sodium hydroxide, and extracted (3×) with chloroform. The combined chloroform layers were dried and the solvent removed under reduced pressure to give 553 mg of amino-diol (39).

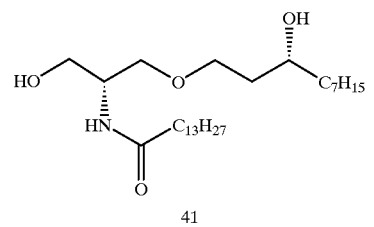

39

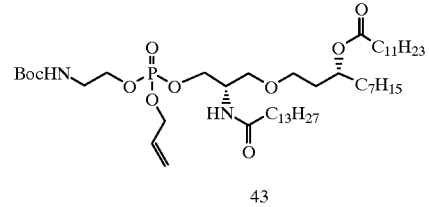

42

43

41

To a solution of amino-diol (39) (553 mg) in THF (3 mL) was added saturated aqueous sodium bicarbonate (6 mL) followed by myristoyl chloride (628 μL). After 50 minutes, the reaction was worked up in the usual way. Chromatography gave 389 mg of amide-diol (41) as an oil.

To a solution of the phosphate alcohol (42) (3.9 g) in methylene chloride (126 mL) was added EDC (10.8 g), DMAP (66 mg) and dodecyl acid (1.62 g). The reaction mixture was stirred overnight. Additional acid (1.6 g), EDC (1 g) and DMAP (0.5 g) was added. After 3 hours, the reaction was worked up in the usual manner and chromatographed to give 2.07 g of protected amine (43).

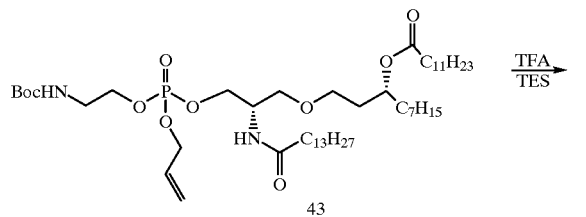

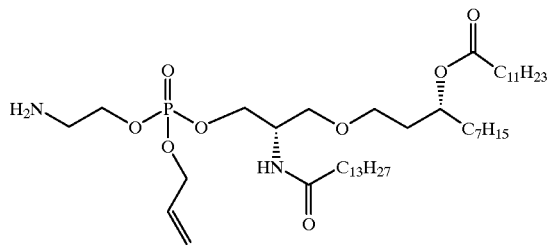

To a solution of the protected amine (43) (194 mg) in methylene chloride (1.5 mL) was added TES (240 μL), and TFA (300 μL). The mixture was stirred for 20 minutes and additional TES (50 μL) and TFA (50 μL) was added. After 1 hour, toluene was added and the solvent removed under reduced pressure and then the mixture was worked up in the usual manner. The crude free amine product (44) was used immediately in the next reaction.

malonate (8.3 μL), EDC (12.4 mg) and a trace of DMAP. The ice bath was removed and after 2 hours, the reaction was worked up in the usual manner. Chromatography gave 44 mg of amide (45).

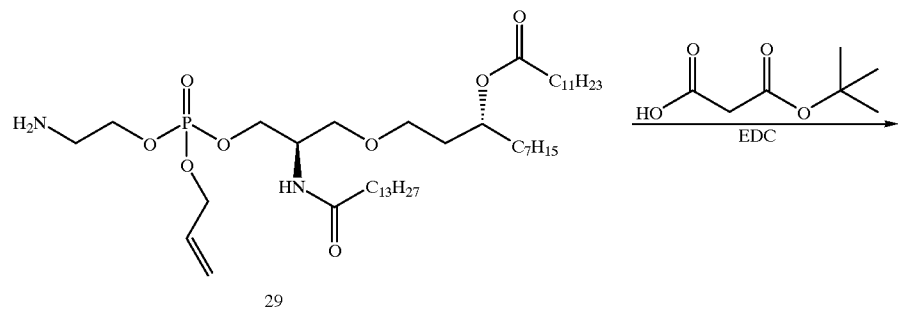

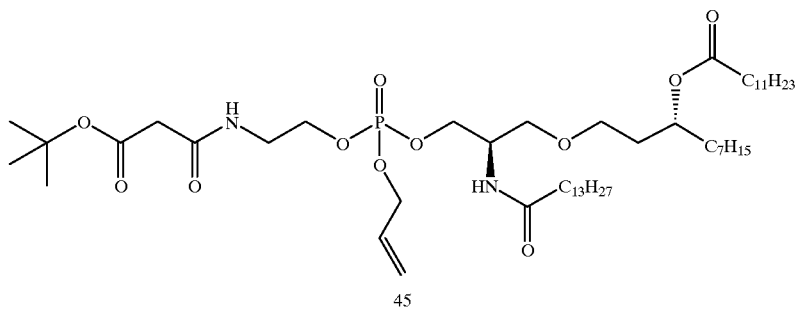

To an ice cold solution of the free amine (29) (43.5 mg) in methylene chloride (250 μL) was added mono-t-butyl

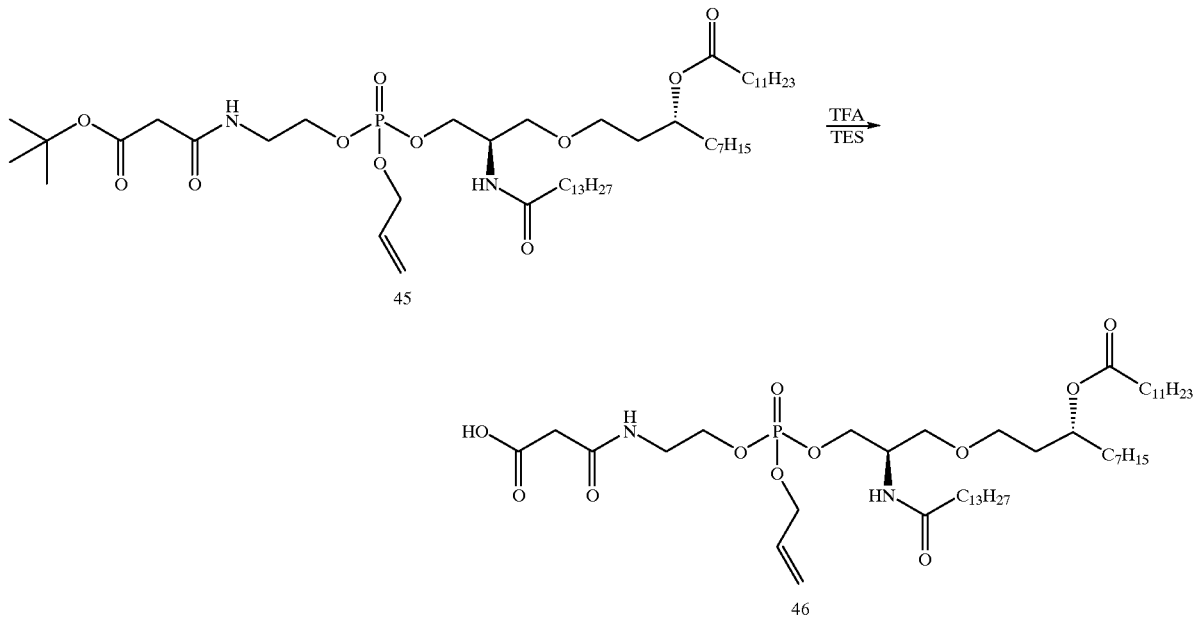
To a solution of the amide (45) (44 mg) in methylene chloride (0.5 mL) was added TES (90 µL) and TFA (100 µL). After 2 hours, toluene was added and the solvent removed under reduced pressure. The mixture was worked up in the usual manner to give 44.2 mg of free acid (46).
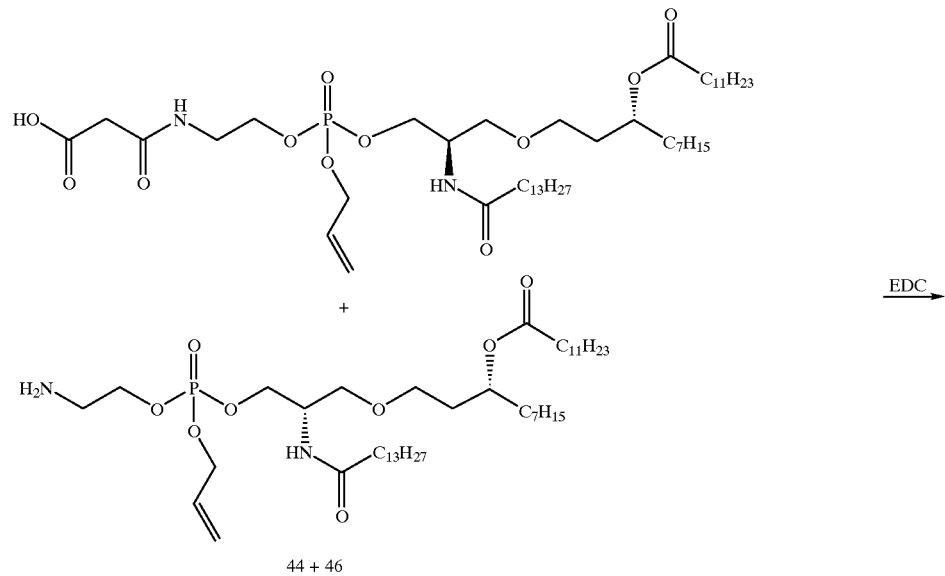

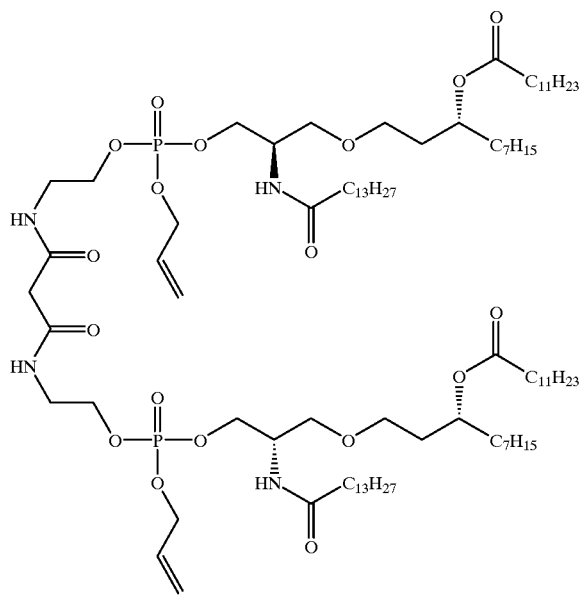

47

To an ice cold solution of the free acid (46)(41 mg) and the free amine (44) (26.3 mg) in methylene chloride (500 μL) was added EDC (13 mg) and the mixture was stirred for 30 minutes. Additional EDC (5 mg) and DMAP (2 mg) was added and after 1 hour, the reaction was worked up in the usual manner. Chromatography gave 32.7 mg of coupled compound 47 as an oil.

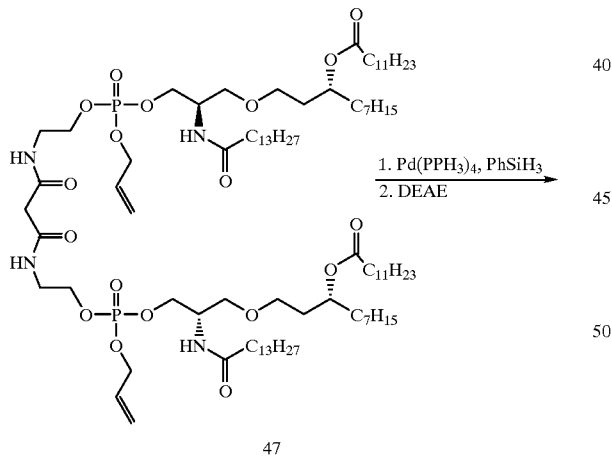

47

-continued

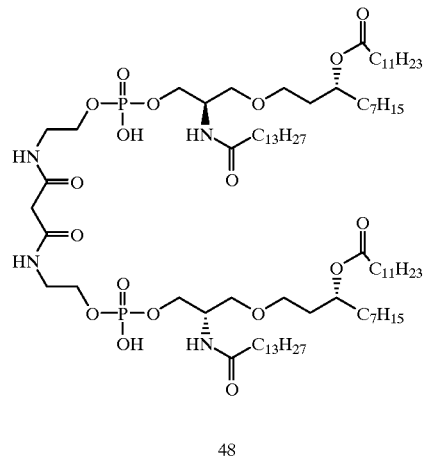

48

To a solution of the coupled compound (47) (32.7 mg) in degassed chloroform (1.5 mL) in a dry box was added PhSiH$_3$ (8.5 μL) and Pd(PPH$_3$)$_4$ (11 mg). The mixture was removed from the box and cooled in ice. After 5 minutes, the ice bath was removed and after 1 hour, chloroform:methanol:water (2:3:1) was added and the mixture stirred for 15 minutes and stored in the freezer overnight. The mixture was then poured onto a DEAE chromatography column. Chromatography gave 13.9 mg of a compound (48) as a white powder after 0.1 N NaOH treatment followed by lyophilization.

Example 4

Chiral Urea-Type 1

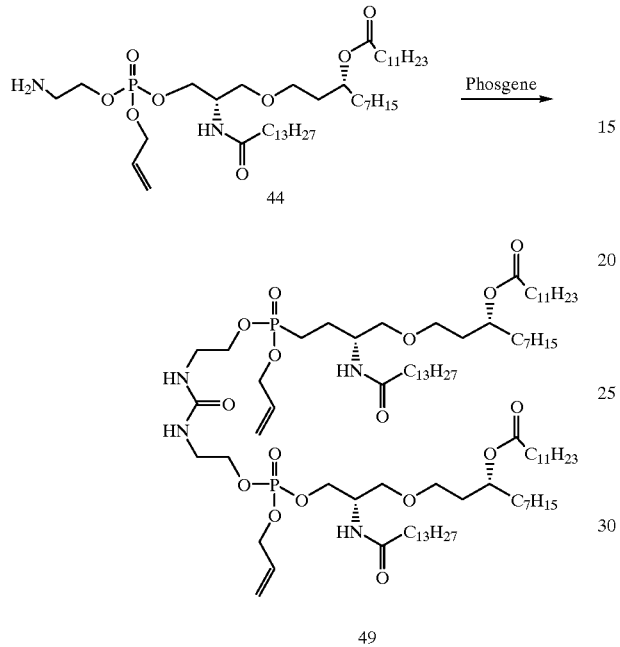

44

49

To a solution of amine (44) (46.1 mg) in toluene was added saturated sodium bicarbonate (0.5 mL) followed by phosgene (15 μL of a 1.93 M solution in toluene). After 30 minutes, additional phosgene (10 μL) was added. After 2 hours, additional phosgene (5 μL) was added. The reaction was quenched with aqueous sodium bicarbonate and worked up in the usual manner to give 29.6 mg of urea (49) with protected phosphates.

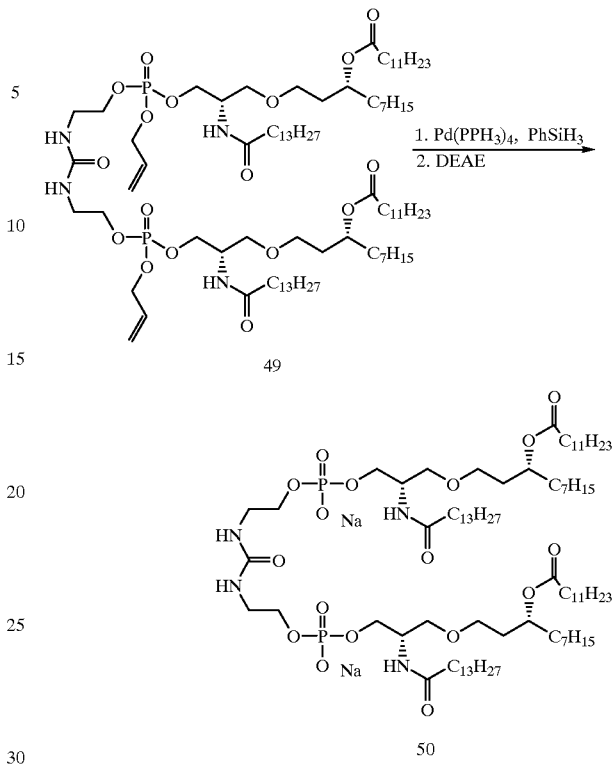

49

50

To a solution of the urea with protected phosphates (49) (29.6 mg) in degassed chloroform (1.5 mL) in a dry box was added PhSiH$_3$ (8 μL). The reaction vessel was removed from the dry box and placed on ice. Pd(PPh$_3$)$_4$ (10 mg) was added and after 5 minutes the ice bath removed. After 1 hour, the reaction was quenched by addition of chloroform:methanol:water. The mixture was stirred for 15 minutes and stored overnight in the freezer. It was chromatographed on DEAE to give 24.1 mg of (50) as a white powder after 0.1 N NaOH treatment followed by lyophilization.

Example 5

Chiral Urea-Type 2

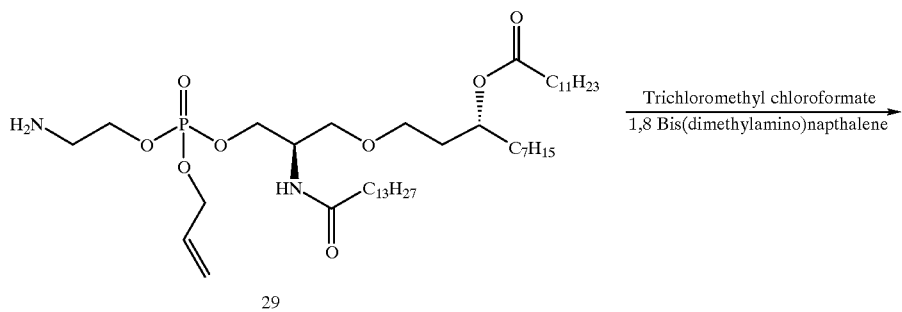

29

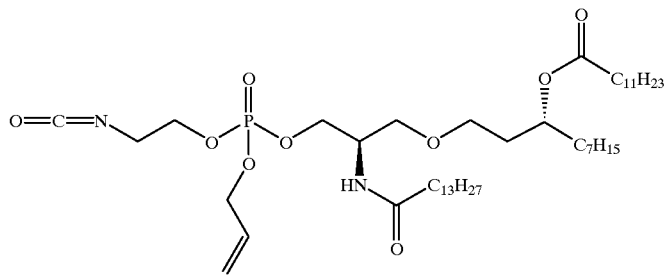

51

To an ice-cold solution of trichloromethyl chloroformate (2.6 µL) in methylene chloride (200 µL) was added a solution of free amine (29) (35 mg) and 1,8-bis-(dimethylamino)-naphthalene in methylene chloride (200 µL). After 5 minutes, the ice bath was removed. After 15 minutes, additional methylene chloride was added and the mixture worked up in the usual manner. Chromatography gave 9.4 mg of isocyanate (51) as an oil.

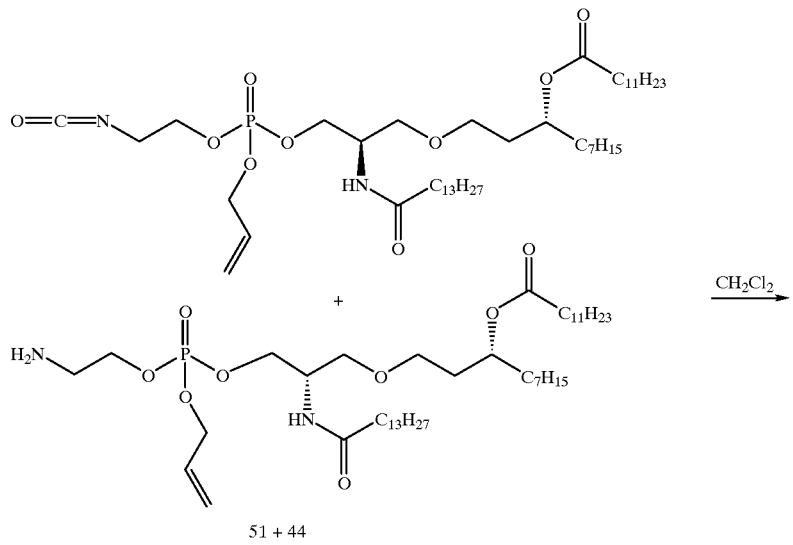

51 + 44

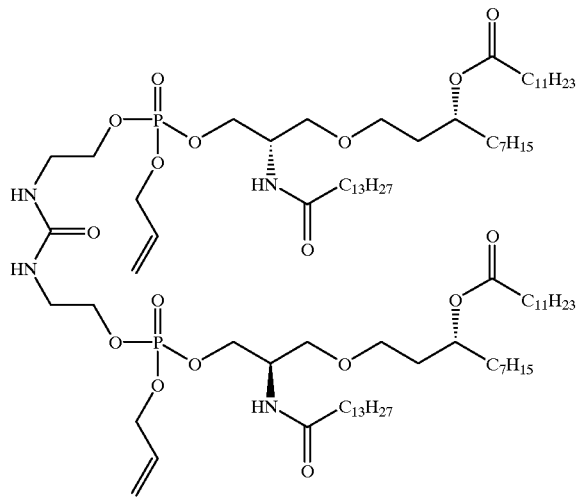

61

To a solution of the isocyanate (51) (9.4 mg) in methylene chloride (0.2 mL) was added a solution of the amine (44) (10.3 mg) in methylene chloride. After 15 minutes, the reaction was worked up in the usual manner. Chromatography gave 5.5 mg of coupled compound (61) as an oil.

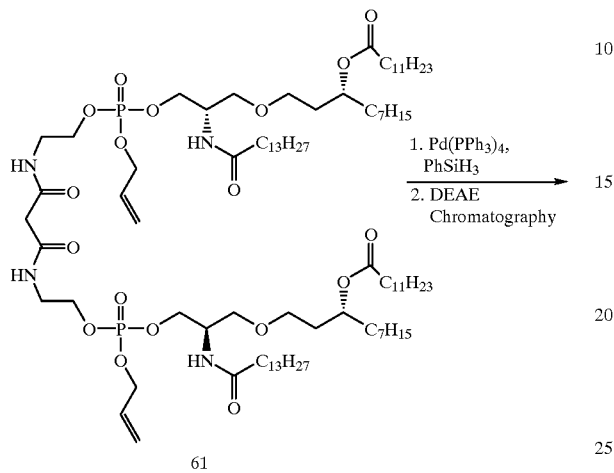

To a solution of the coupled compound (61) (25.2 mg) in degassed chloroform (0.5 mL) in a dry box was added PhSiH$_3$ (6.6 μL) and Pd(PPH$_3$)$_4$ (8.8 mg). The mixture was removed from the box and cooled in ice. After 5 minutes, the ice bath was removed and after 1 hour, chloroform:methanol:water (2:3:1) was added and the mixture stirred for 15 minutes and stored in the freezer overnight. The mixture was then poured onto a DEAE chromatography column.

Chromatography gave 7.5 mg of (62) as a white powder after 0.1 N NaOH treatment followed by lyophilization.

Example 6
Chiral Glycerol Analogue of Type 1

To a stirred suspension of sodium hydride (145.5 mg of 60% oil dispersion washed with hexanes) in DMF (12 mL) was added (S)-(+)-alcohol (63) (0.41 mL) in 8 mL of THF dropwise over a 1 hour period. The mixture was stirred for an additional 30 minutes followed by a dropwise addition of the tosylate (4) (0.789 g) in 10 mL of THF over a 1 0-minute period. The resulting reaction mixture was stirred overnight. The usual work up gave 0.56 mg of the desired adduct (65).

A solution of lauric acid (1.40 g), EDC (1.35 g), DMAP (0.04 g) and the alcohol adduct (65) (0.564 g) in 4 mL of methylene chloride was stirred for 15 hours at room temperature. Brine and saturated aqueous sodium bicarbonate (1:1) were added and the mixture extracted with methylene chloride. The mixture was worked up in the usual manner and chromatographed. The desired fraction was dissolved in 20 mL of 4:1 acetic acid: water and stirred for 15 hours. The solvent was removed under reduced pressure and the residue chromatographed to give 0.77 g of semi-solid diol (66).

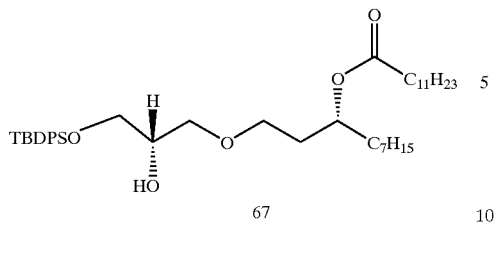

67

A solution of the diol (66) (0.22 g), DMAP (6.3 mg), TEA (100 μL) and TBDPSCl (164 μL) was stirred for 24 hours at room temperature. Methanol (2 mL) and a trace of aqueous hydrochloric acid was added followed by extraction with methylene chloride. The mixture was worked up in the usual way. The residue was chromatographed to give 0.3 g of alcohol (67) as an oil.

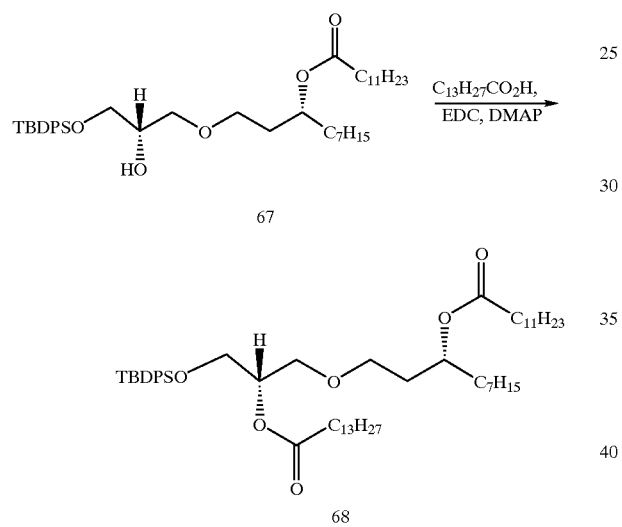

A solution of the alcohol (67) (0.3 g), DMAP (5.5 mg), EDC (258 mg), myristic acid (308 mg) in methylene chloride (4 mL) was stirred for 18 hours at room temperature followed by the addition of brine and saturated sodium bicarbonate. The mixture was worked up in the usual way and chromatographed to give 0.4 g of silyl protected ether product (68).

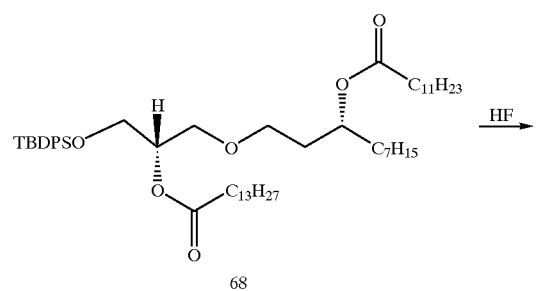

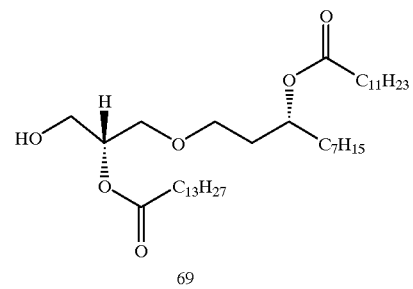

69

To a solution of the silyl protected ether (68) (195 mg) in acetonitrile (2.7 mL) was added 48% hydrofluoric acid (0.756 ml). After 30 hours, saturated sodium bicarbonate was added and the mixture worked up in the usual way. Chromatography gave 94.7 mg of free alcohol (69).

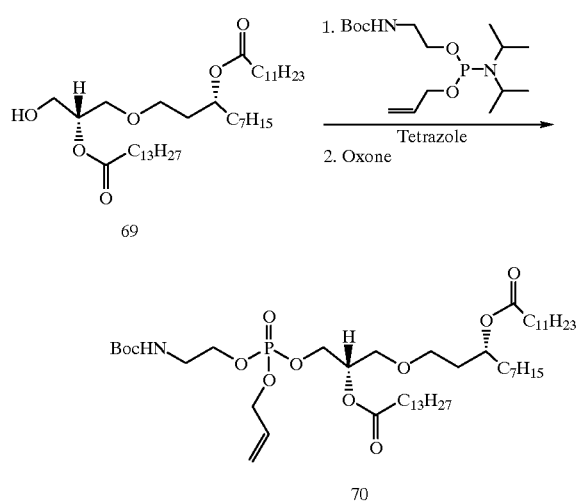

To a solution of the free alcohol (69) (57 mg) in methylene chloride (0.5 mL) was added tetrazole (15.6 mg) and phosphorylating reagent (11) (40 mg) at room temperature. After four hours, the mixture was cooled to 0° C. followed by the addition of oxone (82 mg) in THF (0.5 mL): water (0.6 mL). The mixture was warmed to room temperature and stirred for 80 minutes. The final reaction mixture was worked up in the usual manner. Chromatography gave 72 mg of protected phosphate (70).

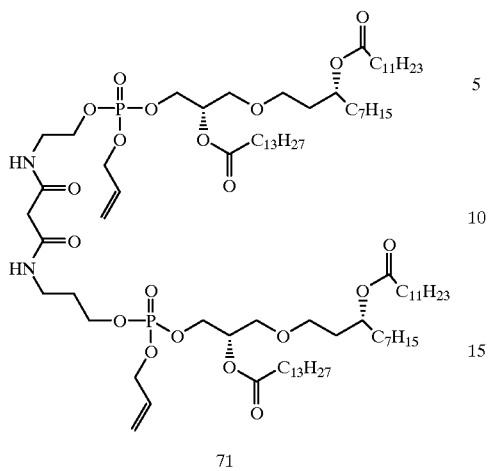

71

To a solution of the protected phosphate (70) (72 mg) in methylene chloride (1 mL) was added TES (120 μL) and trifluoroacetic acid (0.6 mL) followed by stirring for 1 hour. The TFA was removed under reduced pressure followed by azeotroping with 10 mL of toluene. 20 mL of methylene chloride was added and the mixture was worked up in the usual manner to give 0.52 g of an oil.

The crude amine was dissolved in methylene chloride (0.7 mL) followed by the addition of malonic acid (4.5 mg) and EDC (25.6 mg). The mixture was stirred overnight and worked up in the usual way to give 32.5 mg of the dimer product (71).

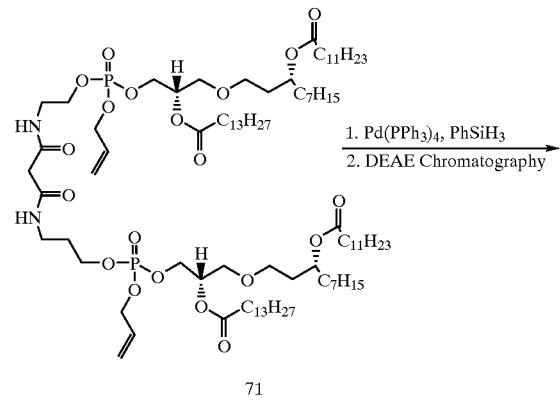

71

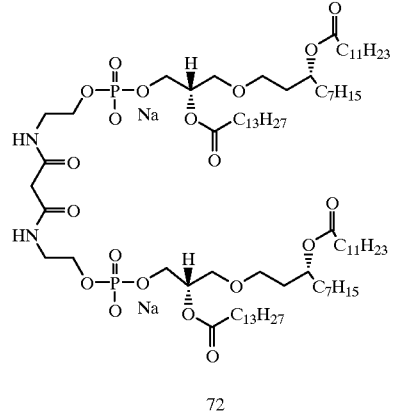

72

The protected dimer (71) (32.5 mg) from the preceding reaction was dissolved in degassed chloroform (2 mL) and PhSiH$_3$ (8.6 μL) was added in a dry box. The mixture was removed from the dry box and Pd(PPh$_3$)$_4$ (22.6 mg), previously weighed in the dry box, was added. After 2 hours, the mixture was chromatographed on DEAE to give 27.9 mg of white solid (72) after the addition of 1N sodium hydroxide (34.2 μL) followed by lyophilization.

Preparation of ER-804253

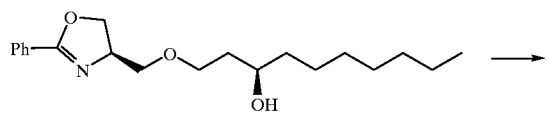

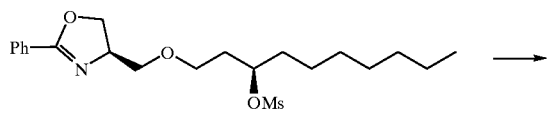

The alcohol (558 mg) was dissolved in methylene chloride (5 mL) cooled to 0° C. and triethylamine (0.466 mL) was added under a nitrogen atmosphere. After stirring for 5 minutes methanesulfonyl chloride (0.142 mL) was added dropwise. The mixture was stirred for an additional 5 minutes at 0° C. and then warmed to room temperature. After stirring for an additional hour, the mixture was worked up with sat. sodium bicarbonate, extracted with ethyl acetate and the extract washed with water, dilute aqueous hydrochloric acid, water, brine, dried and the solvent removed to give 630 mg.

The mesylate (630 mg) and sodium azide (299 mg) were dissolved in DMSO (6 mL) and heated to 60° C. for 90 minutes. After cooling to room temperature the reaction mixture was diluted with methylene chloride, washed with water and brine. After extracting the aqueous washes the combined organic was dried, concentrated, purified over silica gel using a 4:1 ratio of hexanes to ethyl acetate and the dried product fractions give 420 mg.

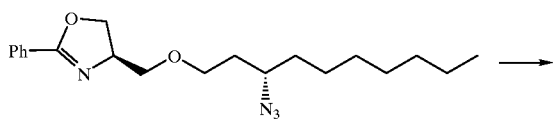

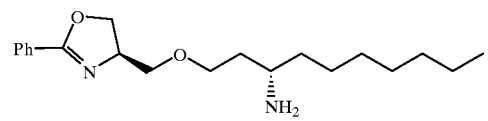

The azide (295 mg) was dissolved in ethanol (5 mL) and Lindlar catalyst (200 mg) was added. After stirring under an atmosphere of hydrogen gas at atmospheric pressure, the filtered solution was dried to give 274 mg.

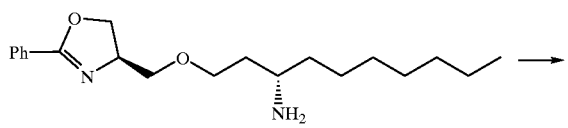

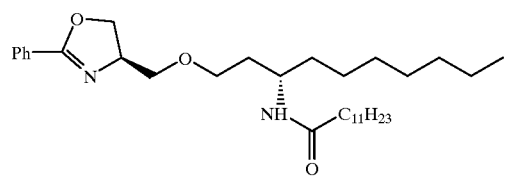

The amine (930 mg) was dissolved in THF (10 mL) and sat. sodium bicarbonate (22 mL). After stirring for 5 minutes, lauroyl chloride (0.712 mL) was added dropwise over 20 minutes. The final mixture was extracted with chloroform, dried to give 1.45 g.

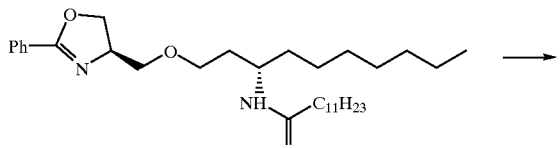

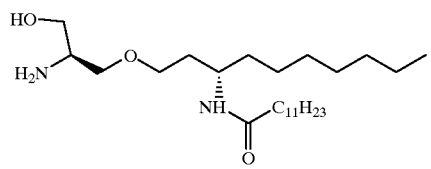

The amide (1.11 g) was dissolved in methanol (14 mL) and 4 N hydrochloric acid (8 mL) added. The mixture was stirred for 1 hour at 50° C. and then concentrated. Methanol (16 mL) and 40% sodium hydroxide (8 mL) was added and the mixture refluxed for 1 hour. It was cooled, extracted with methylene chloride and the extract washed with water, dried and the solvent removed to give 930 mg.

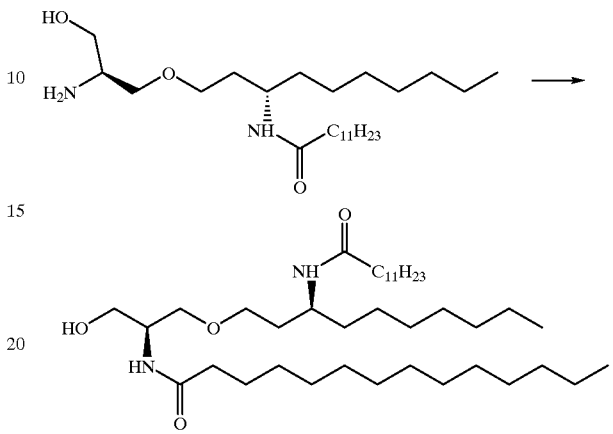

The amino alcohol was dissolved in THF (6 mL) and saturated sodium bicarbonate added (13 mL). After 5 minutes the mixture was cooled to 0° C. and myristoyl chloride (300 μL) added. After 30 minutes, the mixture was worked up in the usual way to give 430 mg.

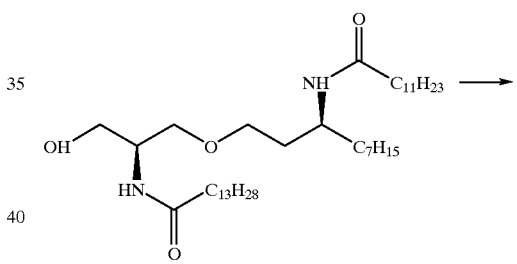

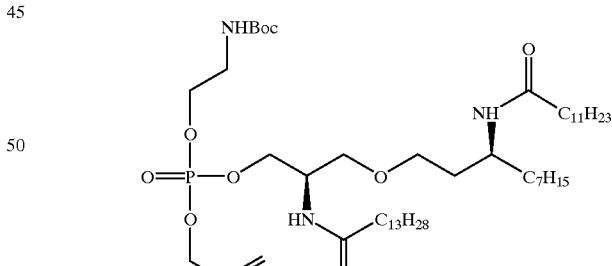

The alcohol (101.7 mg) was dissolved in ice cold methylene chloride and phosphorylating reagent 11 (90 μL) was added and the mixture stirred for 30 minutes. Ice cold oxone (166.3 mg) was added and the mixture stirred for 30 minutes. The reaction was quenched with thiosulfate. The mixture was worked up the usual way and chromatographed to give 174 mg (not purified)

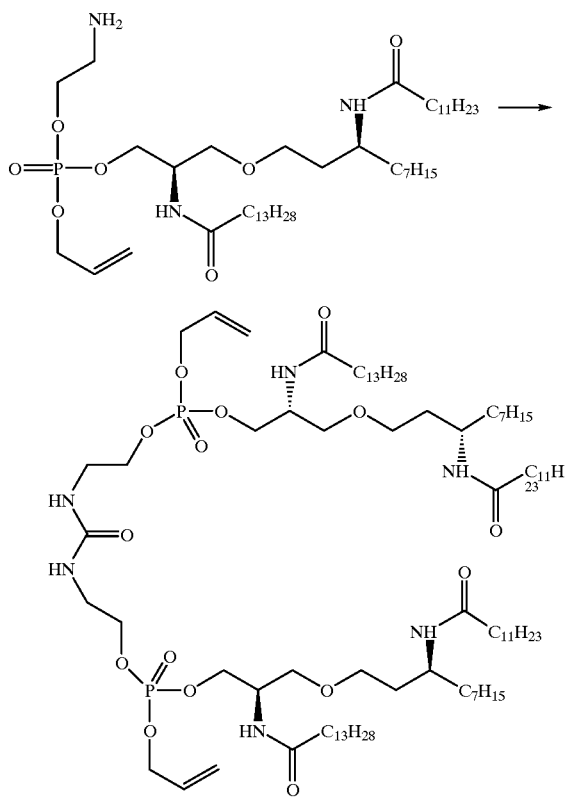

The protected amine from the above reaction was dissolved in ice cold methylene chloride (1 mL), trifluoroacetic acid (1 mL) was added and the mixture stiffed for 1 hour. The TFA was removed and the mixture purified to give 106.7 mg.

The amine was dissolved in methylene chloride (3 mL) and saturated. sodium bicarbonate solution (3 mL) was added. The mixture was cooled in ice and phosgene in toluene (0.55 equiv.) was added dropwise. The mixture was stirred for 20 minutes and worked up to give 112.3 mg.

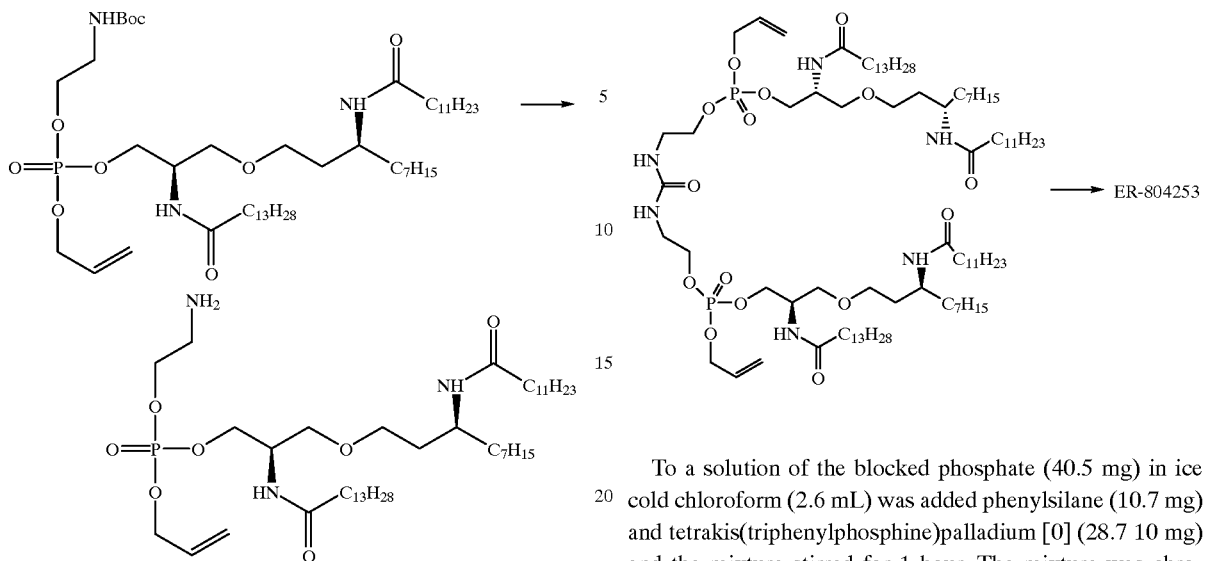

To a solution of the blocked phosphate (40.5 mg) in ice cold chloroform (2.6 mL) was added phenylsilane (10.7 mg) and tetrakis(triphenylphosphine)palladium [0] (28.7 10 mg) and the mixture stirred for 1 hour. The mixture was chromatographed on a DEAE column to give 27.7 mg of ER-804253.

Preparation of ER-804130

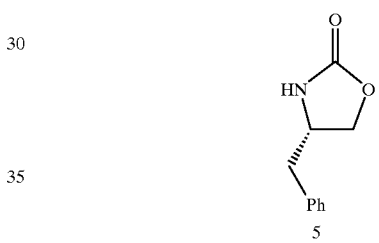

To a solution of the amide (3 g) in THF (65 mL) at −78° C. was added an equivalent of butyllithium, followed by a solution of nonanoyl chloride in THF (6 mL). Aqueous ammonium chloride was added and the mixture worked up in the usual manner to give 5.35 g.

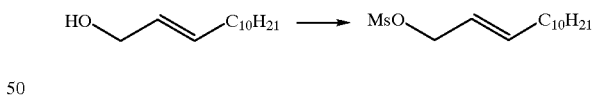

To a solution of the alcohol (5 g) in ice cold methylene chloride (100 mL) was added triethylamine (4.1 mL) and mesyl chloride (2.1 mL). The mixture was stirred for 4 hours and worked up in the usual manner to give 6.99 g.

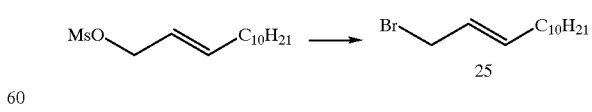

The a solution of the mesylate (6.99 g) in ice cold DMF (100 mL) was added potassium bromide. The mixture was allowed to warm to room temperature and stirred for five hours. It was worked up in the usual manner to give 4.63 g of clear oil.

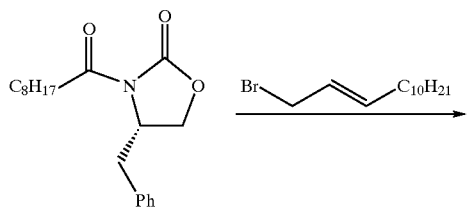

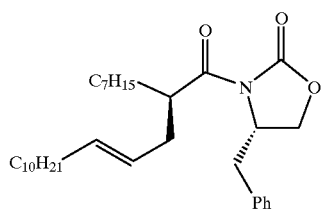

A solution of the amide (2.8 g) in THF (15 mL) was added to a −78° C. solution of sodium bis-trimethylsilylamide in THF (15 mL). After 1 hour, the bromide was added and the mixture allowed to warm to room temperature and worked up in the usual manner to give 1.02 g.

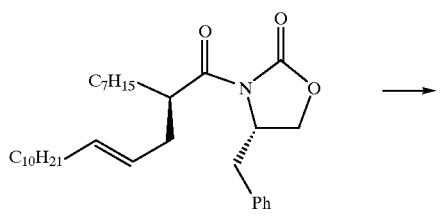

To a solution of the olefin (1.02 g) in EtOAc was added palladium on carbon (126 mg) and the mixture placed under hydrogen. After 4 hours, the mixture was worked up in the usual manner to give 1.0 g.

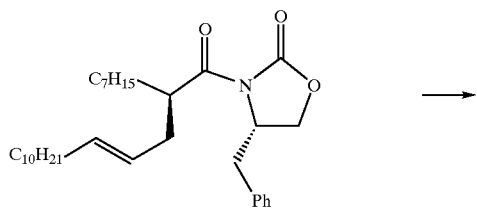

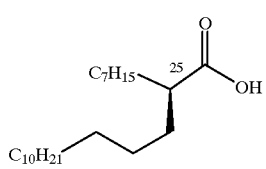

To a solution of the amide (1.0 g) in ice cold THF (20 mL) was added water, hydrogen peroxide and lithium hydroxide. The next day, the mixture was worked up in the usual manner to give 590 mg of acid.

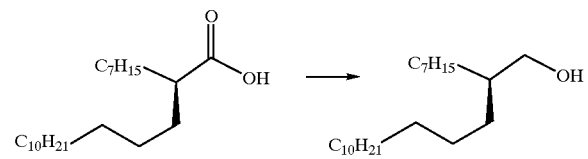

To a solution of the acid in ice cold THF (10 mL) was added diborane:THF complex and the mixture allowed to warm slowly. After seven hours, dilute hydrochloric acid was added carefully and the mixture worked up in the usual manner. The crude material was dissolved in ice cold ether and LAH solution (2 mL of 1 M) added. After 5 minutes, the mixture was worked up in the usual manner to give 556 mg of the alcohol.

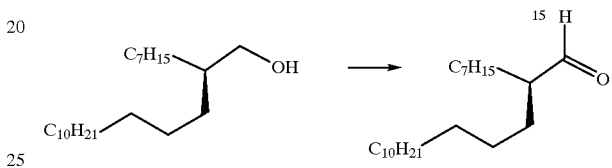

To a −78° C. solution of oxalyl chloride (2.2 mL) in methylene chloride (10 mL) was added DMSO (1.1 mL) and after 2 minutes the alcohol (556 mg) was added in methylene chloride (5 mL). After 20 minutes, triethylamine (1 mL) was added and the mixture warmed to 0° C. The mixture was diluted with ether and worked up in the usual manner to give 567 mg.

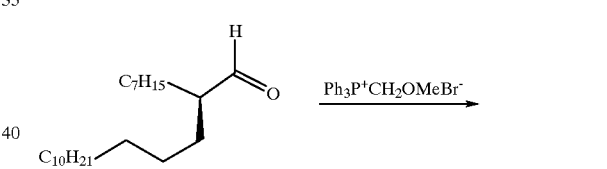

The Wittig reagent (679 mg) was suspended in THF (10 mL) and KHMDS solution (4 mL of 0.5 M) added. After 20 minutes, the mixture was cooled to −78° C. and the aldehyde (567 mg) in THF (5 mL) was added. After 15 minutes, the mixture was worked up in the usual manner to give 342 mg.

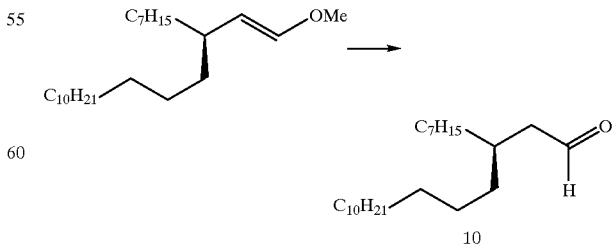

To a solution of the enol ether (342 mg) in acetonitrile (3.5 mL) and water (0.15 mL) was added hydroiodic acid. After 4 hours, the mixture was worked up in the usual manner to give 325 mg.

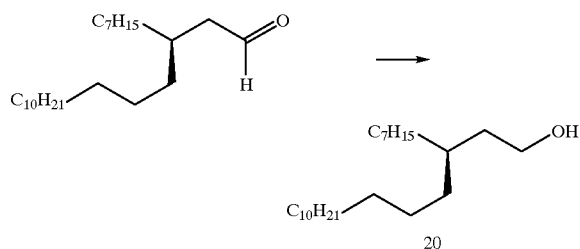

To a solution of the aldehyde (325 mg) in methanol (10 mL) was added sodium borohydride (38 mg). After 3 hours, the reaction was worked up in the usual manner to give 303 mg of the alcohol.

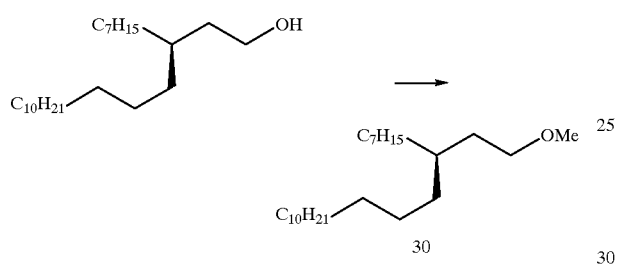

To an ice cold solution of the alcohol (303 mg) in methylene chloride (10 mL) was added triethylamine (150 μL) and mesyl chloride (76 μL). After 4 hours, the reaction was worked up in the usual manner to give 352 mg.

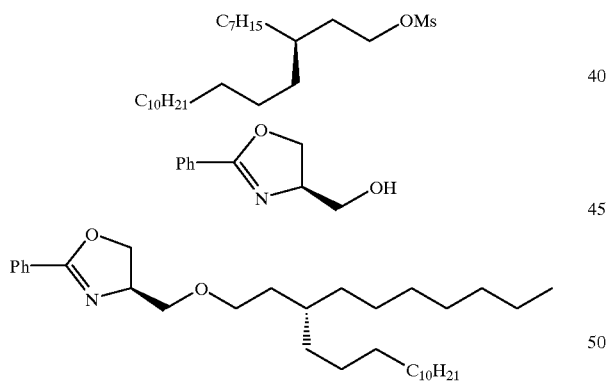

To a solution of the oxazoline (1 mL) in ice cold THF (5 mL) was added potassium t-butoxide solution (2.2 mL of 1M). After 30 minutes, the mesylate was added in THF (5 mL) and the mixture stirred for 8 hours. The usual work-up gave 318.5 mg.

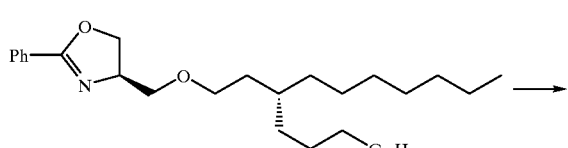

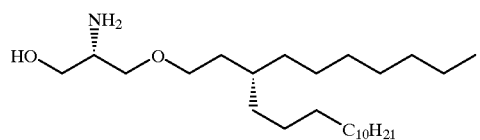

A solution of the oxazoline in methanol (8 mL) and hydrochloric acid (4 mL of 4M) was warmed to 50° C. for 90 minutes. Additional methanol was added and the solvent removed. The residue was dissolved in methanol (8 mL) and sodium hydroxide solution (4 mL) and briefly warmed to 50° C. The mixture was cooled and extracted with chloroform. The usual work-up gave 114 mg.

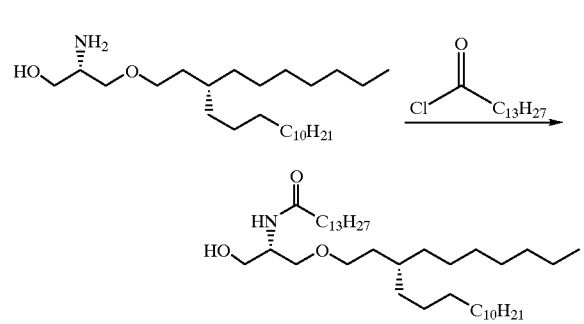

To a solution of the amine (114 mg) in THF (2 mL) and saturated aqueous sodium bicarbonate (2 mL) was added the acid chloride. After 30 minutes additional acid chloride was added. After 30 minutes, the reaction was worked up in the usual manner to give 146 mg.

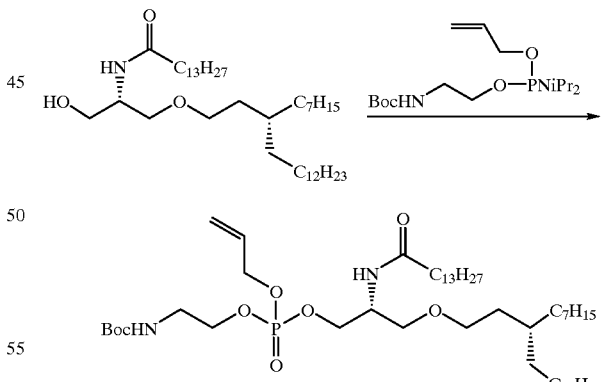

To a solution of tetrazole (48 mg), the phosphorylating reagent (122 mg) in ice cold methylene chloride (2 mL) was added the alcohol (146 mg). Oxone (230 mg) in water (1 mL) and THF (2 mL) was added. After 90 minutes, thiosulfate was used to quench the reaction. Standard work up gave 140 mg.

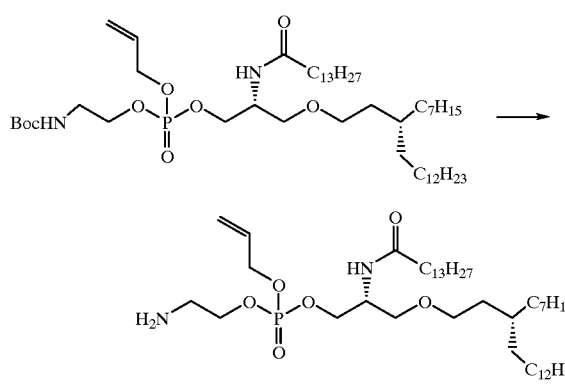

To a solution of the substrate in ice cold methylene chloride was added triethylsilane (370 μL) and trifluoroacetic acid (110 μL). After 5 minutes, the volatiles were removed to give 148 mg.

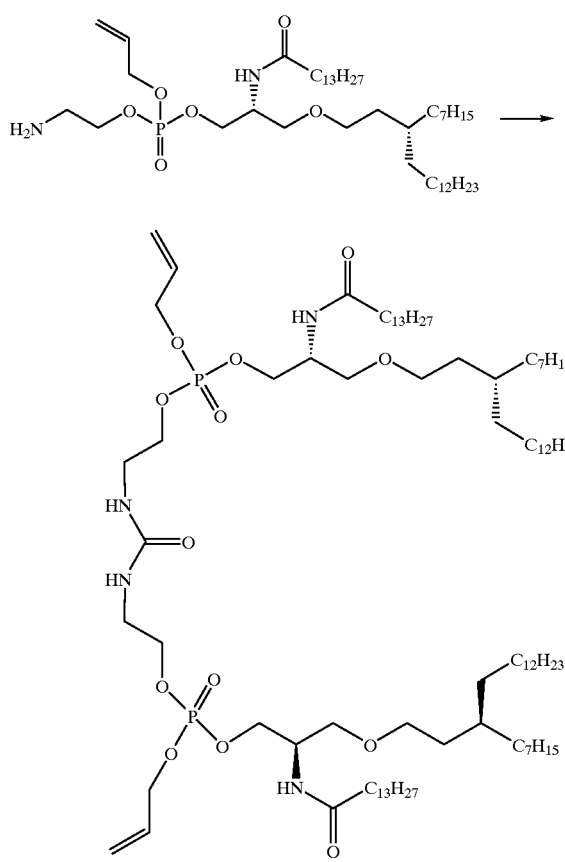

To a solution of the amine (66.9 mg) in ice cold methylene chloride (0.8 mL) was added saturated aqueous sodium bicarbonate (0.8 mL) and phosgene solution (20 μL of 1.93 M). After one hour, additional phosgene (10 μL) was added. After 30 minutes, the usual work-up gave 47.7 mg.

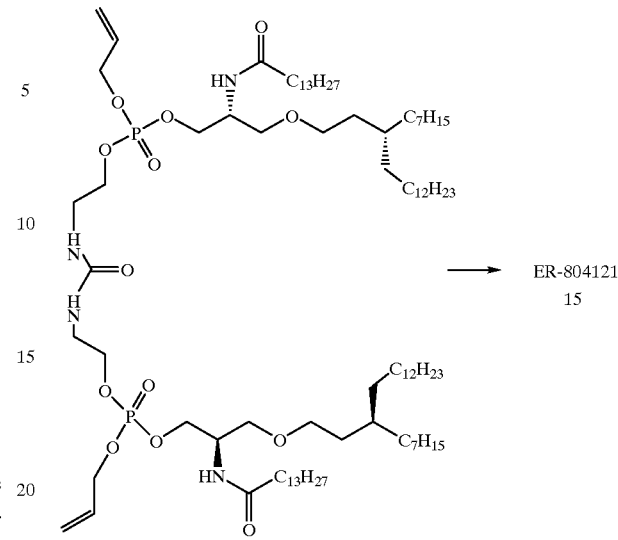

To a solution of phenylsilane (15 uL), tetrakis (triphenylphosphine) palladium [0] (24.8 mg) in ice cold chloroform under an inert atmosphere was added the substrate. After 5 minutes, the mixture was applied to a DEAE column and chromatographed to give 31 mg of ER-804130.

Preparation of ER-804558

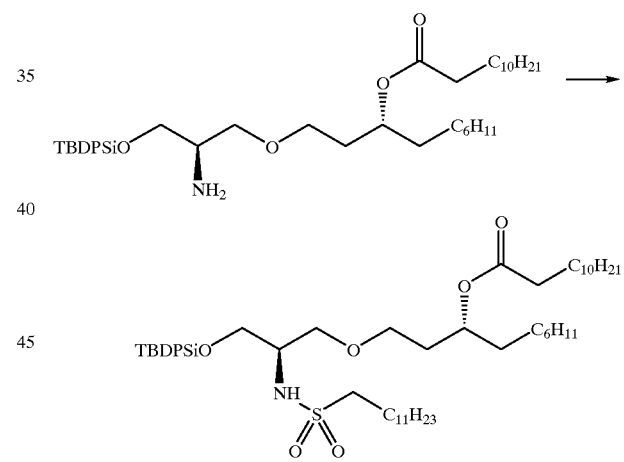

To a solution of the amine (325 mg) in methylene chloride was added triethylamine (321 μL) and 1-dodecanesulfonyl chloride. After 3 hours, the usual work up gave 384 mg.

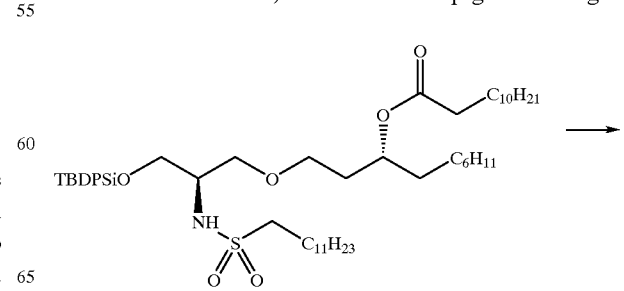

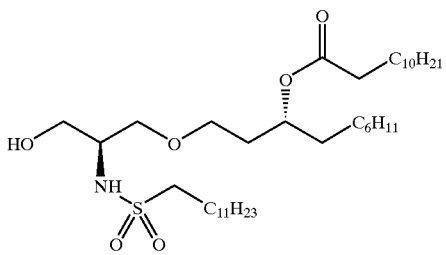

To a solution of the protected alcohol (3 84 mg) in THF (4 mL) was added tetrabutylammonium fluoride (123 mg) and acetic acid (29 µL). After 2 hours, the usual work up gave 180 mg.

The remainder of the synthesis was completed as outlined above for other compounds of the present invention, i.e. phosphorylating, deblocking, coupling with phosgene, and deprotecting with phenylsilane and palladium.

Preparation of ER-804442

The diol amine was mono-protected as its t-butyl-diphenylsilylether outlined above.

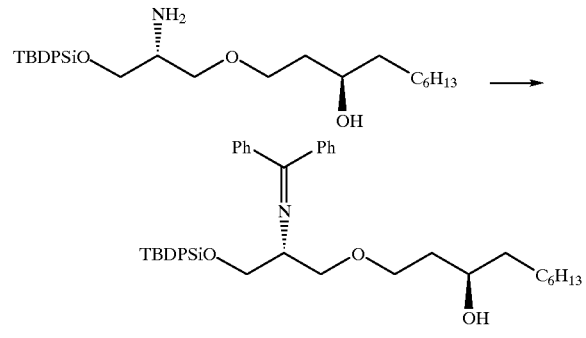

The amine (2.6 g) and benzophenone imine (1.1 mL) were mixed and heated to 40° C. for 4 days to give after chromatography 3.3 g:

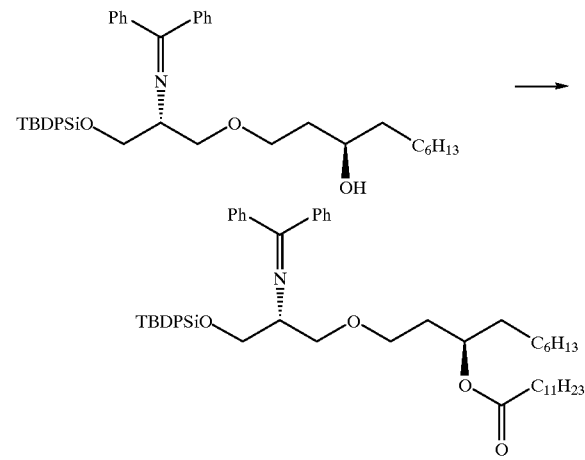

To a solution of the imine (3.3 g) was in ice cold methylene chloride was added lauric acid (1.5 g), EDC (1.7 g) and DMAP (155 mg). The next day, the reaction was worked up in the usual manner to give 3.15 g.

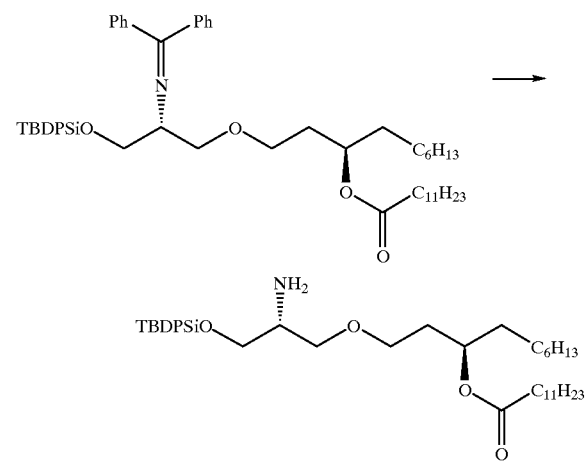

To a solution of the imine (3.14 g) in ether was added 1 N aqueous hydrochloric acid. The next day, the reaction was worked up in the usual manner to give 2.81 g.

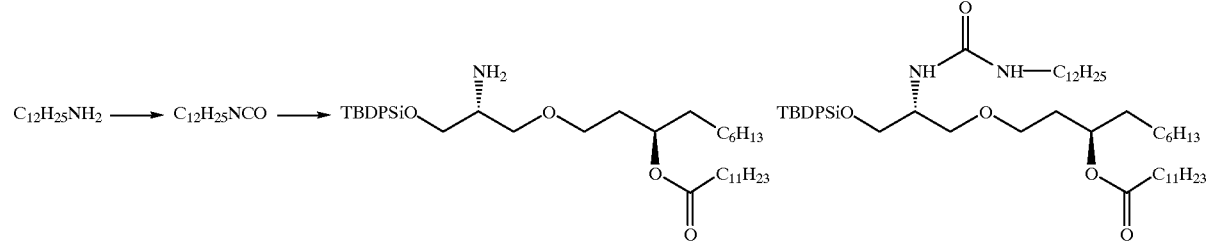

To a solution of trichloromethylchloroformate (12 µL) in ice cold methylene chloride (250 µL) was added dodecylamine (18 μL) and diisopropylethylamine (27 μL). After 30 minutes, the solvent was removed. The residue was dissolved in ice cold methylene chloride, to which was added the amine (55.6 mg) and additional diisopropylethylamine (13 μL). After 2 hours, the usual work up gave, after chromatography, 60.9 mg.

This product was de-protected with fluoride, phosphorylated, de-protected with TFA, dimerized with phosgene, and un-blocked with phenylsilane and palladium as outlined above to give ER-804442.

Preparation of ER-804221

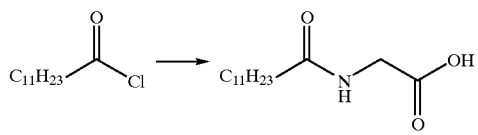

To an ice cold solution of glycine (8.26 g) in aqueous sodium hydroxide (4.4 g in 60 mL) was added lauroyl chloride (21.8 g). After 1 hour, acid was added and the mixture worked up in the usual way. Recrystallization from ethyl acetate gave 9.7 g.

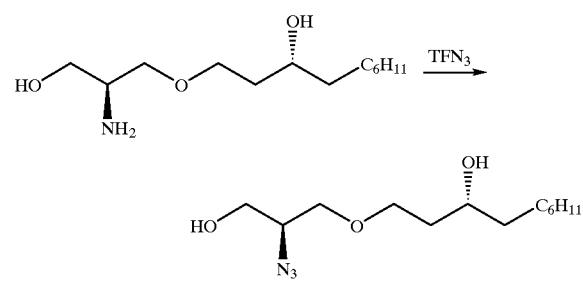

To an ice cold solution of the amine (1.4 g) in methanol was added triflic azide (20 mg). The next day, additional azide was added. After 2 hours, the reaction was worked up in the usual manner to give after chromatography 1.14 g.

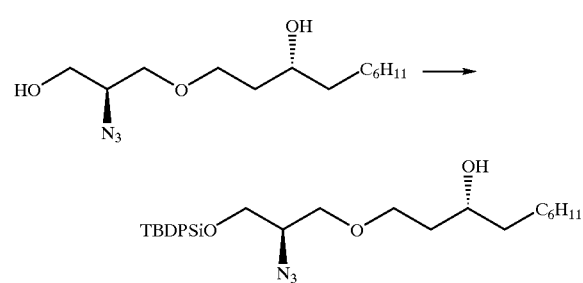

To a solution of the alcohol (1.14 g) in methylene chloride was added t-butyldiphenylsilyl chloride (1.09 mL), triethylamine (1.8 mL) and DMAP (50 mg). After 3 hours, the usual work up gave 1.4 g.

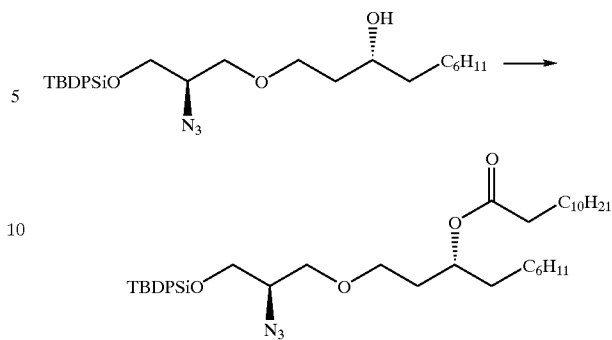

To a solution of the alcohol (1.4 g) in ice cold methylene chloride was added lauric acid (826 mg), EDC (1.05 g) and DMAP (33 mg). The next day, the usual work up gave after chromatography 778 mg.

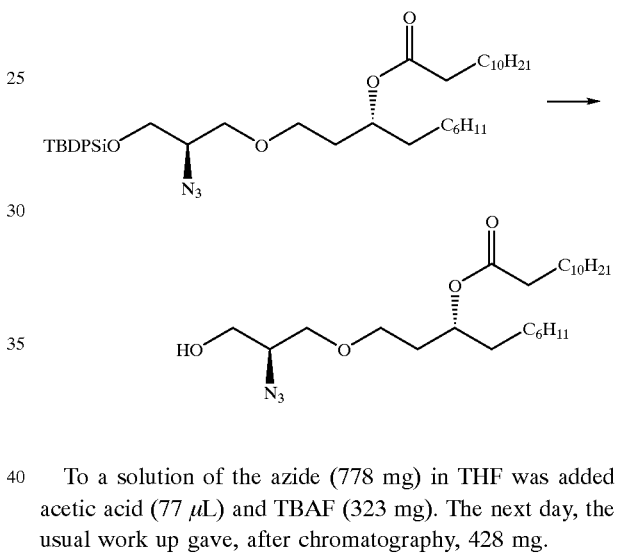

To a solution of the azide (778 mg) in THF was added acetic acid (77 μL) and TBAF (323 mg). The next day, the usual work up gave, after chromatography, 428 mg.

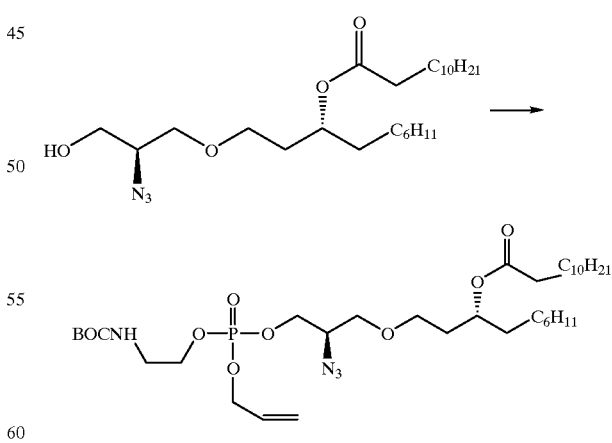

To a solution of the azide (460 mg) in methylene chloride was added tetrazole (165 mg), the phosphorylating reagent (390 mg), and after 30 minutes, oxone in water (722 mg in 3 mL). The reaction was quenched with thiosulfate. Usual work up, after chromatography, gave 392 mg.

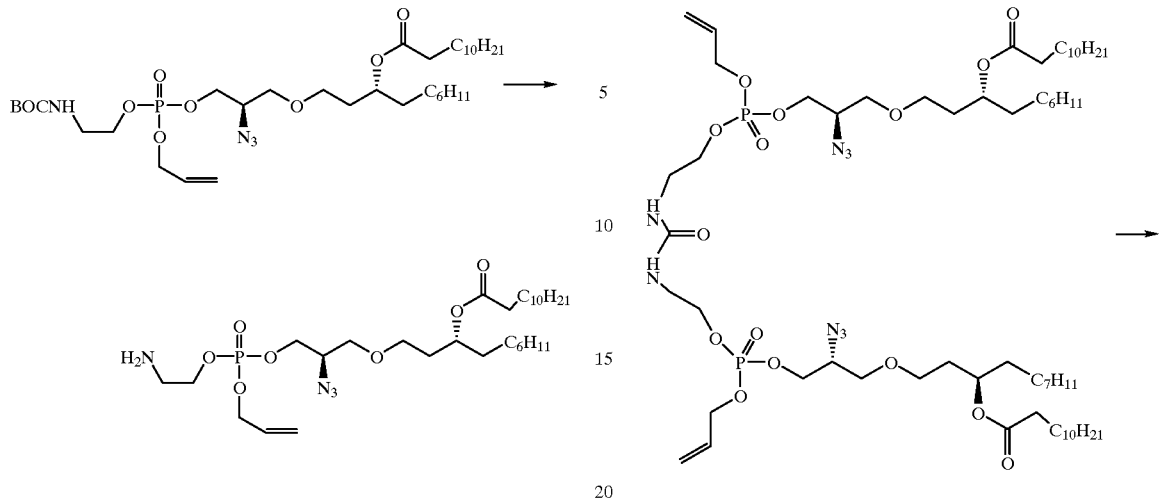

The protected amine (460 mg) was dissolved in methylene chloride and trifluoroacetic acid (394 μL) and triethylsilane (308 EL). After 1.5 hour, the usual work up gave, 392 mg.

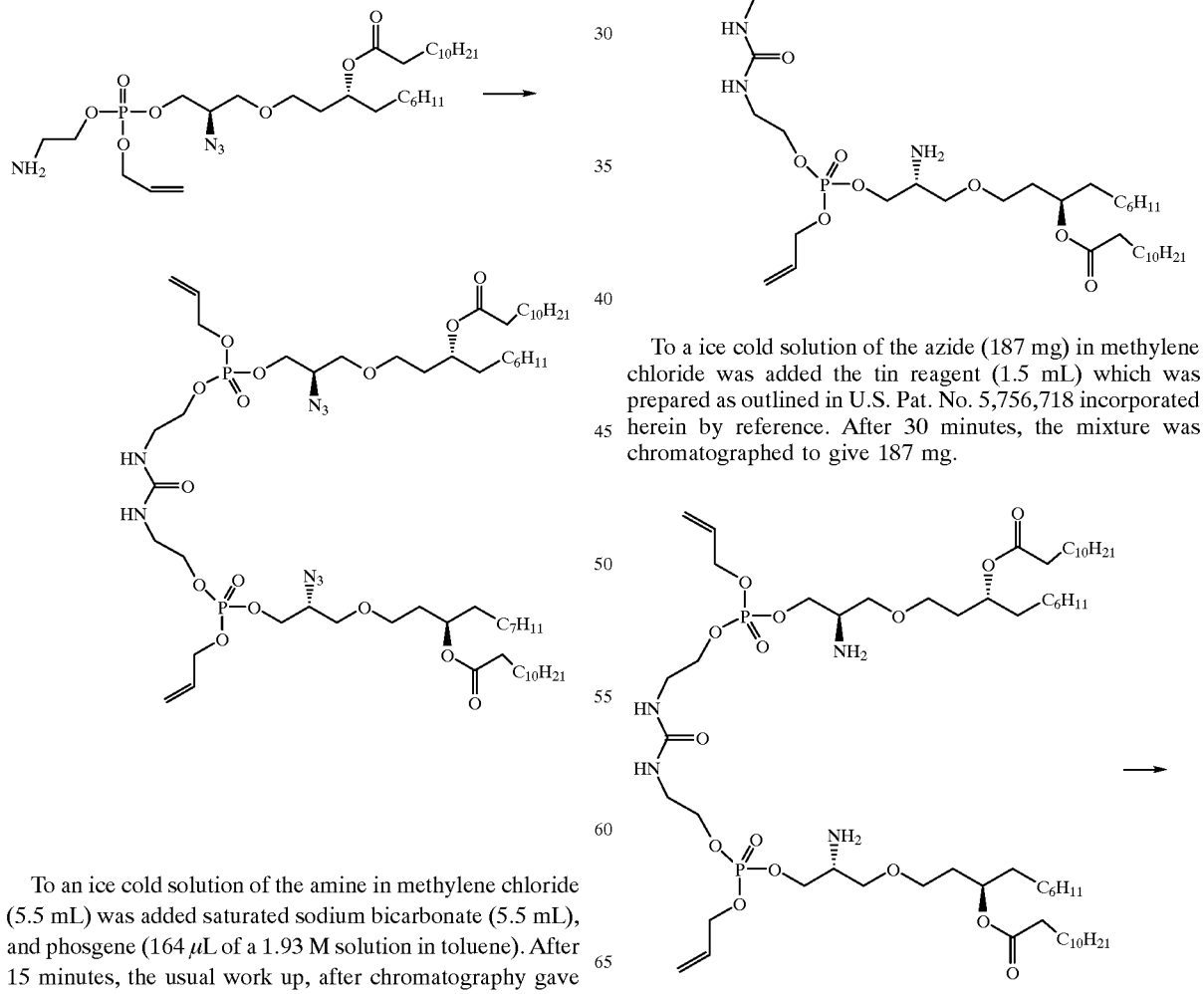

To an ice cold solution of the amine in methylene chloride (5.5 mL) was added saturated sodium bicarbonate (5.5 mL), and phosgene (164 μL of a 1.93 M solution in toluene). After 15 minutes, the usual work up, after chromatography gave 342 mg.

To a ice cold solution of the azide (187 mg) in methylene chloride was added the tin reagent (1.5 mL) which was prepared as outlined in U.S. Pat. No. 5,756,718 incorporated herein by reference. After 30 minutes, the mixture was chromatographed to give 187 mg.

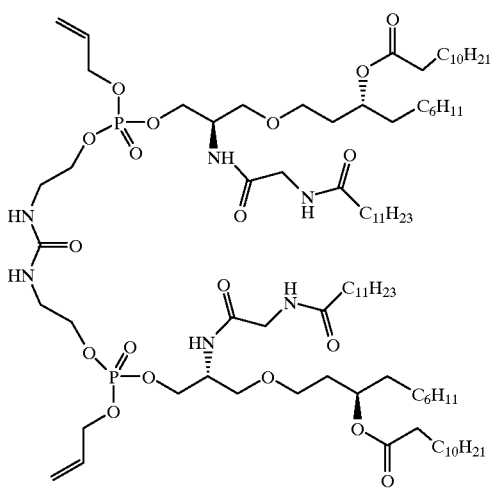

To a ice cold solution of the urea (55 mg) in methylene chloride was added the acid (59 mg) (prepared as above) and EDC (44 mg). The next day, additional EDC (5 mg) and acid (5 mg) was added. After 2 hours, the normal work up provided 45.7 mg.

Normal removal of the protecting groups with phenylsilane and palladium gave ER-804221.

ER-804222 was prepared in a similar manner except that the condensation product between lauryl chloride and glycine, 1 5-methylmyristic acid was used.

Preparation of ER-804281

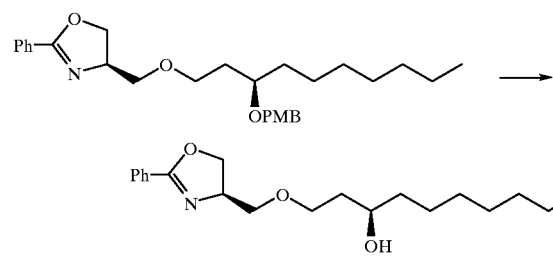

To a ice cold solution of the protected alcohol (8.3 g) in acetonitrile: water was added CAN (41.4 g). After 1 hour, the usual work up gave 5.7 g.

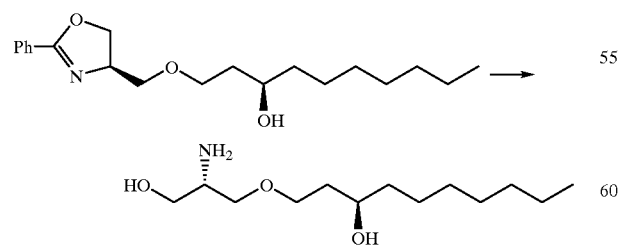

A solution of the alcohol (5.63 g) in 4 N HCl solution was heated to reflux for 1 hour, cooled, neutralized with sodium hydroxide and worked up in the usual manner to give

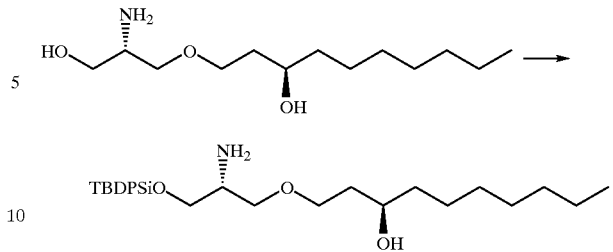

To an ice cold solution of the alcohol (2.2 g) in methylene chloride was added imidazole (0.7 g), t-butyl-diphenylsilyl chloride in 15 mL of methylene chloride. The next day, the usual work up gave 1.54 g.

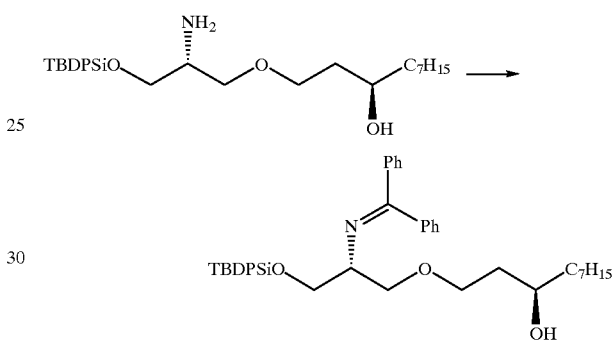

To a solution of the alcohol (1.93 g) in methylene chloride (40 mL) was added benzophenone imine (0.8 mL). After 1 day, the mixture was heated to reflux overnight. The usual work up gave 1.67 g.

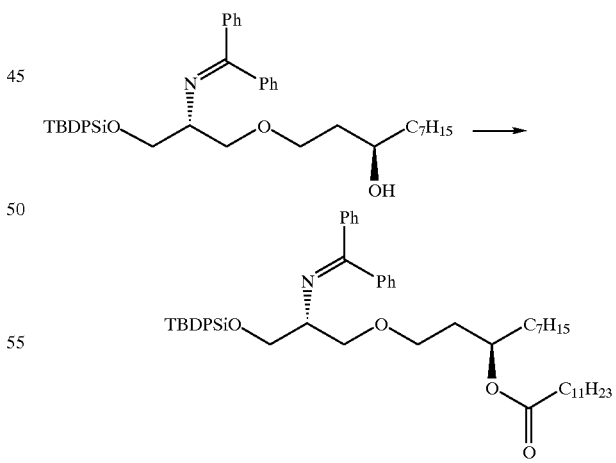

To an ice cold solution of the alcohol (1.67 g) in methylene chloride was added DMAP (159 mg), EDC (0.99 g) and lauric acid (1.04 g). After one day, the usual work up gave 74% yield.

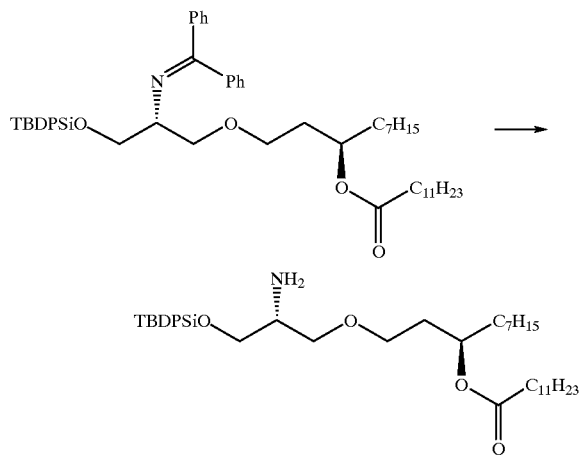

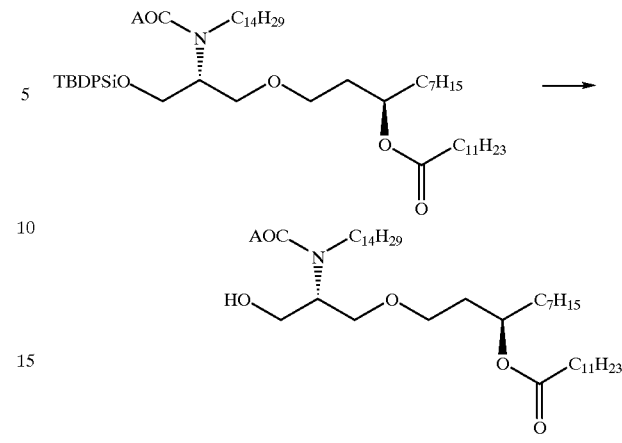

To an ice cold solution of the imine (2.9 g) in ether (50 mL) was added 1 N HCl (50 mL). The next day, the usual work up gave 2.09 g.

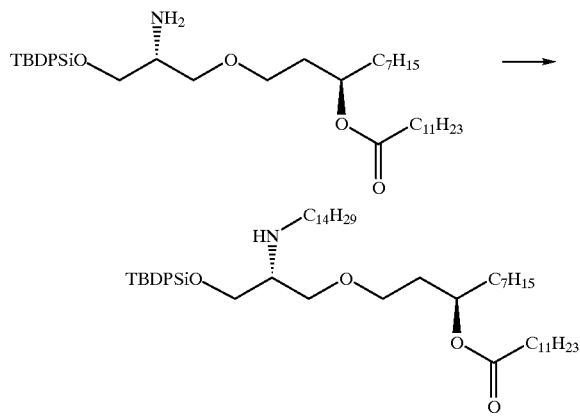

To a solution of the amine (1.24 g) in dichloroethane was added sodium cyanoborohydride (178 mg) and tetradecanal (411 mg). The next day, the usual work up gave 1.5 g.

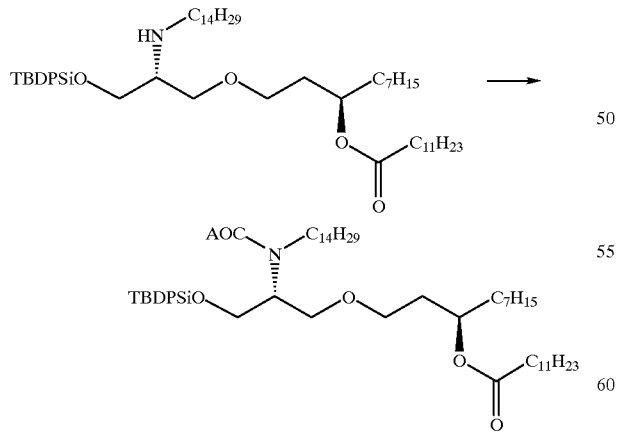

To a ice cold solution of the amine (221 mg) in dioxane was added allyl chloroformate (40 mg) and 308 µL of 1 N NaOH solution. After 2 hours, the usual work up gave 200 mg.

To an ice cold solution of the protected alcohol (365 mg) in THF was added TBAF (1924 µL) and acetic acid (122 µL). The next day, the usual work up gave 271 mg. This material was phosphorylated, deblocked with TFA, dimerized with phosgene and the allyl protecting groups removed with phenylsilane and palladium as described above to give ER-804281.

Preparation of ER-804339

ER-804281→ER-804339

To a ice cold solution of ER-804281 (7 mg) in methylene chloride was added triethylamine (5 µL), DMAP (0.6 mg) and acetyl chloride (1.8 µL). After 4 days, the usual work-up gave 1.1 mg.

Preparation of ER-804674

ER-804281→ER-804674 To a solution of ER-804281 (12.7 mg) in THF (1.0 mL) was added methyl iodide (9.2 mg) and sodium bicarbonate (6.8 mg). The mixture was stirred for 5 days and sodium bicarbonate (14 mg) and additional methyl iodide (8 mL) was added. After an additional 3 days, additional bicarbonate (28 mg) and MeI (16 µL). After an additional 6 days, the mixture was worked up to give 9.1 mg of product.

Preparation of ER-804596

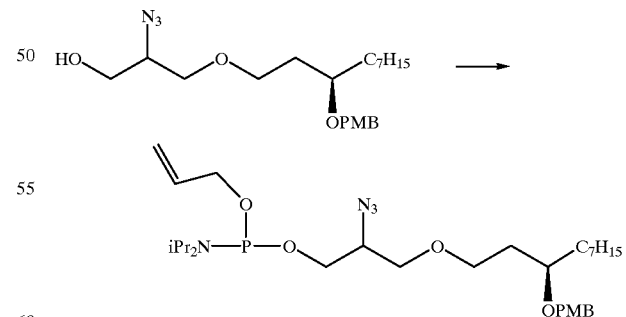

To a solution of the alcohol (393 mg) in methylene chloride (2 mL) was added diisopropylamine (210 µL), tetrazole (105 mg) and phosphorylating reagent (as described above) (488 mg). After 2⅓ hours, the usual work up gave the desired product.

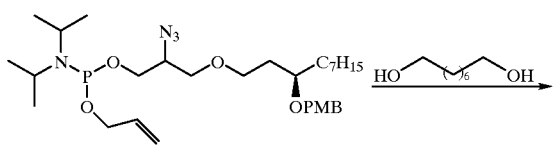

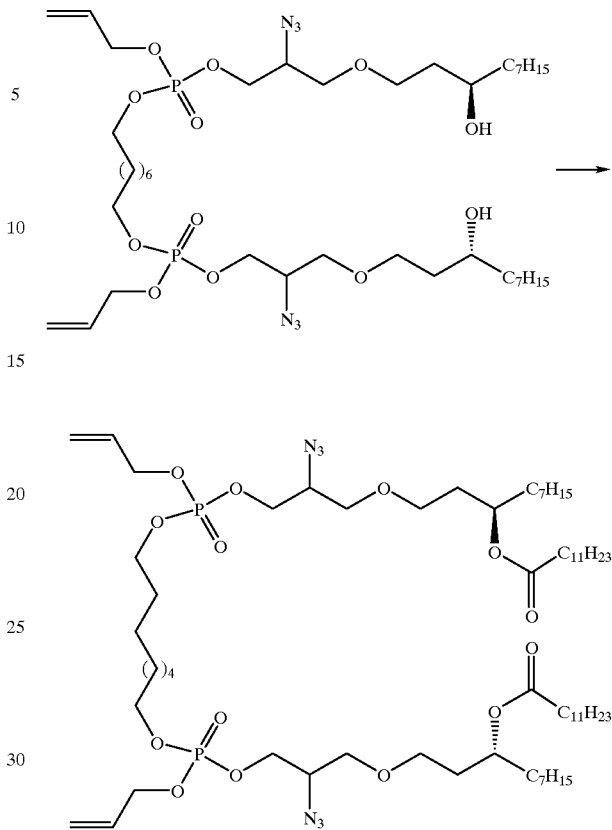

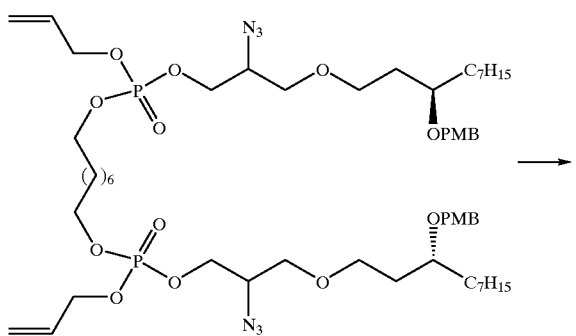

To a solution of the diol (73 mg) in acetonitrile was added tetrazole (175 mg), the azide (1 equivalent). After 3 hours, the mixture was cooled and ozone (1229 mg) added. The next day, usual work up gave the desired product.

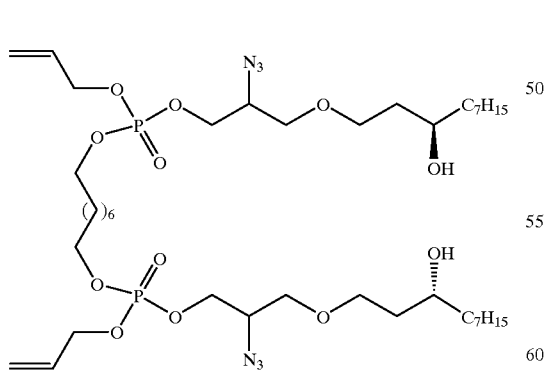

To an ice cold solution of the protected alcohol (92.9 mg) in acetonitrile:water (6 mL: 1.5 mL) was added CAN(358 mg). After 1 hour, the usual work up provided 68.5 mg.

To an ice cold solution of the diol (68.5 mg) in methylene chloride was added lauric acid (76.5 mg), DMAP (4.7 mg) and EDC (73 mg). The next day, the usual work up gave 76.5 mg.

The azides were reduced using the tin reagent described above. The diamine was acylated with dodecanoyl chloride, and the protecting groups removed with phenylsilane and palladium as described above to give ER-804596.

Preparation of ER-804732

The alcohol (7.04 g) was dissolved in methylene chloride (300 mL) with triethylamine (11.13 mL) and then cooled to 0° C. under a nitrogen atmosphere. Methanesulfonyl chloride (3.69 mL) was added dropwise after which time the reaction was stirred at room temperature for 1 hour. The usual work up gave 5.551 g.

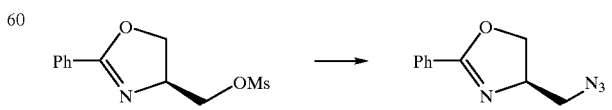

The mesylated (1.114 g) was dissolved in DMF (30 mL) followed by sodium azide (0.9337 g). The reaction mixture was warmed to 57° C. and stirred for 16 hours and then to 104° C. for and additional 3 hours. After cooling to room temperature the mixture was worked up in the usual manner and gave 0.466 g.

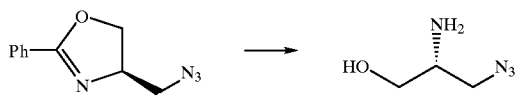

The protected aminoalcohol (0.466 g) was hydrolyzed using 4 N HCl (15 mL) at 107° C. for 3 hours. After cooling to room temperature, the reaction mixture was filtered and extracted with ethyl ether, dried, concentrated and used in the next reaction.

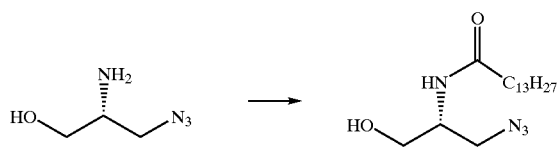

The crude aminoalcohol was dissolved in THF (5 mL) with saturated sodium bicarbonate (6 mL) and cooled to 0° C. Myristoyl chloride (0.79 mL) was added dropwise after which time the reaction was warmed to room temperature and stirred for 2 hours. The reaction mixture was worked up using the usual methods and gave 0.751 g.

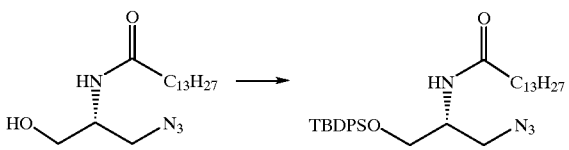

The alcohol (0.185 g) was dissolved in DMF (3.0 mL) with imidazole (0.077 g) and tert-butyldiphenylsilyl chloride (0.197 mL). The reaction mixture was stirred at room temperature for 16 hours after which time the usual work up gave 0.320 g.

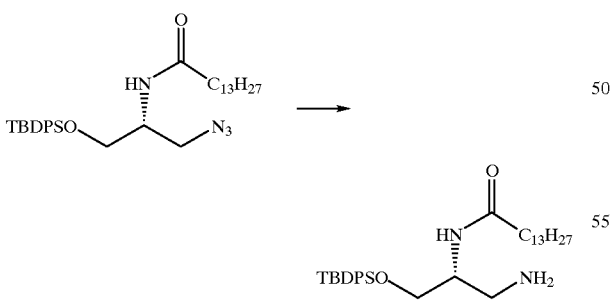

The azide (0.975 g) was dissolved in methanol (20 mL) with 10% palladium on carbon (0.180 g). The mixture was stirred under an atmosphere of hydrogen gas under atmospheric pressure for 2 hours after which time the gas was evacuated and the mixture filtered over Celite 545 and concentrated. Purification using the usual methods gave 0.873 g.

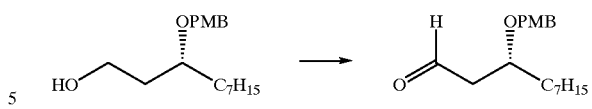

DMSO (1.5 mL) was added dropwise to oxalyl chloride (0.92 mL) in methylene chloride (30 mL) at 78° C. After stirring for 15 minutes the alcohol (1.727 g) in methylene chloride (30 mL) was added dropwise and stirred for an additional 30 minutes. Triethylamine (4.90 mL) was added dropwise, the reaction was warmed to 0° C. and quenched using saturated ammonium chloride. Purification of the crude product using silica gel chromatography with 20% ethyl acetate in hexanes gave 1.653 g.

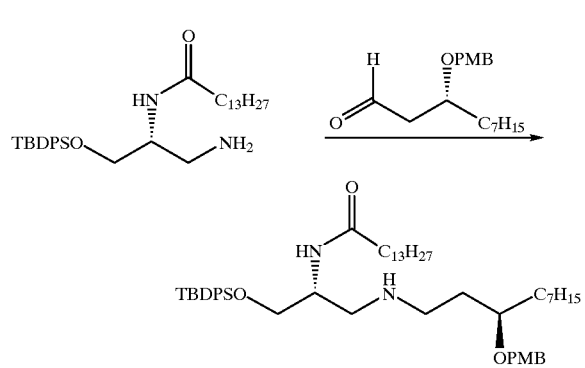

The primary amine (0.135 g) and aldehyde (0.077 g) were dissolved in 1,2-dichloroethane (5 mL) followed by the addition of sodium cyanoborohydride (0.032 g). The reaction was stirred for 20 hours after which time acetic acid (0.02 mL) was added and the reaction worked up in the usual manner to give 0.103 g.

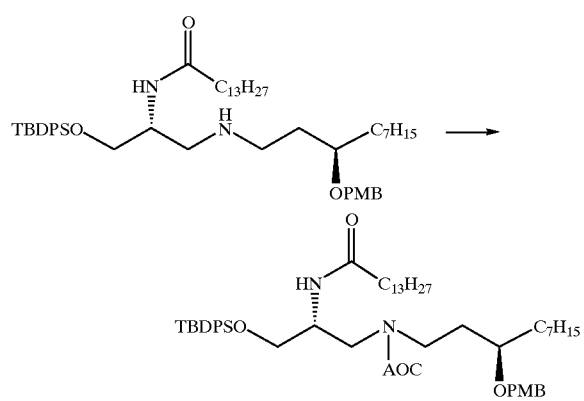

The secondary amine was dissolved in 1,4-dioxane (15 mL) and cooled to 0° C. followed by the slow addition of 1 M sodium hydroxide (3.0 mL). After stirring for 10 minutes allyl chloroformate (0.236 mL) was added dropwise after which time the reaction was warmed to room temperature and stirred for 16 hours. Work up in the usual manner gave 0.613 g.

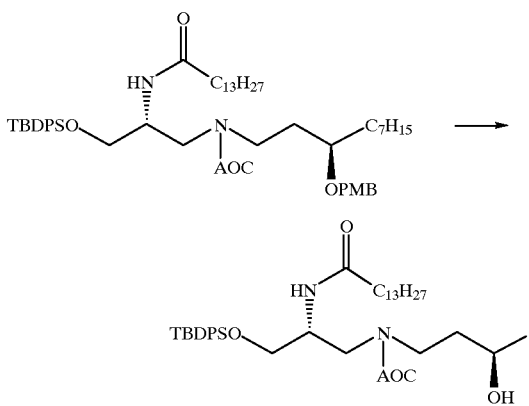

The para-methoxybenzyl ether (0.613 g) was dissolved in a 4 to 1 ratio of acetonitrile to water (15 mL), cooled to 0° C. and then CAN (1.525 g) was added. The reaction mixture was stirred at 0° C. for 2 hours and then worked up in the usual manner to give 0.357 g.

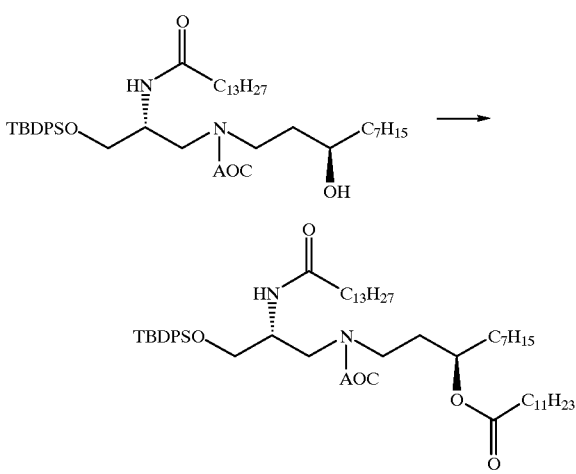

The alcohol (0.357 g) was dissolved in methylene chloride (5 mL) with lauric acid (0.184 g), EDC (0.175 g) and cooled to 0° C. 4-Dimethylaminopyridine (0.012 g) was added and the resulting mixture was stirred at room temperature for 2 hours. Work up in the usual manner gave 0.436 g.

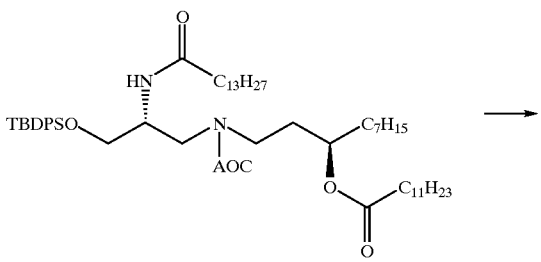

-continued

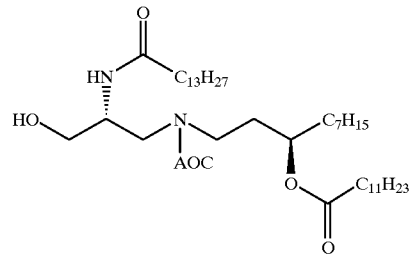

The silyl protected alcohol (0.211 g) was dissolved in THF (5 mL) with acetic acid (0.03 mL). Tetrabutylammonium fluoride (0.115 g) was added in one portion and the reaction mixture was stirred at room temperature for 16 hours. A normal work up gave 0.150 g.

This material was phosphorylated, deblocked with TFA, dimerized with phosgene and the allyl protecting groups removed with phenylsilane and palladium as descried above to give ER-804732.

Preparation of ER-804680

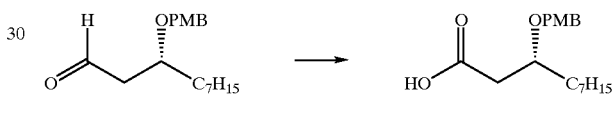

The aldehyde (1.54 g) was dissolved in THF (28 mL) and cooled to 0° C. after which time 2-methyl-2-butene (14 mL) and tert-butyl alcohol (28 mL) was added. A stirred suspension of sodium chlorite (3.70 g) and sodium trihydrogen phosphate (4.09 g) in water (42.7 mL) was added to the above mixture and stirred at 0° C. for 1.5 hours. The completed reaction was diluted with ethyl acetate (100 mL) and washed with 10% sodium bisulfite, brine, dried, concentrated and silica gel chromatographed to give 1.55 g.

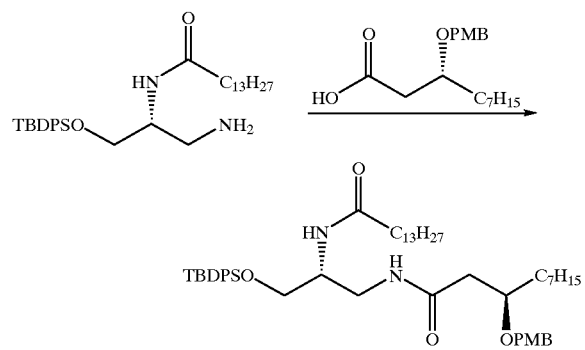

The amine (0.553 g) and acid (0.381 g) were mixed in methylene chloride (8 mL) and cooled to 0° C. after which time EDC (0.230 g) was added and the reaction mixture was stirred at room temperature for 72 hours. The usual work up gave 0.567 g.

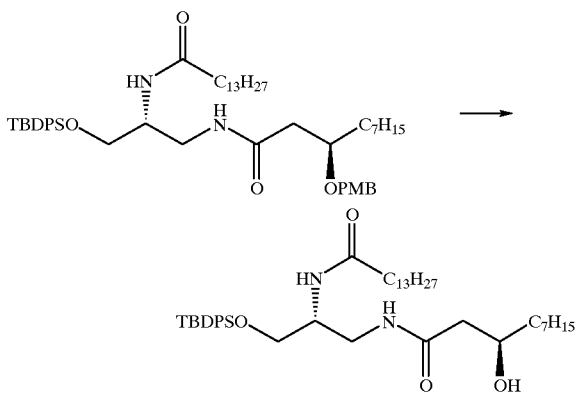

The methoxybenzyl ether (0.567 g) was dissolved in a 1 to 1 ratio of acetonitrile to water (16 mL) with methylene chloride (8 mL) and cooled to 0° C. CAN (1.53 g) was added and the reaction mixture was stirred for 1 hour after which time it was worked up in the usual manner to give the crude alcohol.

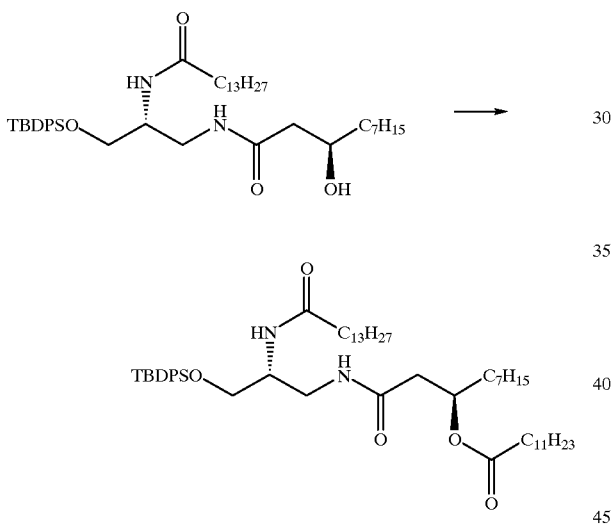

The crude alcohol from above was dissolved in methylene chloride (15 mL) with lauric acid (0.280 g) and 4 dimethylaminopyridine (0.017 g). The reaction mixture was cooled to 0° C. and EDC (0.267 g) was added in one portion after which time the reaction mixture was warmed to room temperature and stirred for 16 hours. Normal work up procedures provided 0.622 g.

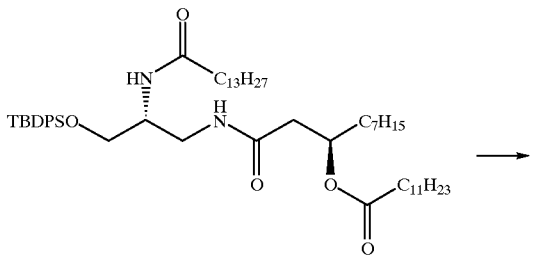

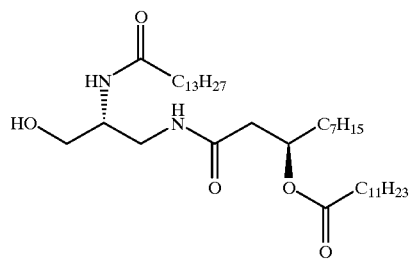

The silyl ether (0.563 g) was dissolved in THF (10 mL) with acetic acid (0.087 mL). Tert-butylammonium fluoride (0.330 g) was added and the reaction was stirred at room temperature for 16 hours. Work up in the usual manner gave 0.384 g.

This material was phosphorylated, deblocked with TFA, dimerized with phosgene and the allyl protecting groups removed with phenylsilane and palladium as described above to give ER-804780.

Preparation of ER-804679

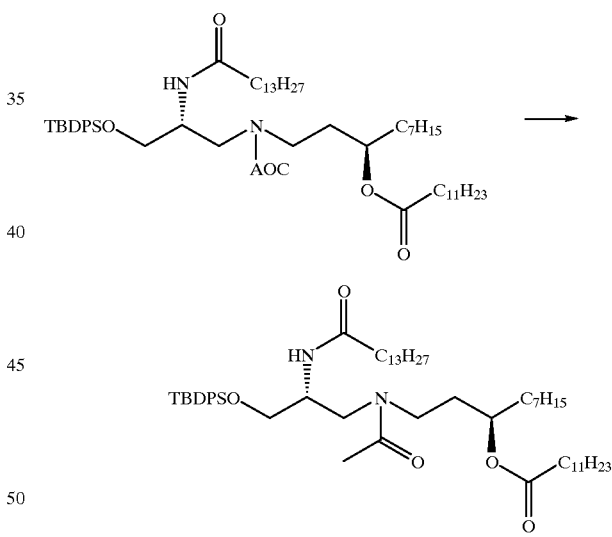

The protected secondary amine (0.071 g) was dissolved in degassed chloroform (3 mL) with phenylsilane (0.017 mL) and acetic anhydride (0.014 mL). The reaction mixture was cooled to 0° C. followed by the addition of tetrakistriphenylphosphine palladium (0) (0.002 g). The reaction mixture was warmed to room temperature and allowed to stir for 30 minutes. The completed reaction was diluted with methylene chloride, washed with water, dried, concentrated, and chromatographed to give 0.068 g.

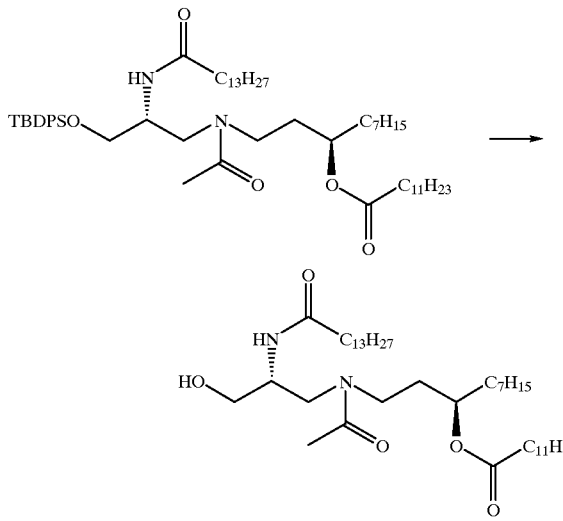

The silyl ether was deprotected in THF (5 mL) with acetic acid (0.025 mL) with the addition of tert-butylammonium fluoride (0.092 g). After stirring at room temperature for 16 hours the reaction was worked up in the usual manner to give 0.120 g.

This material was phosphorylated, deblocked with TFA, dimerized with phosgene and the allyl protecting groups removed with phenylsilane and palladium as described above to give ER-804679.

Preparation of ER-804764

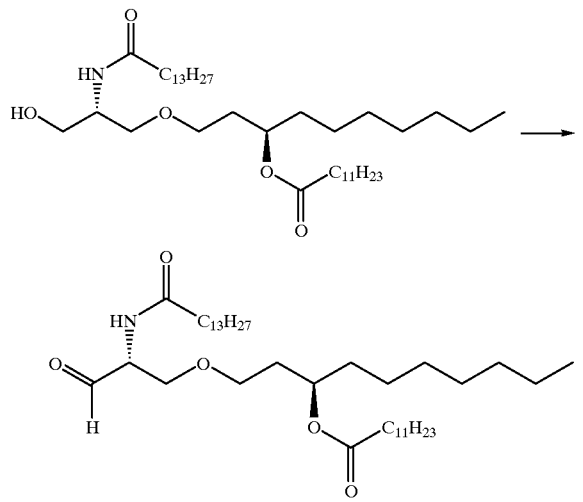

DMSO (0.33 mL) was added dropwise to oxalyl chloride (0.203 mL) in methylene chloride (10 mL) at 78° C. After stirring for 15 minutes the alcohol (0.993 g) in methylene chloride (3 mL) was added dropwise and stirred for an additional 30 minutes. Triethylamine (1.08 mL) was added dropwise, the reaction was warmed to 0° C. and quenched using saturated ammonium chloride. Purification of the crude product using silica gel chromatography with 20% ethyl acetate in hexanes gave 0.743 g.

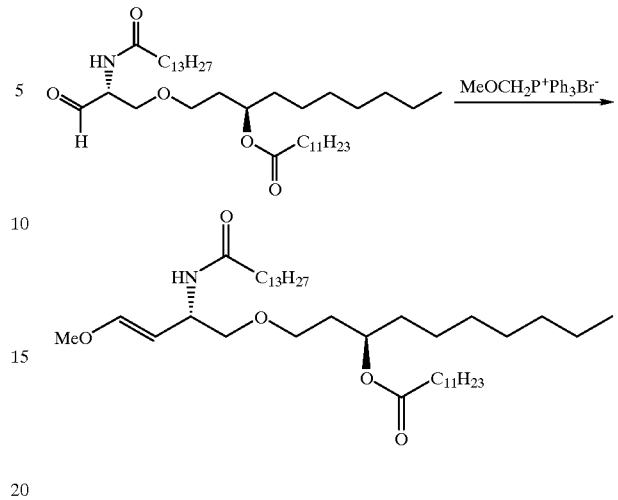

The 1.6 M n-butyl lithium in hexanes (1.5 mL) was added dropwise to the phosphonium salt (0.797 g) in THF (10 mL) at 0° C. After stirring for 30 minutes the aldehyde (0.734 g) in THF (15 mL) was added dropwise. After stirring at room temperature for one hour the reaction was worked up in the usual manner to give 0.193 g.

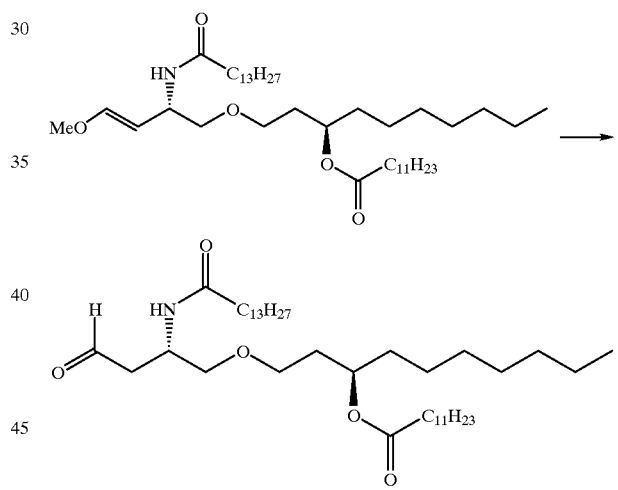

The enol ether (0.193 g) was hydrolyzed with 57% hydrogen iodide (0.114 L) in acetonitrile (2 mL). After stirring at room temperature for 2 hours the reaction was quenched with saturated sodium bicarbonate, extracted with methylene chloride, and dried to give 0.211 g crude aldehyde.

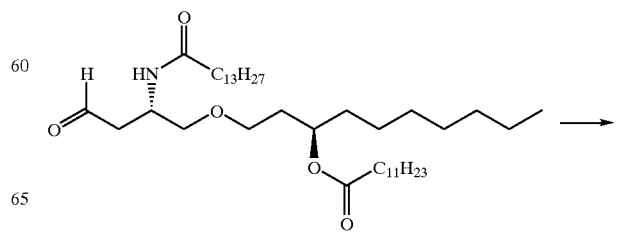

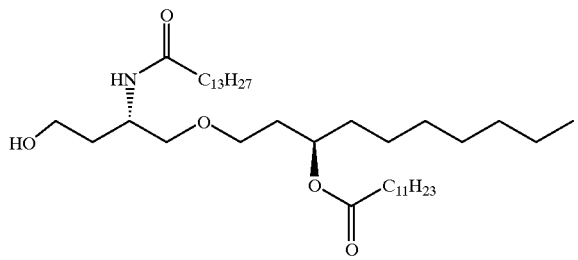

The crude aldehyde (0.211 g) was dissolved in methanol (3 mL) and sodium borohydride (0.033 g) was added at 0° C. After stirring for 30 minutes the reaction was diluted with water, extracted with methylene chloride, dried, concentrated and purified by silica gel chromatography to give 0.148 g.

This material was phosphorylated, deblocked with TFA, dimerized with phosgene and the allyl protecting groups removed with phenylsilane and palladium as described above to give ER-804764.

Preparation of ER-804772

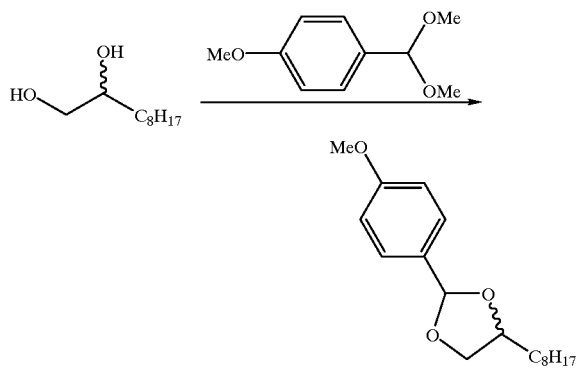

The commercially available diol (1.486 g) was mixed with the acetal (1.864 g) and para-toluenesulfonic acid (0.195 g) in DMF (10 mL). After stirring for 20 hours at room temperature under a nitrogen atmosphere, the reaction was quenched with sat. sodium bicarbonate, extracted with methylene chloride, dried and concentrated via high vacuum. Silica gel chromatography of the resultant crude product using 10% ethyl acetate in hexanes gave 2.084 g.

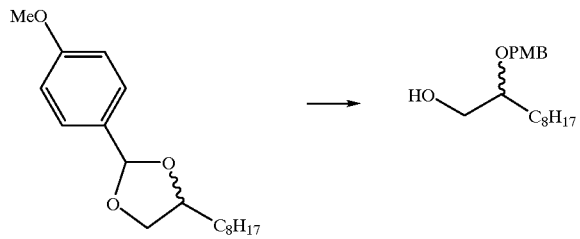

The acetal (2.084 g) was cooled to 78° C. under a nitrogen atmosphere in methylene chloride (30 mL) followed by the dropwise addition of 1.0 M DIBAL in hexanes (14.3 mL). After additional DIBAL (14 mL) was added, the reaction mixture was stirred for 1 hour, warmed to room temperature and quenched with sodium, potassium tartarate. The normal work up gave 2.1 g.

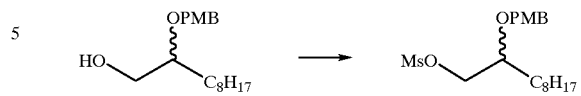

The alcohol (1.286 g) was mixed with triethylamine (0.883 g) in methylene chloride (15 mL) and cooled to 0° C. Methanesulfonyl chloride (0.575 g) was added dropwise followed by stirring for 20 minutes at 0° C. and room temperature for 2 hours. The normal work up gave 1.496 g.

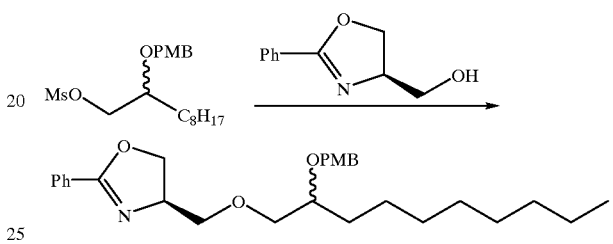

The alcohol (1.495 g) in DMF (10 mL) was added dropwise to a stirring suspension of washed 60% sodium hydride (0.257 g) in DMF (20 mL) at 0° C. After stirring for 3 hours the mesylate (0.925 g) in DMF (10 mL) was added dropwise. After stirring for an additional 3 days, the reaction was quenched and worked up in the usual manner gave 0.905 g.

As with examples provided above, the para-methoxybenzyl protecting group was hydrolyzed with CAN, the protected amino alcohol hydrolyzed using aqueous HCl then KOH, acylation of the amine with tetradecanoyl chloride, silylation of the primary alcohol with TBDPS, acylation of the secondary alcohol with dodecanoyl chloride, and hydrolysis of the silyl protecting group using TBAF to give the primary alcohol. This material was phosphorylated, deblocked with TFA, dimerized with phosgene and the allyl protecting groups removed with phenylsilane and palladium as described above to give ER-804772.

Preparation of ER-804947

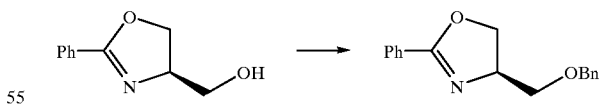

The alcohol (0.263 g) in THF (5 mL) was added dropwise to washed 60% sodium hydride (0.216 g) in DMF (2.0 mL) at room temperature under a nitrogen atmosphere. The reaction mixture was stirred for 30 minutes after which time benzyl bromide (0.272 mL) with a catalytic amount (0.05 g) of tetrabutylammonium iodide. The final reaction mixture was stirred for an additional hour after which time the mixture was quenched and worked up in the usual manner to give 0.365 g.

The protected aminoalcohol (0.189 g) was hydrolyzed using 4 N hydrochloric acid (2.5 mL) followed by 40% sodium hydroxide (2.5 mL) as described previously to provide 0.121 g.

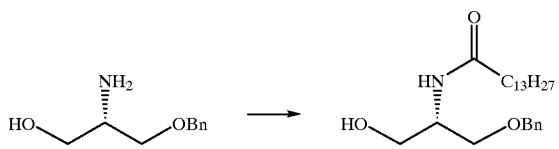

The aminoalcohol (0.121 g) was dissolved in methylene chloride (2 mL) with saturated sodium bicarbonate (2 mL). After cooling to 0° C., myristoyl chloride (0.199 mL) was added dropwise. After continued stirring for 2 hours the mixture was worked up in the usual manner and gave 0.181 g.

The alcohol (0.181 g) was dissolved in methylene chloride (5 mL) with the acid (0.180 g) and 1-[3-(dimethylamino)propyl]-3-ethylcarbodiimide (EDC 0.133 g). The mixture was cooled to 0° C. and 4-dimethylaminopyridine was added follow by stirring for 16 hours at room temperature. The usual work up gave 0.310 g.

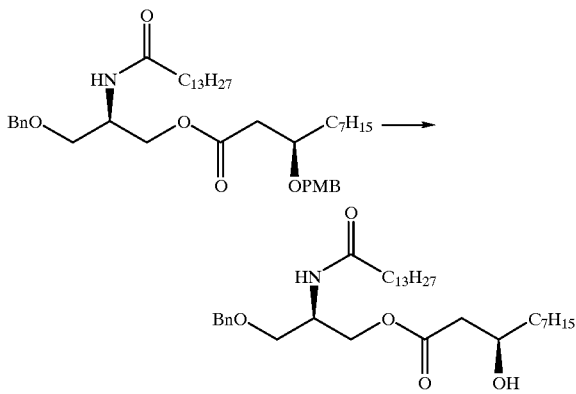

The para-methoxybenzyl ether (0.305 g) was dissolved in acetonitrile (8 mL) with water (2 mL) and cooled to 0° C. Cerium ammonium nitrate (1.110 g) was added and the reaction mixture was stirred for 2 hours after which time using the normal work up gave crude alcohol.

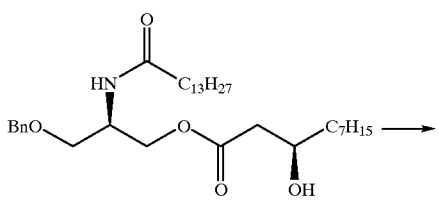

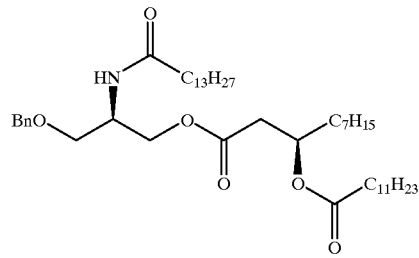

The crude alcohol was dissolved in methylene chloride (8 mL) with lauric acid (0.126 g) and 4-dimethylaminopyridine (0.011 g). After cooling to 0° C., EDC (0.119 g) was added and the mixture was stiffed at room temperature for 16 hours. The usual work up gave 0.355 g.

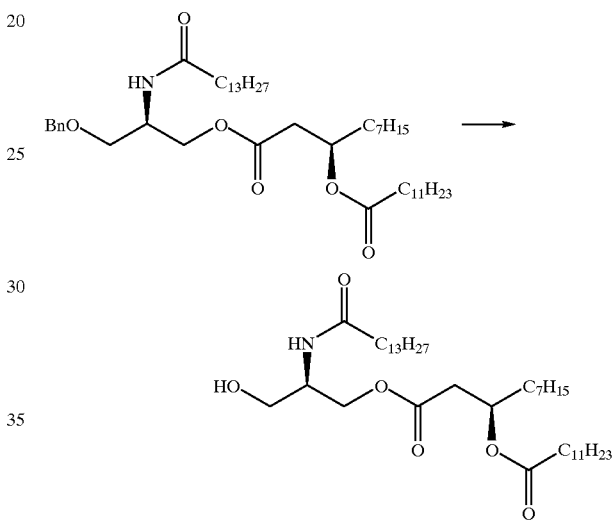

The benzyl ether (0.355 g) was dissolved in ethyl acetate (50 mL) with palladium hydroxide (0.048 g) and acetic acid (0.25 mL). The reaction mixture was placed under 50 psi of a hydrogen atmosphere and shaken for 10 hours. Work up in the usual manner gave 0.255 g.

This material was phosphorylated, deblocked with TFA, dimerized with phosgene and the allyl protecting groups removed with phenylsilane and palladium as described abovetogive ER-804947.

BIOLOGICAL EXAMPLES

Example 7

Induction of Cytokines (In Vitro)

There are no validated in vitro assays that can be used as an indicator of adjuvant activity.

However, the inability of a molecule to trigger any stimulatory response in macrophages is a strong indication that it is not likely to be an immunoadjuvant. For this reason, the ability of compounds to stimulate release of TNF-alpha and other cytokines from immune cells may be indicative of their ability to stimulate an immune response which may result in adjuvant activity.

E. Assays in Human Whole Blood

The most readily available human system to test compound activity on monocytes/macrophages is in whole blood. Various concentrations of compounds of the invention were added as 10× stocks in 50 µl of $Ca^{++}$, $Mg^{++}$ free Hank's balanced salt solution (HBSS) followed by 50 µl of HBSS into 400 µl of heparinized whole blood obtained from normal volunteers (18–51 years old; 110–230 lb.) into the wells of plastic assay plates, for a total volume of 500 µl/well (final concentration of whole blood was 80%). After a 3-hour -15 incubation with gentle shaking at 37° C. in a 5% $CO_2$ atmosphere, the assay plates were centrifuged at 1000×g for 10 min. at 4° C. and plasma was drawn off and frozen at −80° C. Plasma samples were analyzed for TNF-alpha by ELISA (Genzyme Corp., Cambridge, Mass.). Each assay point was tested in triplicate.

As shown in FIG. 1, compounds such as 100, 184 and 186 stimulate blood-borne cells to release TNF-alpha. This stimulatory activity can be compared to that of 10 ng/ml endotoxin (or LPS) present in similar incubations in the same assay. As shown in Table 1, activity of compounds (tested at 10 µM) ranges from inactive (such as compound 110) to compounds demonstrating greater activity than the LPS standard.

B. Cultured human cell lines

Figure 2:
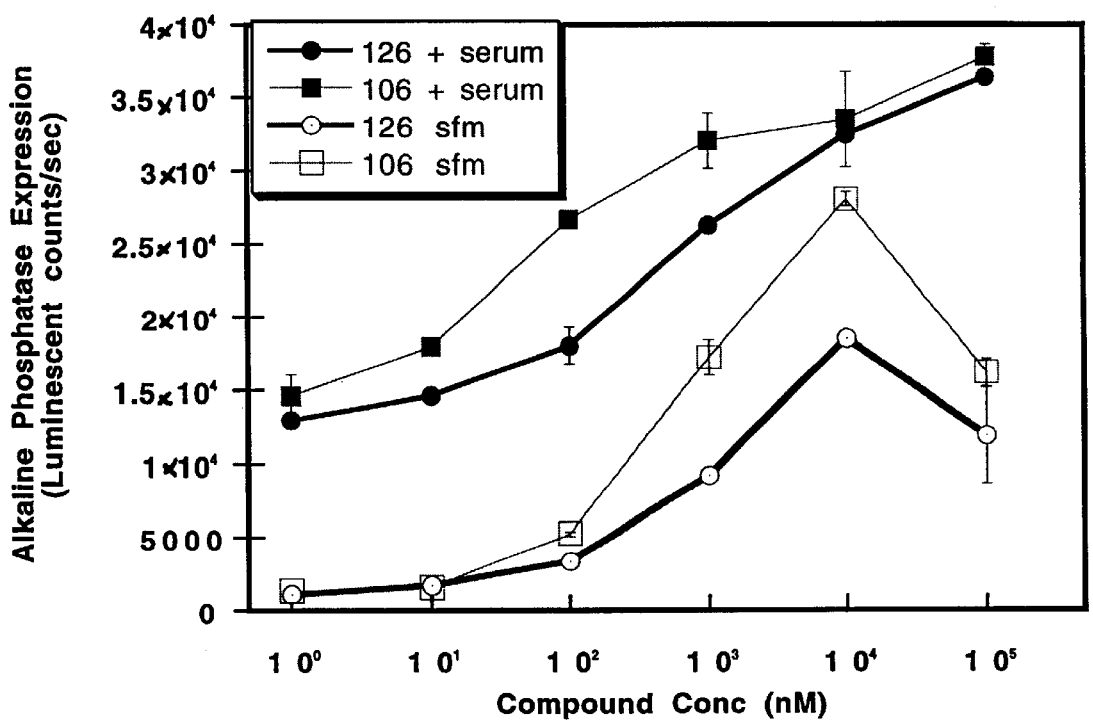
FIG. 2 is a graph that shows stimulation of alkaline phosphatase expression from an inducible reporter construct with the TNF promoter (TNF-PLAP) in THP-1 cells by compounds 106 and 126 in the absence and presence of 10% serum.

Similar results can be obtained when compounds of the invention are tested in a cell-culture model. In this assay, compounds of the invention are tested for their ability to stimulate secretion of alkaline phosphatase from THP-1 cells that have been transfected with the gene for secreted alkaline phosphatase under the control of the TNF-alpha promoter, as described in detail in Goto et al., Molecular Pharmacology 49; 860–873 (1996). In this assay, however, the effects of removing serum[1]—a condition that may more-likely mimic a subcutaneous environment—can be evaluated. As shown in FIG. 2 and described in Table 1, results from these assays indicate that compounds of the invention stimulate induction of genes under the control of the TNF-alpha promoter when added to cells in the absence as well as the presence of serum.

TABLE 1

Stimulation of cytokine release by compounds in vitro

| ER # | Compound | Whole Blood (% of LPS at 10 µM) | THP-1 cell Stimulation (% of compound 100 at 10 µM)[1] | |
|---|---|---|---|---|
| | MPL Standard | 29[2] | +serum | −serum |
| 112022 | | 131 ± 10.2 (n = 6) | | |

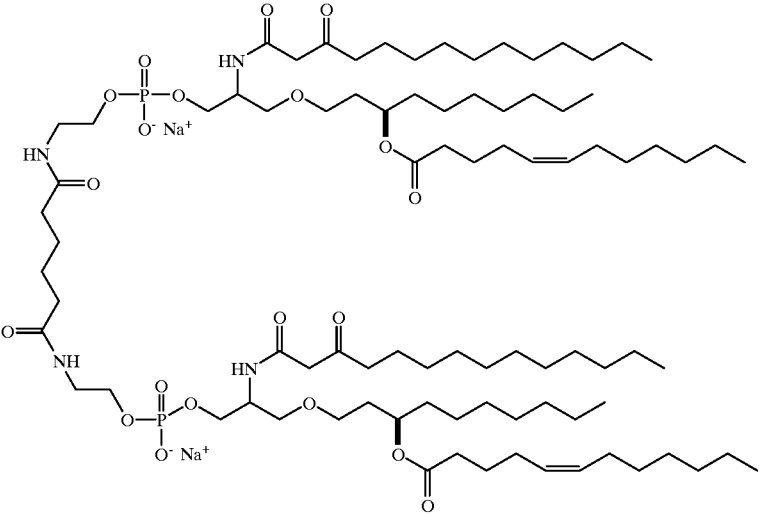

TABLE 1-continued

Stimulation of cytokine release by compounds in vitro

| ER # | Compound<br>MPL Standard | Whole Blood<br>(% of LPS at<br>10 μM)<br>29[2] | THP-1 cell Stimulation<br>(% of compound<br>100 at 10 μM)[1] | |
|---|---|---|---|---|
| | | | +serum | −serum |
| 111230 | | | | 49 |
| 111231 | | | | 17 |

TABLE 1-continued

Stimulation of cytokine release by compounds in vitro

| ER # | Compound<br>MPL Standard | Whole Blood<br>(% of LPS at<br>10 μM)<br>29[2] | THP-1 cell Stimulation<br>(% of compound<br>100 at 10 μM)[1] | |
|---|---|---|---|---|
| | | | +serum | −serum |
| 111232 | [structure] | 158 | 155 | 225 |
| 111233 | [structure] | | 141 | |
| 112043 | [structure] | | 0 | |

TABLE 1-continued

Stimulation of cytokine release by compounds in vitro

| ER # | Compound<br>MPL Standard | Whole Blood<br>(% of LPS at<br>10 μM)<br>29[2] | THP-1 cell Stimulation<br>(% of compound<br>100 at 10 μM)[1] | |
|---|---|---|---|---|
| | | | +serum | −serum |
| 112047 | *(structure)* | 0 | | |
| 112047 | *(structure)* | 0 | | |
| 112048 | *(structure)* | 0 | 24 | |

TABLE 1-continued

Stimulation of cytokine release by compounds in vitro

| ER # | Compound MPL Standard | Whole Blood (% of LPS at 10 μM) 29[2] | THP-1 cell Stimulation (% of compound 100 at 10 μM)[1] +serum | −serum |
|---|---|---|---|---|
| 112049 | | 0 | | |
| 112063 | | 0 | | |
| 112064 | | 50 | | |

TABLE 1-continued

Stimulation of cytokine release by compounds in vitro

| ER # | Compound MPL Standard | Whole Blood (% of LPS at 10 μM) 29[2] | THP-1 cell Stimulation (% of compound 100 at 10 μM)[1] +serum | −serum |
|---|---|---|---|---|
| 112065 | | | | 86 |
| 112066 | | 162 | 330 | |
| 112071 | | | 0 | |

TABLE 1-continued
Stimulation of cytokine release by compounds in vitro
| ER # | Compound<br>MPL Standard | Whole Blood<br>(% of LPS at<br>10 μM)<br>29[2] | THP-1 cell Stimulation<br>(% of compound<br>100 at 10 μM)[1] | |
|---|---|---|---|---|
| | | | +serum | −serum |
| 112072 | 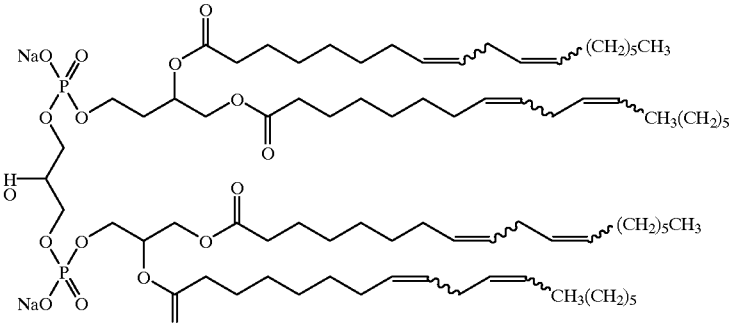 | 0 | | |
| 112091 | 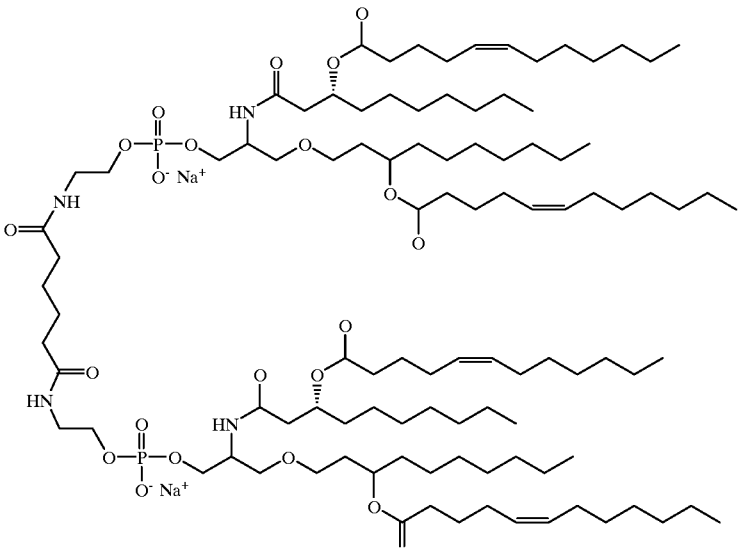 | 0 | | |
| 112092 | 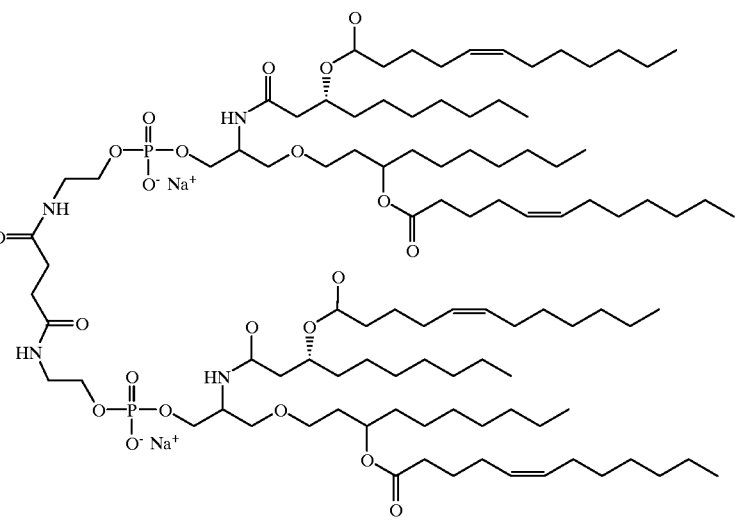 | 0 | | |

TABLE 1-continued
Stimulation of cytokine release by compounds in vitro
| ER # | Compound MPL Standard | Whole Blood (% of LPS at 10 μM) | THP-1 cell Stimulation (% of compound 100 at 10 μM)[1] | |
|---|---|---|---|---|
| | | 29[2] | +serum | −serum |
| 112093 | 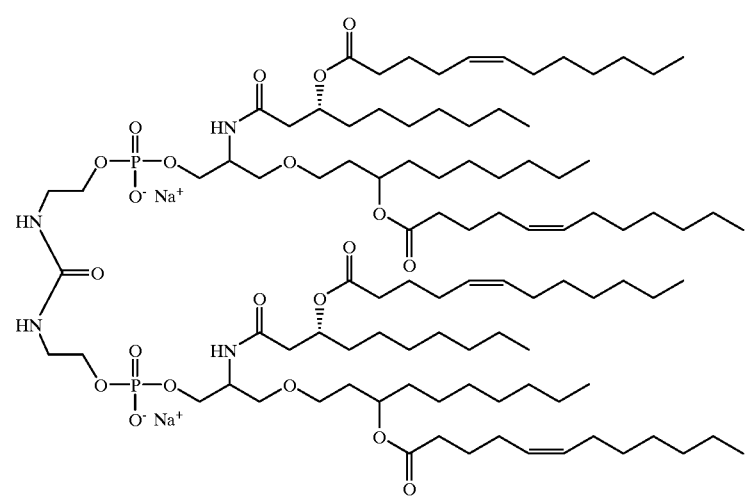 | 0 | | |
| 112098 | 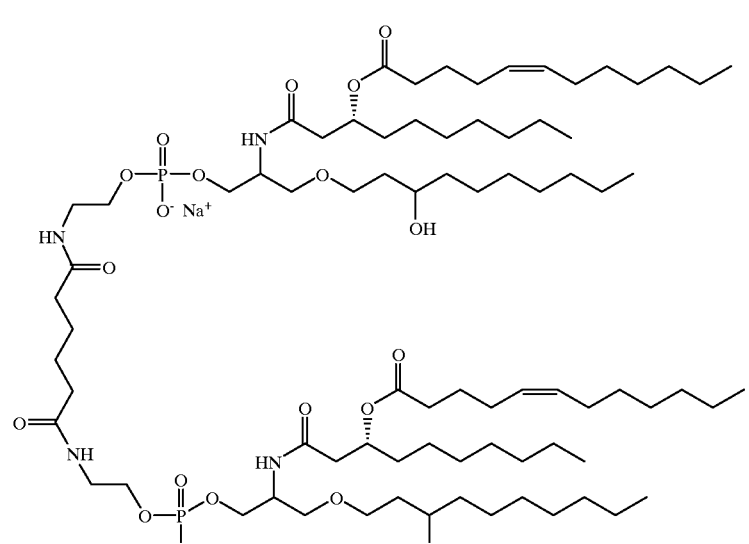 | 0 | | |

TABLE 1-continued
Stimulation of cytokine release by compounds in vitro
| ER # | Compound MPL Standard | Whole Blood (% of LPS at 10 μM) 29[2] | THP-1 cell Stimulation (% of compound 100 at 10 μM)[1] +serum −serum |
|---|---|---|---|
| 112049 | 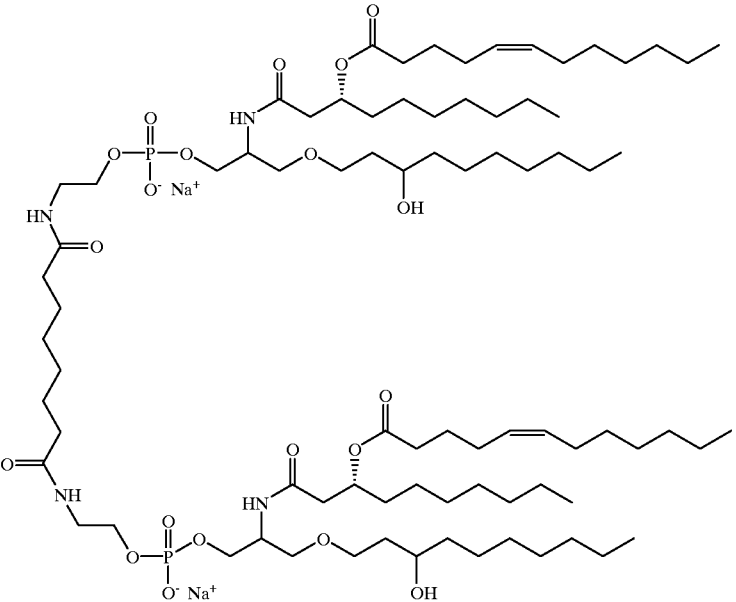 | 0 | |
| 112100 | 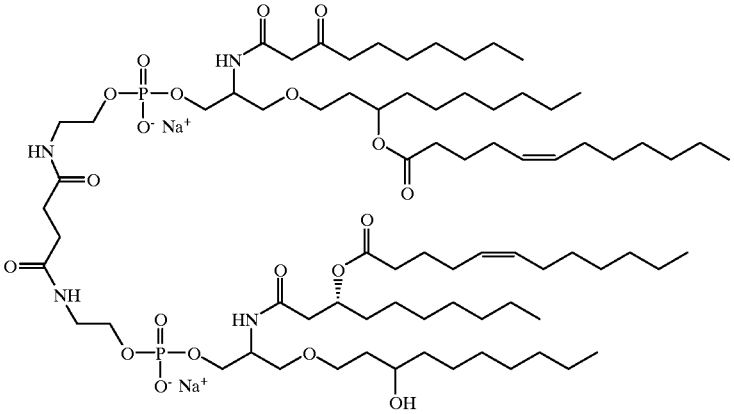 | 0 | |

TABLE 1-continued

Stimulation of cytokine release by compounds in vitro

| ER # | Compound | Whole Blood (% of LPS at 10 μM) | THP-1 cell Stimulation (% of compound 100 at 10 μM)[1] | |
|---|---|---|---|---|
| | MPL Standard | 29[2] | +serum | −serum |
| 112859 | (structure) | 0 | | |
| 112860 | (structure) | 0 | | |

TABLE 1-continued

Stimulation of cytokine release by compounds in vitro

| ER # | Compound<br>MPL Standard | Whole Blood<br>(% of LPS at<br>10 μM)<br>29[2] | THP-1 cell Stimulation<br>(% of compound<br>100 at 10 μM)[1] | |
|---|---|---|---|---|
| | | | +serum | −serum |
| 112861 | [structure] | 0 | | |
| 113634 | [structure] | 0 | | |

TABLE 1-continued

Stimulation of cytokine release by compounds in vitro

| ER # | Compound<br>MPL Standard | Whole Blood<br>(% of LPS at<br>10 μM)<br>29[2] | THP-1 cell Stimulation<br>(% of compound<br>100 at 10 μM)[1] | |
|---|---|---|---|---|
| | | | +serum | −serum |
| 113635 | | 0 | | |
| 113643 | | 0 | | |
| 113644 | | 0 | | |

TABLE 1-continued
Stimulation of cytokine release by compounds in vitro
| ER # | Compound MPL Standard | Whole Blood (% of LPS at 10 μM) 29[2] | THP-1 cell Stimulation (% of compound 100 at 10 μM)[1] +serum | -serum |
|---|---|---|---|---|
| 113651 | 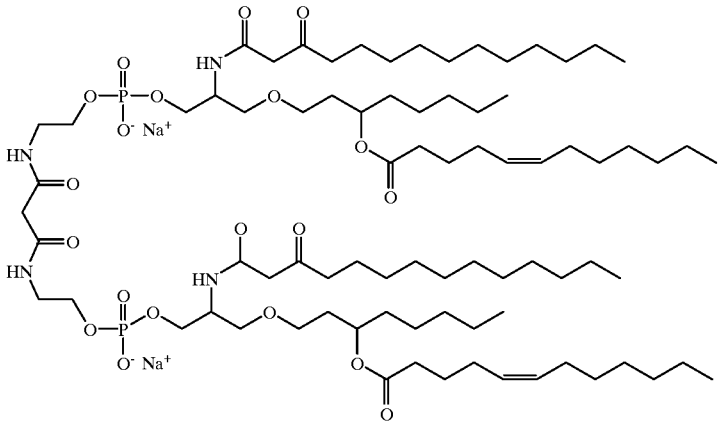 | 133 ± 4.4 (n = 4) | 215 | 254 |
| 113665 | 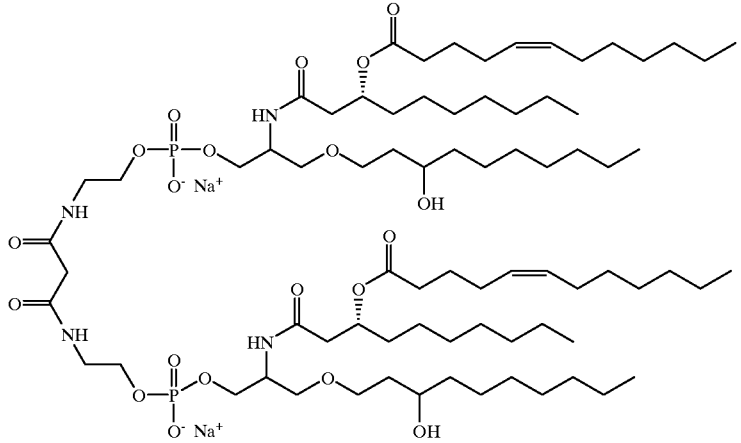 | | | |
| 113666 | 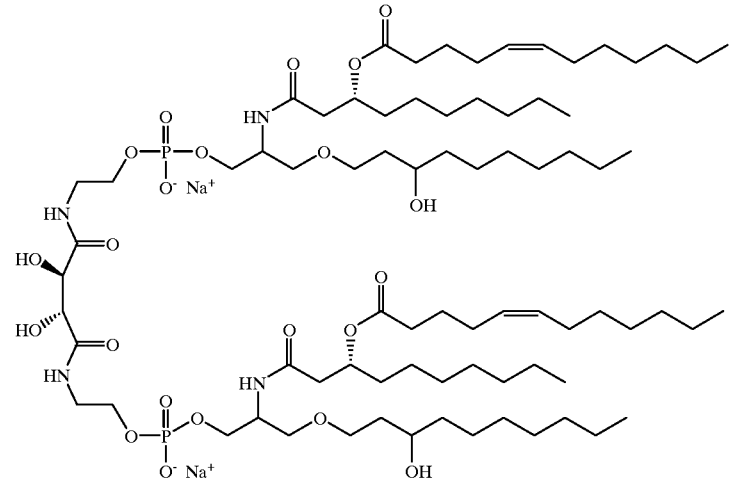 | | | |

TABLE 1-continued
Stimulation of cytokine release by compounds in vitro
| ER # | Compound MPL Standard | Whole Blood (% of LPS at 10 μM) 29[2] | THP-1 cell Stimulation (% of compound 100 at 10 μM)[1] +serum  −serum |
|------|-----------------------|---------------------------------------|------------------------------------------------------------------------|
| 118023 | 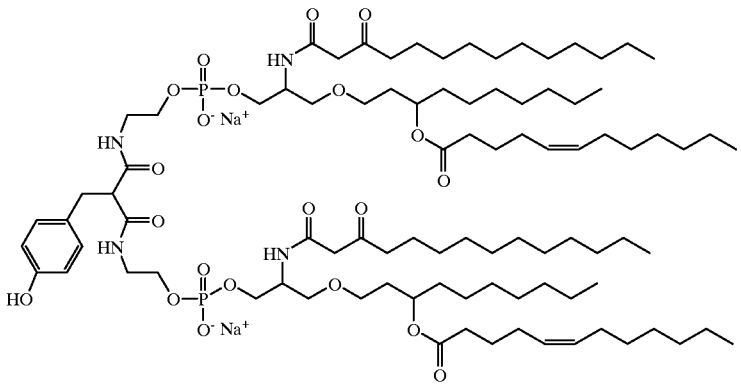 | 63 | |
| 019772 | 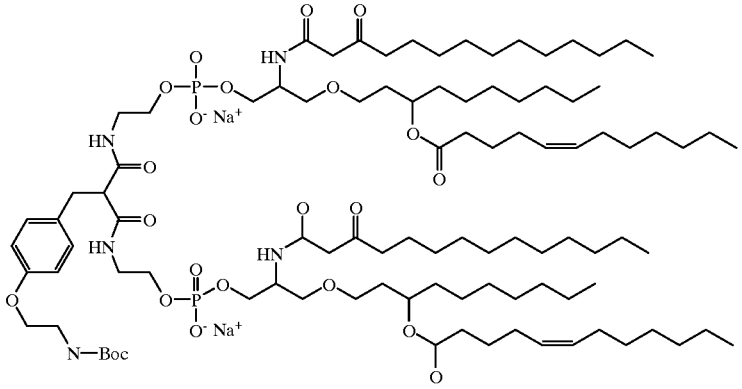 | 69 | |
| 118989 | 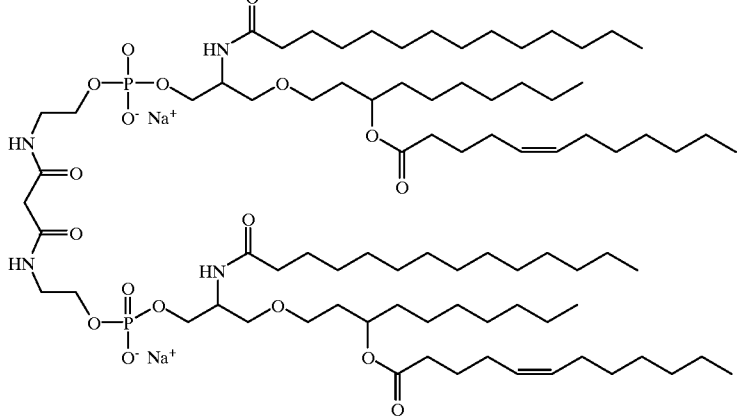 | 159 | |

TABLE 1-continued

Stimulation of cytokine release by compounds in vitro

| ER # | Compound MPL Standard | Whole Blood (% of LPS at 10 μM) 29[2] | THP-1 cell Stimulation (% of compound 100 at 10 μM)[1] +serum | −serum |
|---|---|---|---|---|
| 118999 | | | 105 | |
| 119000 | | | 60 | |
| 119001 | | | 113 | |

TABLE 1-continued
Stimulation of cytokine release by compounds in vitro
| ER # | Compound | Whole Blood (% of LPS at 10 μM) | THP-1 cell Stimulation (% of compound 100 at 10 μM)[1] | |
|---|---|---|---|---|
| | MPL Standard | 29[2] | +serum | −serum |
| 118949 | 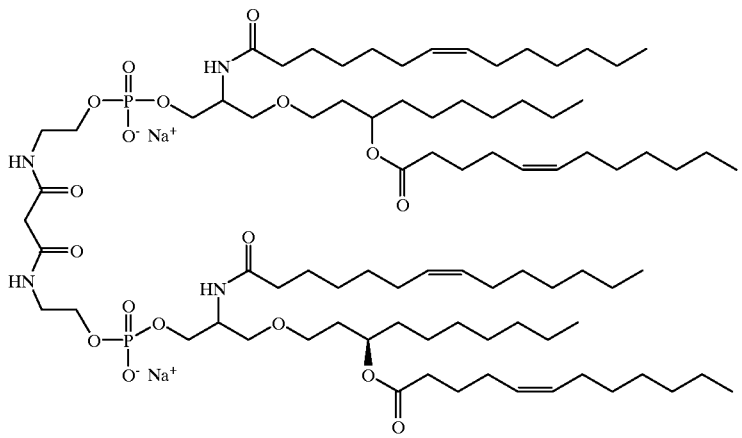 | 138 | | |
| 119327 | 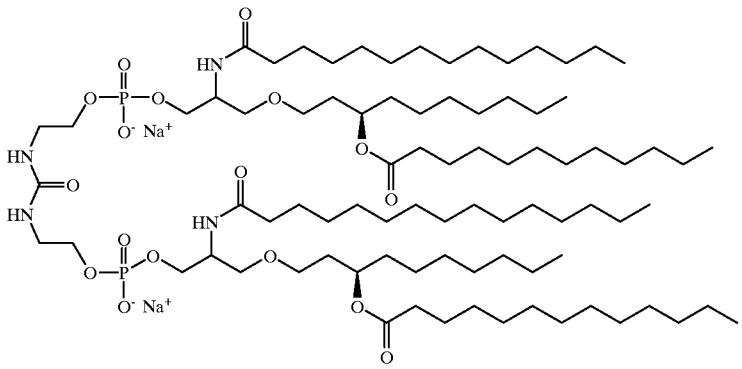 | 165 ± 33 (n = 3) | | |
| 119328 | 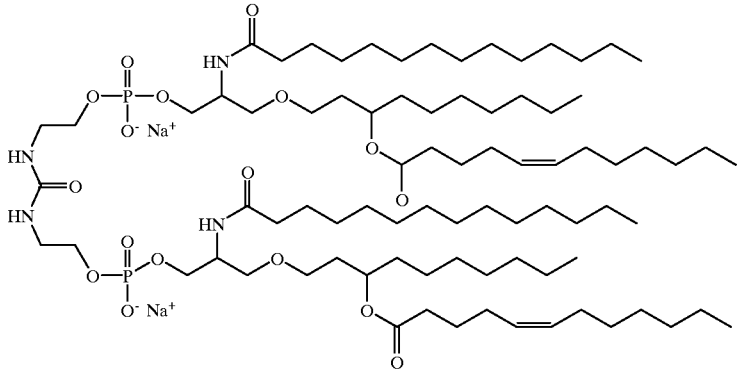 | 181 ± 42 (n = 3) | | |

TABLE 1-continued
Stimulation of cytokine release by compounds in vitro
| ER # | Compound | Whole Blood (% of LPS at 10 μM) | THP-1 cell Stimulation (% of compound 100 at 10 μM)[1] | |
|---|---|---|---|---|
| | MPL Standard | 29[2] | +serum | −serum |
| 119329 | 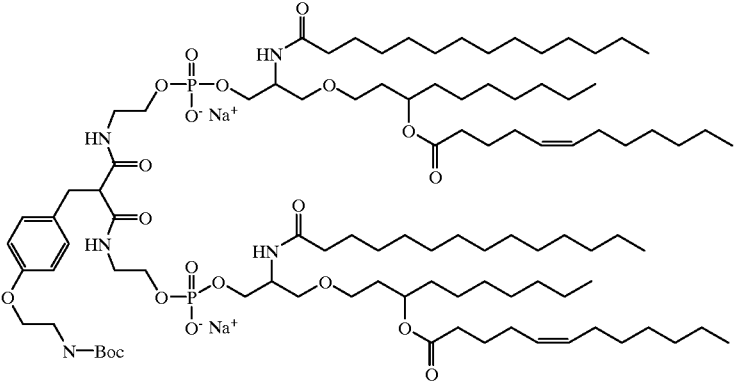 | 2 ± 2 (n = 2) | | |
| 119521 | 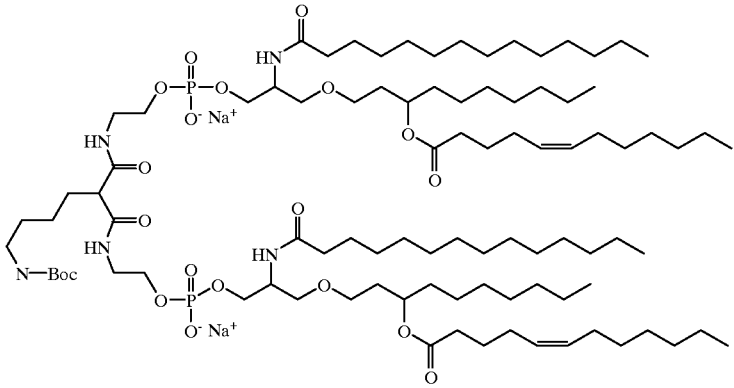 | 103 | | |
| 119522 | 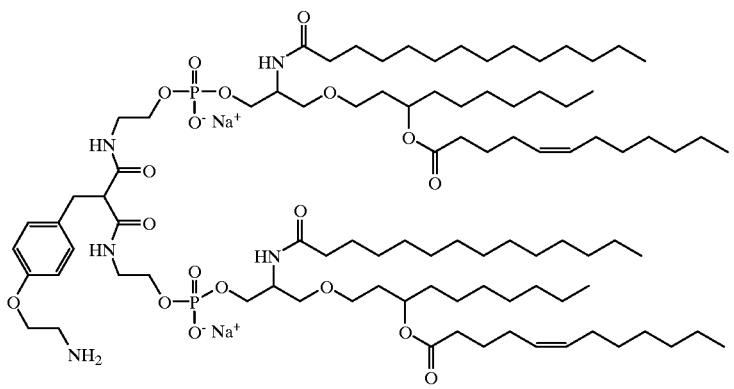 | 129 | | |

TABLE 1-continued
Stimulation of cytokine release by compounds in vitro
| ER # | Compound MPL Standard | Whole Blood (% of LPS at 10 μM) 29[2] | THP-1 cell Stimulation (% of compound 100 at 10 μM)[1] | |
|---|---|---|---|---|
| | | | +serum | −serum |
| 119523 | 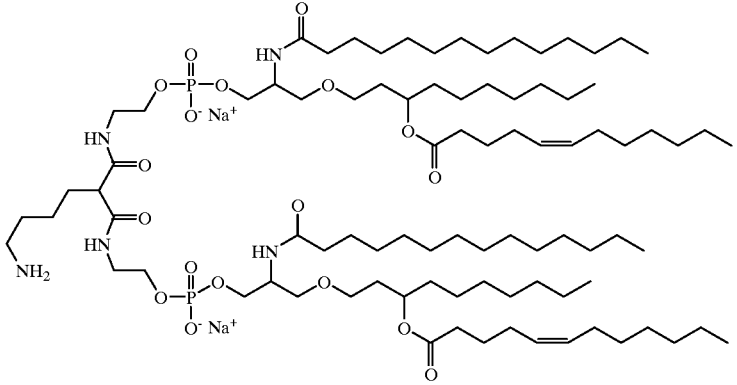 | 176 | | |
| 803022 | 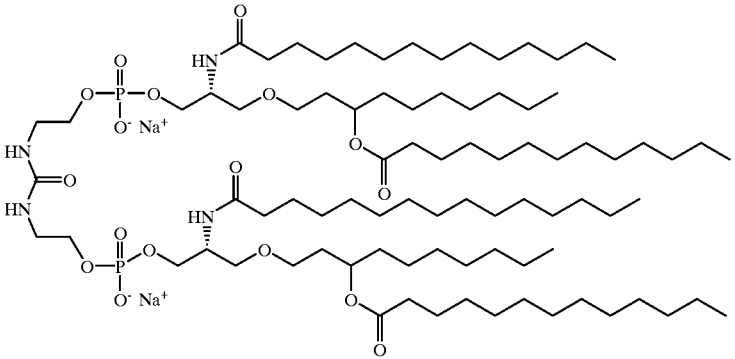 | 164 | | |
| 803045 | 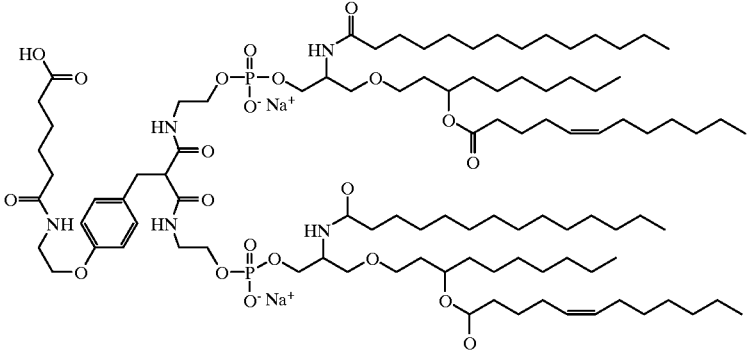 | 65 | | |

TABLE 1-continued

Stimulation of cytokine release by compounds in vitro

| ER # | Compound MPL Standard | Whole Blood (% of LPS at 10 μM) 29[2] | THP-1 cell Stimulation (% of compound 100 at 10 μM)[1] +serum | −serum |
|---|---|---|---|---|
| 803056 | | 151 ± 42 | | |
| 803058 | | 149 ± 37 (n = 2) | | |
| 803059 | | 2 | | |

TABLE 1-continued

Stimulation of cytokine release by compounds in vitro

| ER # | Compound<br>MPL Standard | Whole Blood<br>(% of LPS at<br>10 μM)<br>29[2] | THP-1 cell Stimulation<br>(% of compound<br>100 at 10 μM)[1] | |
|---|---|---|---|---|
| | | | +serum | −serum |
| 803592 | [structure] | 15 | | |

[1]Response in each assay was compared to 10 μM compound 100 internal standard which typically induced 2–3 fold increase in TNF-alpha PLAP expression over basal.
[2]Tested at @ 5.8 μM.

C. Murine Splenocytes

The ability of compounds to stimulate cytokine release from splenocytes can be assessed in a mouse model. Spleen cells harvested from C57BL/6 mice are cultured for 24 hours in RPMI 1640 cell culture medium containing 5% FBS, 1 mM sodium pyruvate, 2 mM L-glutamine, 100 U/ml penicillin/streptomycin and 50 μM beta-mercaptoethanol, various concentrations of test compound for 20–24 hours, after which the cell culture supernatant is tested for the presence of cytokines.

Figure 3:
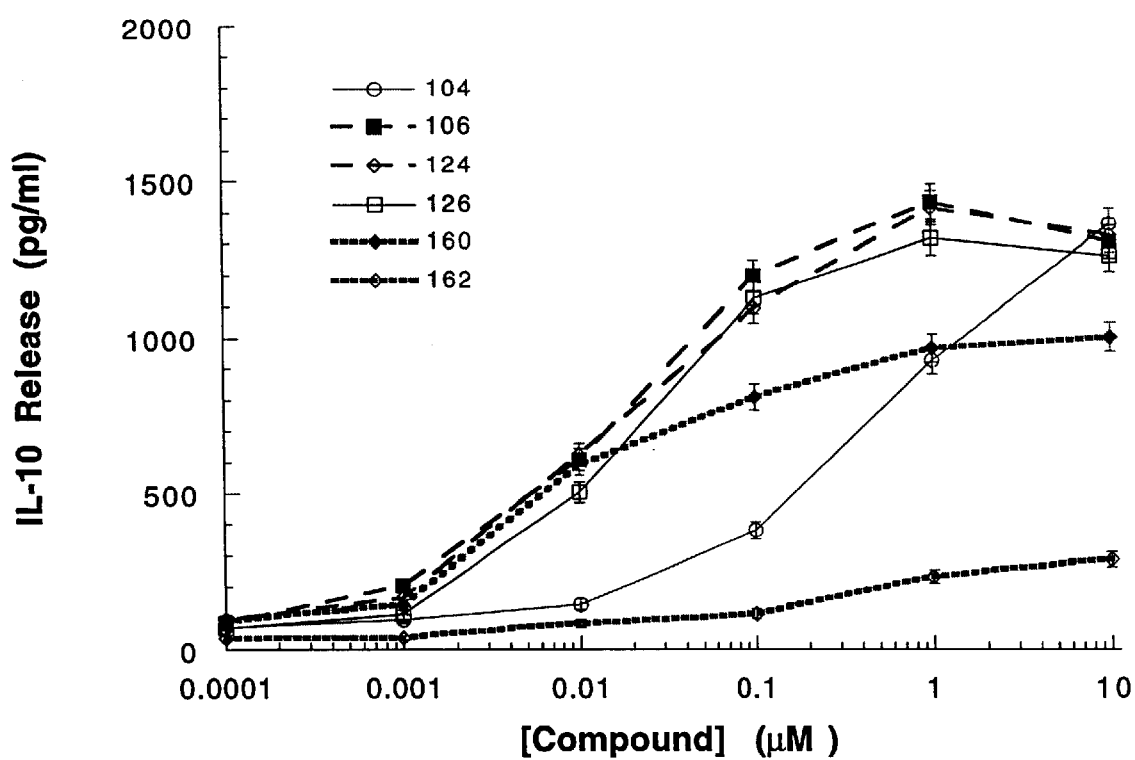
FIG. 3 is a graph showing stimulation of IL-10 release from normal mouse splenocytes by compounds 104, 106, 124, 126, 160, and 162 of the invention.
Figure 4:
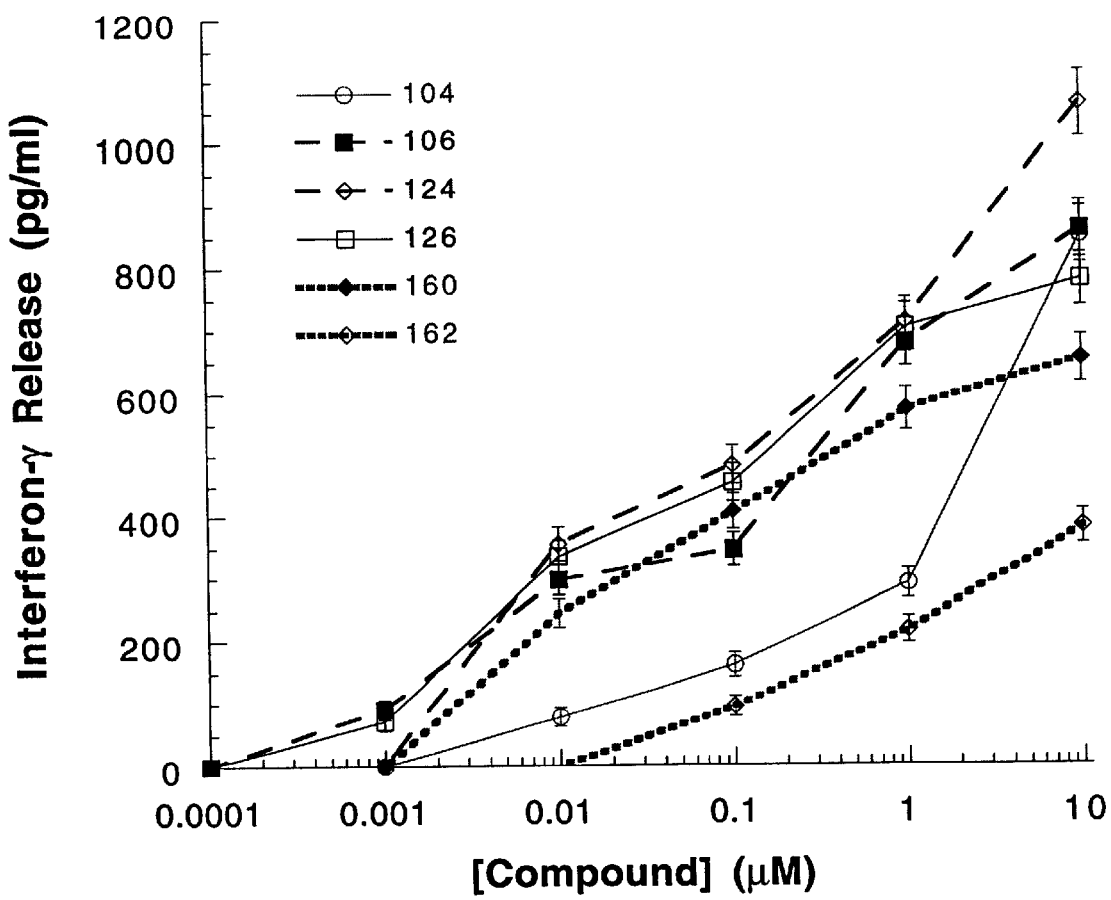
FIG. 4 is a graph showing stimulation of interferon-gamma release from normal mouse splenocytes by compounds 104, 106, 124, 126, 160, and 162 of the invention.

Spleen cells harvested from mice were cultured for 24 hours with test compound and the supernatant was tested for release of cytokines. As shown in FIGS. 3 and 4, the release of cytokines such as IL-10 and interferon-gamma from splenocytes is stimulated by compounds such as 104, 106, 124, 126, 160, and 162.

These assays utilized a heterogeneous population of cells derived from the spleen. This makes it possible that cytokine induction can be caused both by direct effects of test compounds on cells and through more indirect stimulation of cytokine "cascades" where the release of a cytokine by one type of cell can induce release of other cytokines in other cells present in the same media. It is possible that this cytokine "milieu" is responsible for part of this robust immune responses.

Example 8
In Vivo Induction of Antibody Response

The most critical test of adjuvant activity is the determination if the addition of a compound to an antigen preparation increases immune response by elevating the level of antibodies generated to that antigen when administered to a living animal.

Initial experiments involved the injection of mice (Balb/c) with compounds of the invention plus a peptide conjugated to a carrier such as keyhole limpet hemocyanin. The peptide chosen for these studies is a peptide (P18) that corresponds to amino acids 308–322 of the V3 loop of HIV IIIB gp120 protein. The P18 21aa peptide, corresponding to amino acids 308–322 of the V3 loop of HIV IIIB gp120 protein, has been reported to be immunogenic. This peptide with glycine/alanine/glycine spacer residues plus an amino terminal cysteine residue was synthesized by Genosys (Woodlands Tex.). The peptide sequence is as follows: CGAGIRIQRG-PGRAFVTIGKG with the underlined amino acids representing the native sequence. The peptide was isolated to >80% purity using HPLC by the supplier. This peptide was coupled via the cysteine residue to bovine serum albumin (BSA) and keyhole limpet hemocyanin (KLH) using maleimide activated conjugation (Pierce Immunochemical; cat #77107). The KLH conjugated peptide was used as the immunogen and the BSA conjugate as the screening target antigen for P18 specific antibodies. The indicated amount of KLH-P 18 conjugate, was routinely used along with 300 μg of test compound, Alum or PBS was injected at 2 or 3 week intervals (as indicated), into male Balb/c mice (Charles River Laboratories) approximately 6–8 weeks old (18–25 g). All injections were subcutaneous at the back of the neck with 200 μl of a mixture of antigen plus adjuvant in PBS administered every two weeks (three weeks for polysaccharides or influenza) for a total of three injections. Mice were bled one-or two weeks post $2^{nd}$ and $3^{rd}$ injections. Sample bleeds are designated as to when taken (i.e. secondary bleed is one week after the second protein injection or two weeks after the second polysaccharide injections, tertiary bleed is after the third injection of antigen/adjuvant. Blood was collected after nicking the tail vein and drops collected into Becton Dickinson brand microtainer serum separator tubes. Serum was separated from the red cells by microcentrifugation and tested by ELISA for antigen specific IgG levels.

Immune response to the peptide can be tested by enzyme-linked immunosorbent assay (ELISA), which can quantitate levels of serum antibody that bind to P18 peptide conjugated to another non-cross-reacting protein such as bovine serum albumin (P18-BSA) and coated onto an ELISA plate.

Figure 5:
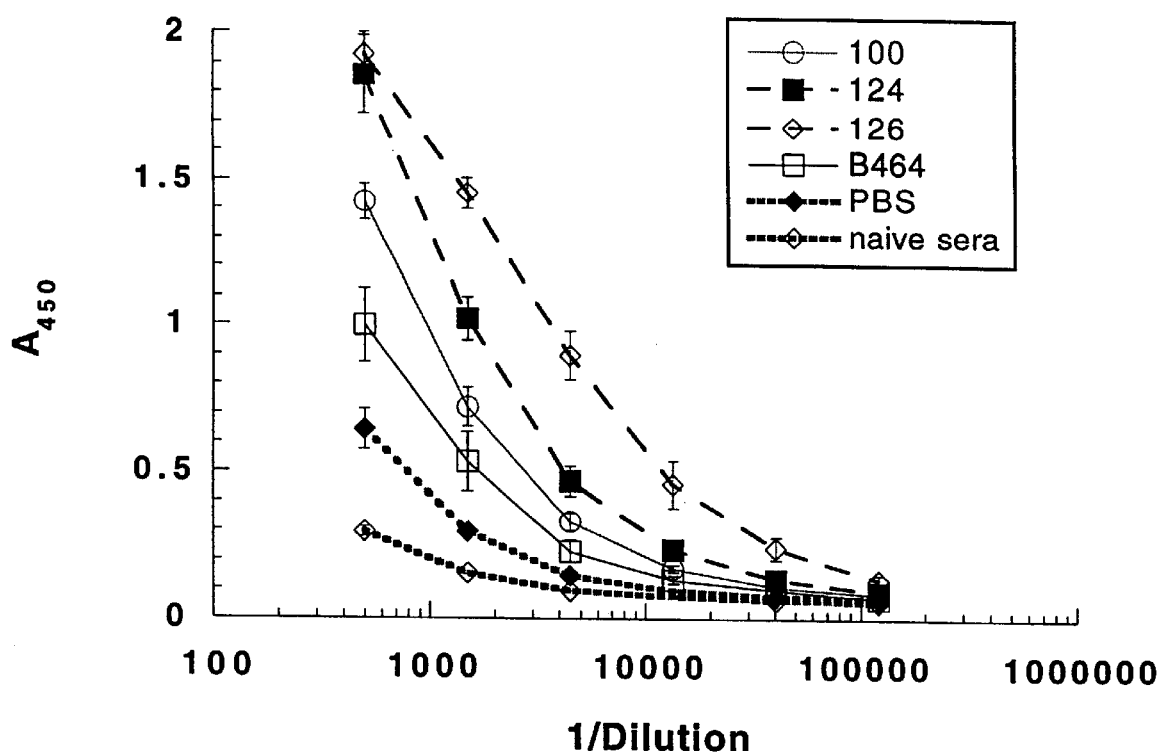
FIG. 5 is a graph illustrating the results of serum tritration analysis for determining the amounts of antibody that are produced in response to keyhole limpet hemocyanin in the absence and presence of compounds 100, 124, and 126 of the invention.

As shown in FIG. 5 and Tables 2 and 3, mice injected with the various compounds along with KLH-P18 antigen demonstrated greater response (higher levels of antibody) than those injected with the P18-KLH peptide conjugate alone.

TABLE 2

Stimulation of antibody generation to P18 peptide by compounds

| ER # | Compound | Average Serum anti-P18 IgG Concentration[1] (fold increase over no adjuvant) |
|---|---|---|
| 112022 | 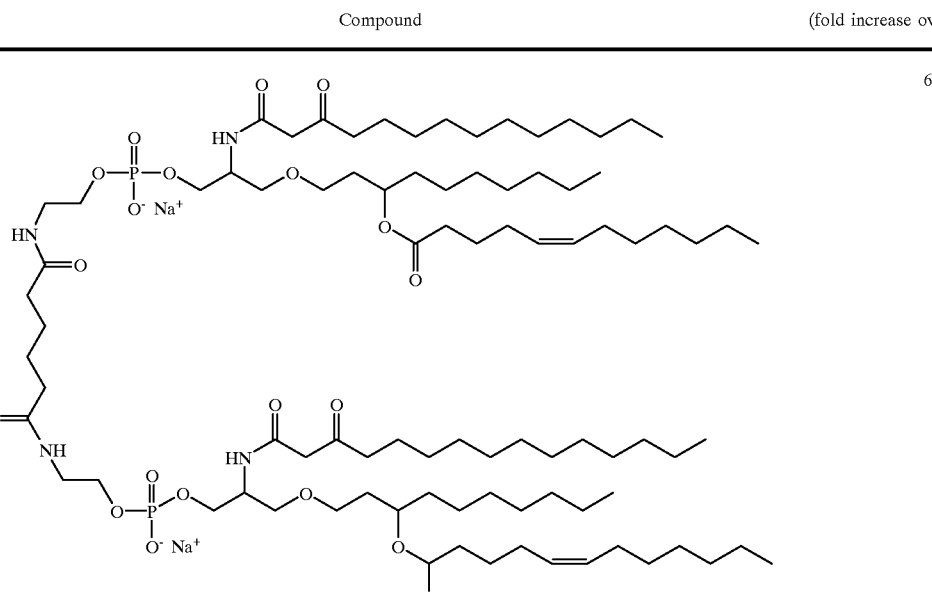 | 6.7 |
| 112065 | 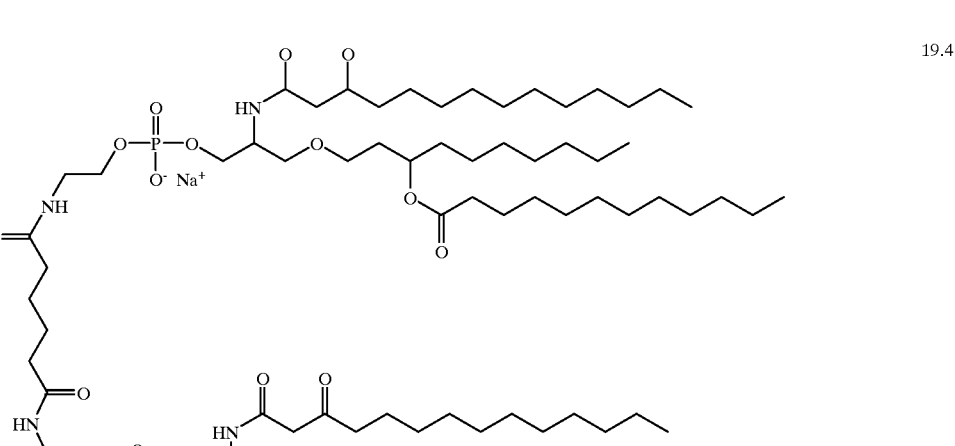 | 19.4 |

TABLE 2-continued

Stimulation of antibody generation to P18 peptide by compounds

| ER # | Compound | Average Serum anti-P18 IgG Concentration[1] (fold increase over no adjuvant) |
|---|---|---|
| 112066 | (structure) | 39.2 |

[1]Concentration of IgG assayed at the tertiary bleed. Average IgG for serum from 5 mice that were injected with 300 μg compound and 5 μg KLH-P18 conjugate antigen as described in the Methods section. Antigen-specific ELISAs were performed as described in the Methods Section with Costar EIA/RIA plates coated with 50 μl of 5 μg/ml BSA-P18 conjugate in PBS.

TABLE 3

Stimulation of antibody generation to P18 peptide by compounds

| Compound # | Compound | Average Serum anti-P18 IgG Concentration[1] (fold increase over no adjuvant) |
|---|---|---|
| 111232 | (structure) | 7.6 |

TABLE 3-continued

Stimulation of antibody generation to P18 peptide by compounds

| Compound # | Compound | Average Serum anti-P18 IgG Concentration[1] (fold increase over no adjuvant) |
|---|---|---|
| 112066 | | 13.4* |
| 113651 | | 10.5* |
| 118989 | | 4.35* |

TABLE 3-continued

Stimulation of antibody generation to P18 peptide by compounds

| Compound # | Compound | Average Serum anti-P18 IgG Concentration[1] (fold increase over no adjuvant) |
|---|---|---|
| 119327 | | 16.5* |
| 119328 | | 26.8* |

[1]Concentration of IgG assayed at the tertiary bleed. Average IgG for serum from 5 mice that were injected with 300 μg compound and antigen (below) as described in the Methods section. Antigen-specific ELISAs were performed as described in the Methods section with Costar EIA/RIA plates coated with 50 μl of 5 μg/ml BSA-P18 conjugate in PBS. As comparison, addition of Alum increased IgG levels 7.4– fold over PBS/antigen alone. Antigen used: primary: 1 μg KLH-conjugated P18 peptide. 2° and 3° boosts: 0.5 μg KLH-conjugated P18 peptide *p < 0.05 by Student's two-tailed t-test (unequal variance) compared to the PBS + antigen group.

Adjuvant activity has also been obtained with compounds of the invention when tested with other antigens. Compounds such as 100, 116, 126, 160, 184, and 186 can stimulate antigen-specific antibody production by up to 26.8-fold (Table 4) to influenza X-31 antigen. Increases in response are also seen when tetanus toxoid (FIG. 6) and menningo- coccal C polysaccharide (Table 5) are used as challenge antigens. In the assays, 1 µg of meningococcal C PS or 1.5 µg tetanus toxoid or 5 µg of influenza X31 (SPAFAS laboratories) were used. Tetanus toxoid from Accurate Chemical (cat #sstettox) was used as a challenge antigen while the purified toxoid from List Biologicals (cat #191) was used as target antigen for the ELISA assay.

TABLE 4

Stimulation of antibody generation to Influenza X31 by compounds

| ER # | Compound | Average Serum anti-Influenza X-31 IgG Concentration[1] (fold increase over no adjuvant) |
|---|---|---|
| 112022 | 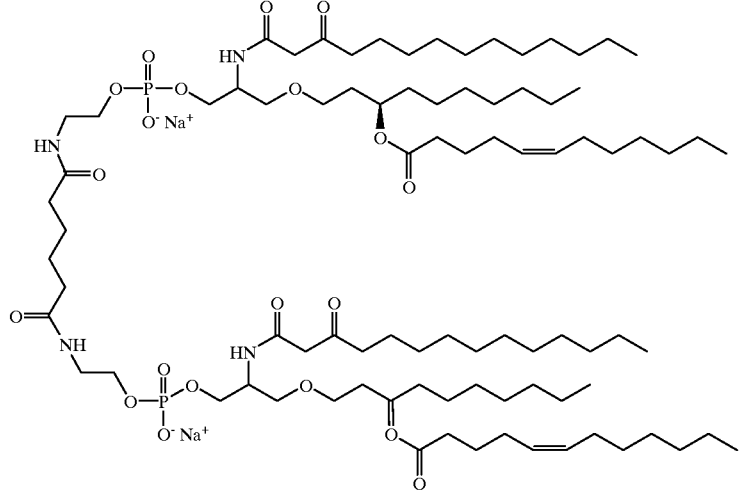 | 1.7 |
| 112048 | 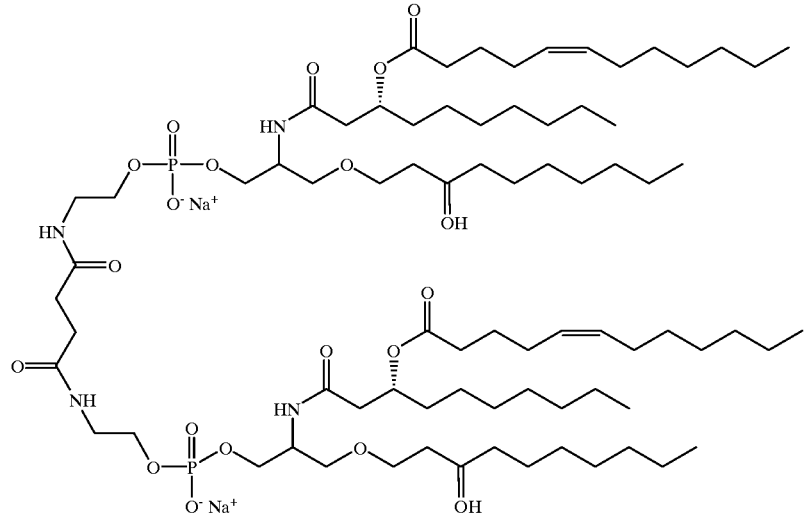 | 5.4 |

TABLE 4-continued

Stimulation of antibody generation to Influenza X31 by compounds

| ER # | Compound | Average Serum anti-Influenza X-31 IgG Concentration[1] (fold increase over no adjuvant) |
|---|---|---|
| 112066 | | 2.3 |
| 113651 | | 1 |
| 119327 | | 7.85 |

TABLE 4-continued

Stimulation of antibody generation to Influenza X31 by compounds

| ER # | Compound | Average Serum anti-Influenza X-31 IgG Concentration[1] (fold increase over no adjuvant) |
|---|---|---|
| 119328 | | 26.8 |

[1]Concentration of IgG assayed at the tertiary bleed.
Average IgG for serum from 5 mice that were injected with 300 μg compound and 5 μg antigen as described in the Methods section. Antigen-specific ELISAs were performed as described in the Methods Section with Costar EIA/RIA plates coated with 50 μl of 10 μg/ml Influenza X-31 antigen in 0.5M sodium carbonate buffer pH 9.6 As comparison, addition of Alum increased IgG levels 3.5- fold over PBS/antigen alone.

TABLE 5

Stimulation of antibody generation to Menningococcal polysaccharide by compounds

| ER # | Compound | Average Serum anti-Menningococcal PS IgG Concentration[1] (fold increase over no adjuvant) |
|---|---|---|
| 112032 | | 8.3 |

TABLE 5-continued

Stimulation of antibody generation to Menningococcal polysaccharide by compounds

| ER # | Compound | Average Serum anti-Menningococcal PS IgG Concentration[1] (fold increase over no adjuvant) |
|---|---|---|
| 112048 | | 1.8 |
| 112066 | | 12.9 |
| 113651 | | 18.3 |

TABLE 5-continued

Stimulation of antibody generation to Menningococcal polysaccharide by compounds

| ER # | Compound | Average Serum anti-Menningococcal PS IgG Concentration[1] (fold increase over no adjuvant) |
|---|---|---|
| 119327 | (structure) | 15.8 |

[1]Concentration of IgG assayed at the secondary bleed.
Average IgG for serum from 5 mice that were injected 300 μg compound and 1 μg antigen as described in the Methods section. Antigen-specific ELISAs were performed as described in the Methods Section with Costar EIA/RIA plates coated with 50 μl of 5 μg/ml meningococcal PS in PBS plus methylated human serum albumin as described Gheesling et al. J. Clin Microbiol.32; 1475–82 (1994). In comparison, addition of Alum increased IgG levels 2.3- fold over PBS/antigen alone.

Influenza virus X-31 was purchased from SPAFAS (Storrs, Conn.) and was inactivated and confirmed to be inactive [Payne et al. Vaccine 16; 92–98 (1998)] by the supplier.

Menningococcal C polysaccharide (PS) was supplied by Pasteur Merrieur Connaught (Swiftwater Pa.). Methylated human albumin can be obtained according to the methods described by Gheesling et al. J. Clin Microbiol.32; 1475–82 (1994).

For the preparation of antigen/adjuvant mixtures, lyophilized test compounds were reconstituted to 2 mg/ml with phosphate buffered saline (PBS; cat #P-3813; Sigma Chemical Co, St Louis Mo.) and sonicated in a chilled water bath for two minutes. Monophosphoryl Lipid A, MPL, (Ribi Immunochemical) was reconstituted to 2 mg/ml with sterile water for injection, incubated at 50° C. for 15 minutes and then sonicated as above. Imject® Alum, purchased from Pierce Immunochemical, was used according to manufacturer's guidelines, and comprised approximately 20–30% of the injection volume. Indicated amounts of antigen, diluted in PBS, were mixed with the compounds, MPL, or Alum such that the final concentration of the compound or MPL was 300 μg (unless otherwise noted) in the 200 μl injection volume. The mixtures were incubated at room temperature for 40 minutes with continuous shaking prior to injection.

Antigen specific IgG levels were monitored by direct ELISA where antigen was passively coated onto 96 well Costar EIA/RIA plates. Plates were coated with 501 μl/ well of the indicated antigen and incubated overnight (ON) at 4° C. and washed 3x with PBS +0.05% tween 20 (PBS-t) in an automated plate washer. Plates were then blocked with 200 μl/well of 0.5% gelatin in PBS for 1 hr at room temperature (RT) and washed 3x with PBS-T. Mouse sera was diluted in PBS-t plus 0.3% BSA and 100 μl of various dilutions were added, in duplicate to the antigen coated wells (or BSA coated wells as a control) and incubated at RT for 1 hr. and again washed 3x with PBS-t. Biotinylated goat anti-mouse IgG (Southern Biotechnology Associates Inc., Birmingham Ala., cat #1031-08) was diluted 1:5000 in PBS-t and 100 μl/well was applied and incubated at RT for 1 hr, washed 3x with PBS-t and followed by the addition of 1:10,000 streptavidin-horseradishperoxidase conjugate (Southern Biotechnology Associates Inc.) in PBS-t for 30 minutes at RT and again washed 3x with PBS-t. Wells were then incubated in 100 μL TMB substrate (Kirkegaard and Perry Labs) for 5 minutes. Color development was stopped with the addition of an equal volume of 1 M phosphoric acid and the absorbance was read at 450nm on a Titertek Multiscan plate reader with Deltasoft software analysis package.

For relative quantitation of antigen-specific IgG levels, curves were compared to one another by determining the dilution necessary to obtain a fixed amount of antibody-generated color. In some cases, a total IgG assay using an anti-FAb-specific reagent to capture known amounts of purified IgG (purchased from Southern Biotech.) as an IgG standard curve was run in conjunction with the direct ELISA on the BSA-P18 conjugate. The anti-FAb reagent orients the purified IgG in a manner similar to how an antibody would bind to an antigen through the FAb region. This allows detection of bound antibody by the same reagents used to measure antigen-specific capture of antibodies. The same reagent solutions used for detection of the antibodies bound to BSA-P18 conjugate, namely biotinylated anti-IgG (Fc-specific) followed with HRP-streptavidin, were simultaneously applied to the anti-FAb total IgG quantitative assay and to the antigen-specific assay. Hence, the signal from the binding of the purified IgG standard curve is equivalent to that generated to equal amounts of IgG bound in the anti-target antigen assay. The amount of antibody in the serum is then interpolated from the purified IgG standard using a 4-parameter curve fit (DeltaSoft 3 software package).

TABLE 6

WB ED$_{50}$ vs. % of LPS at 10 ng/ml

| ER# | Structure | WB ED$_{50}$ vs LPS @ 10 ng/ml |
|---|---|---|
| MPL Standard | 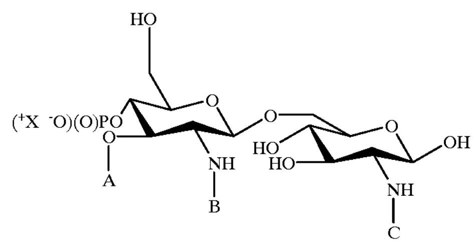 | >>10 μm |
| 112022 | 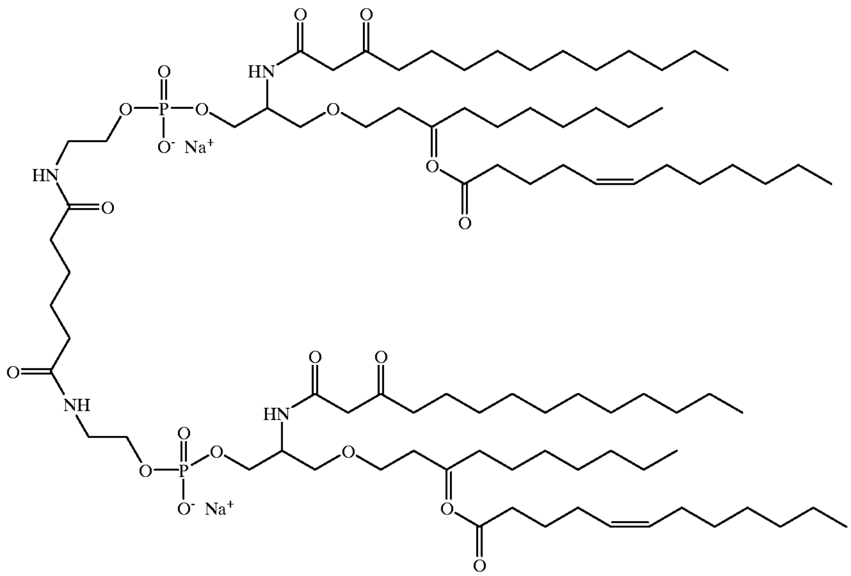 | 0.696 μm |
| 111230 | 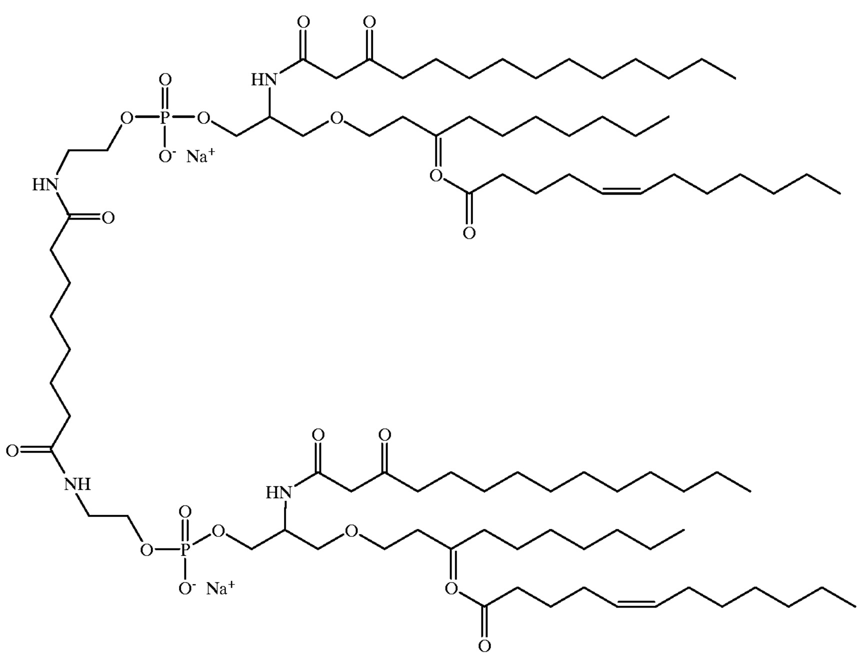 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 111231 | 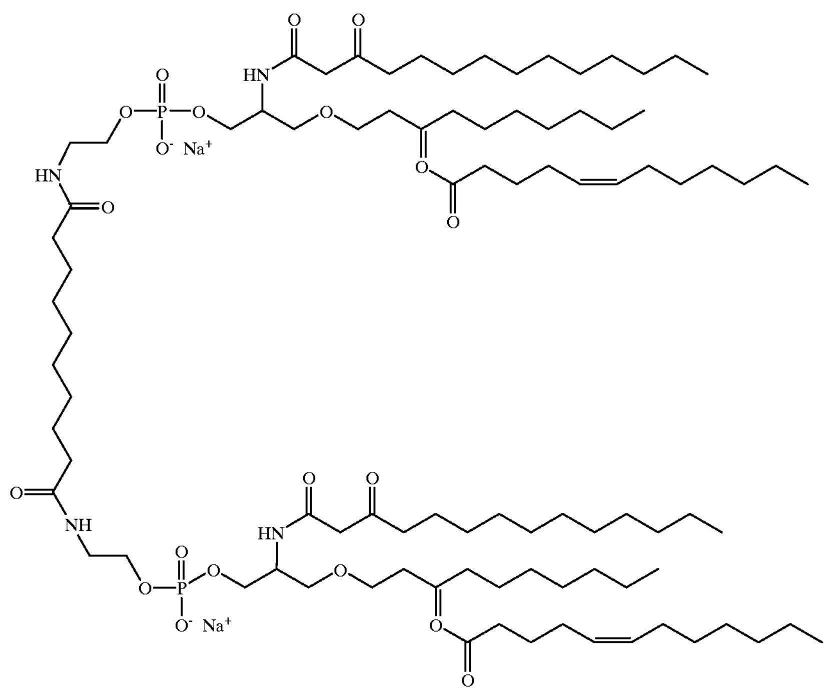 | 0.29 μm |
| 111232 | 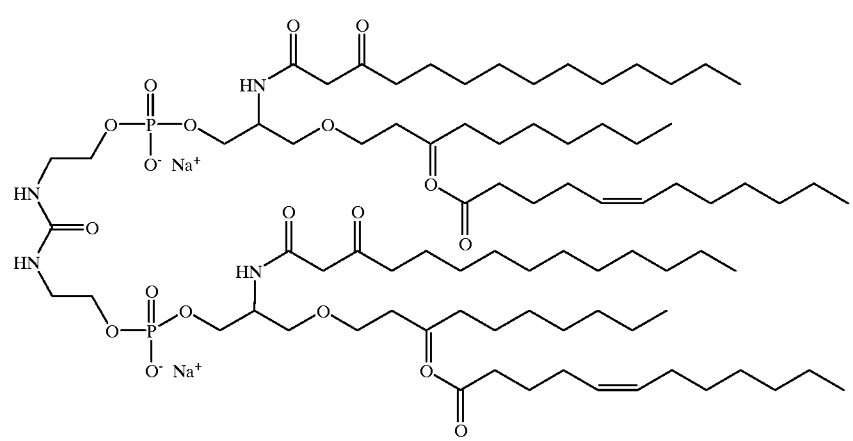 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 111233 | | |
| 112043 | | |
| 112044 | | |

TABLE 6-continued

WB ED$_{50}$ vs. % of LPS at 10 ng/ml

| ER# | Structure | WB ED$_{50}$ vs LPS @ 10 ng/ml |
|---|---|---|
| 112047 | 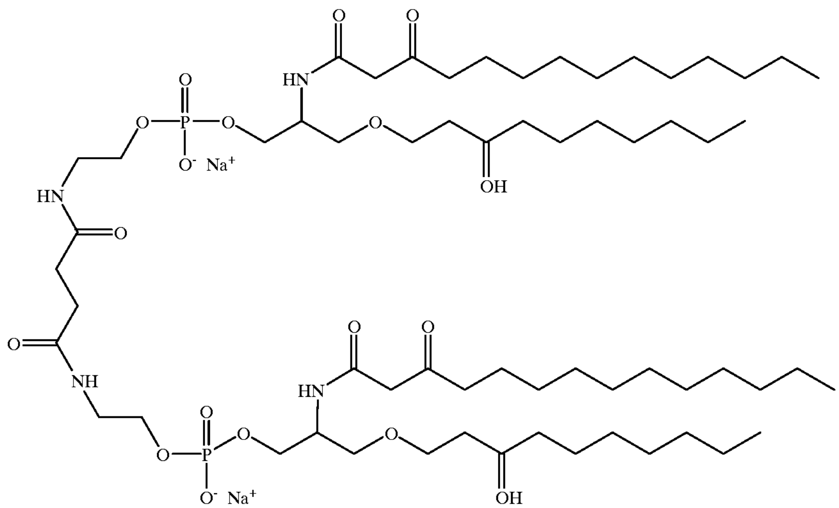 | |
| 112048 | 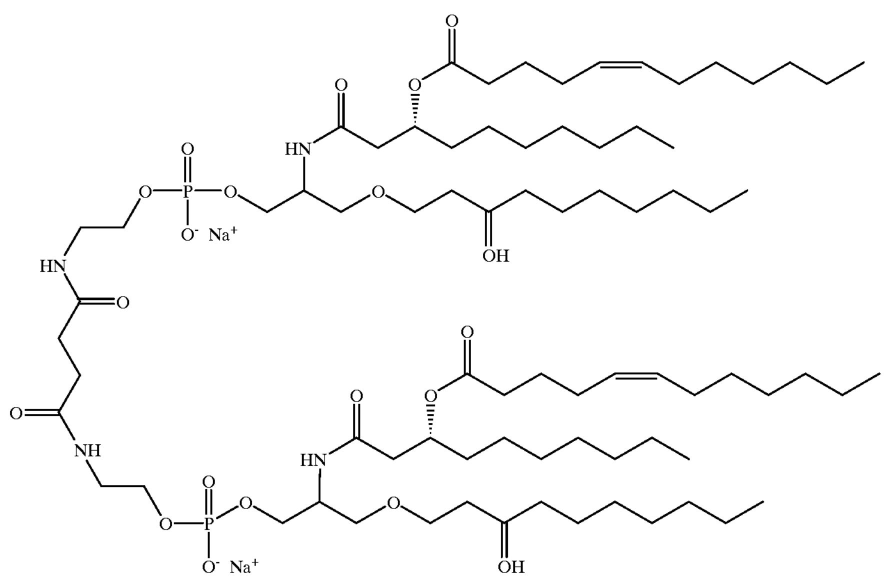 | >>10 μM |

TABLE 6-continued

WB ED$_{50}$ vs. % of LPS at 10 ng/ml

| ER# | Structure | WB ED$_{50}$ vs LPS @ 10 ng/ml |
|---|---|---|
| 112049 | 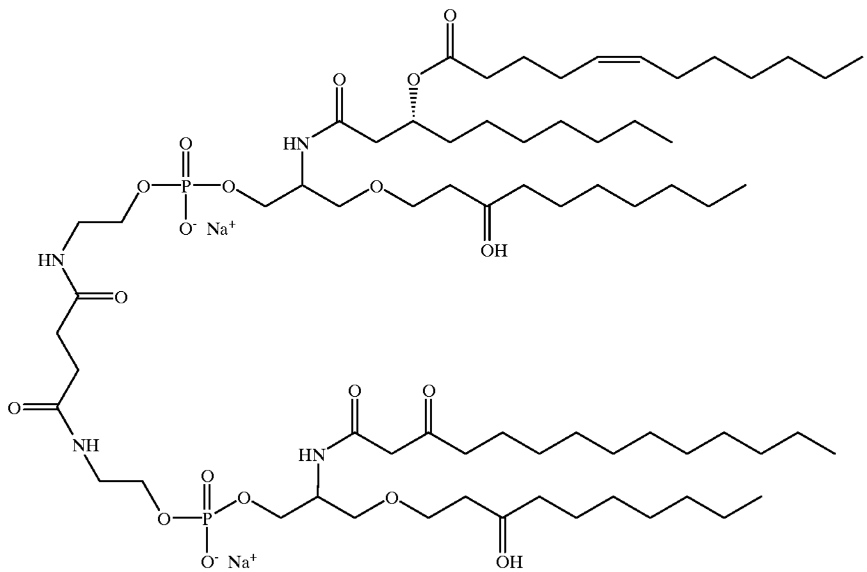 | |
| 112063 | 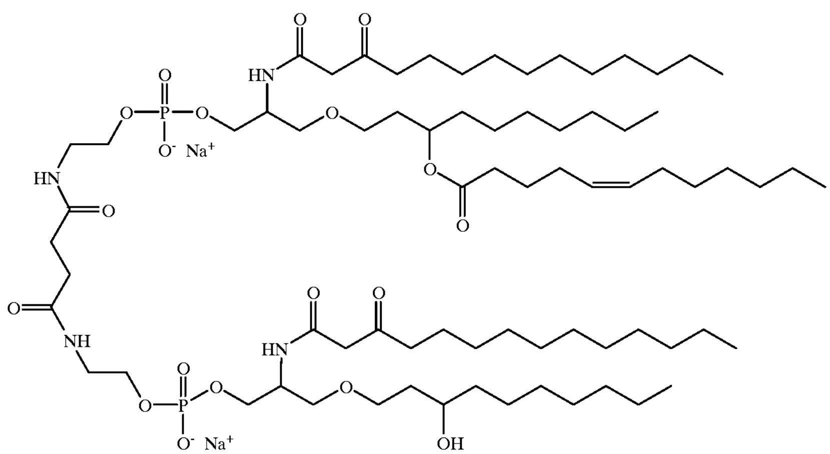 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 112064 | 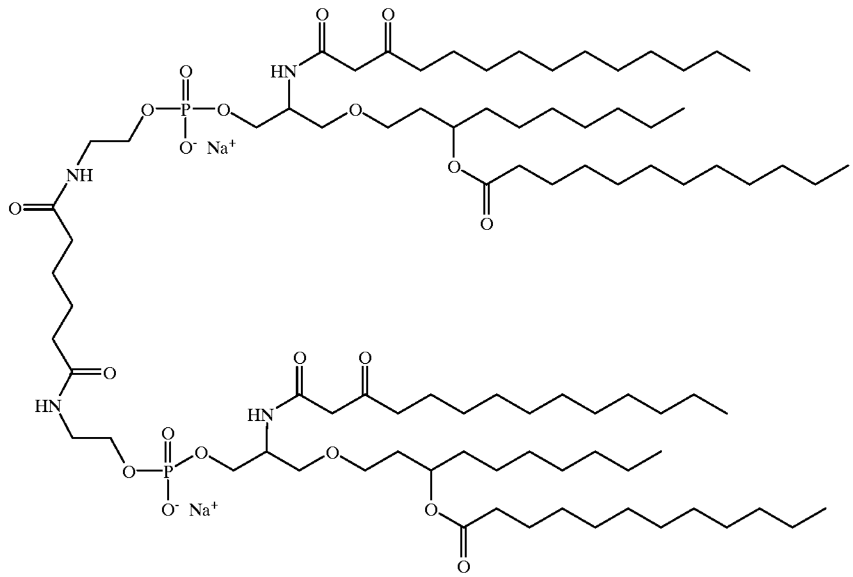 | |
| 112065 | 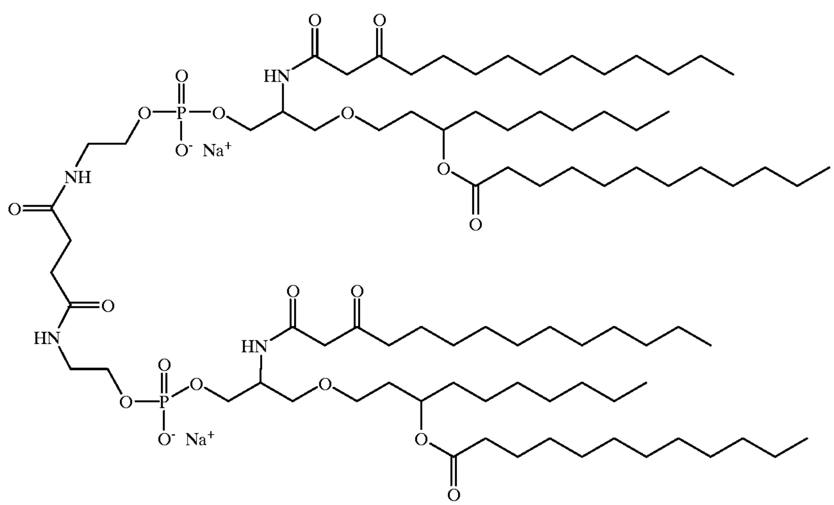 | 0.25 µM |
| 112066 | 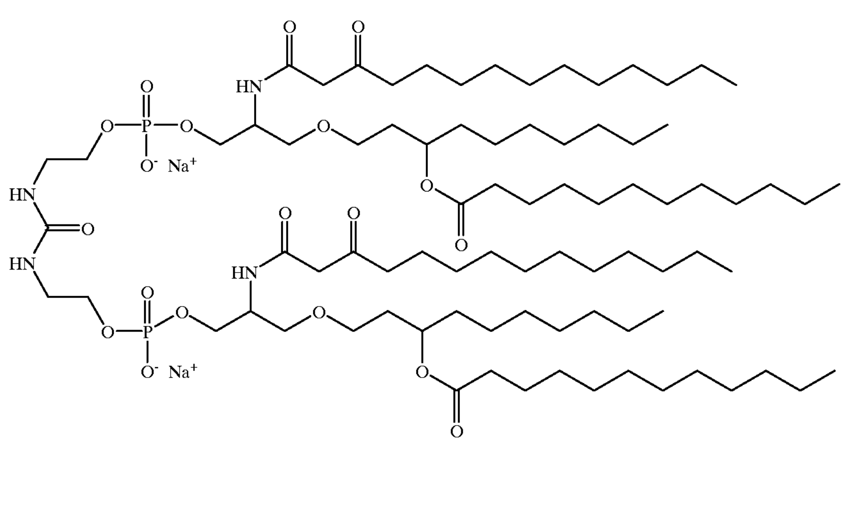 | 0.04 µM |

TABLE 6-continued

WB ED$_{50}$ vs. % of LPS at 10 ng/ml

| ER# | Structure | WB ED$_{50}$ vs LPS @ 10 ng/ml |
|---|---|---|
| 112071 | 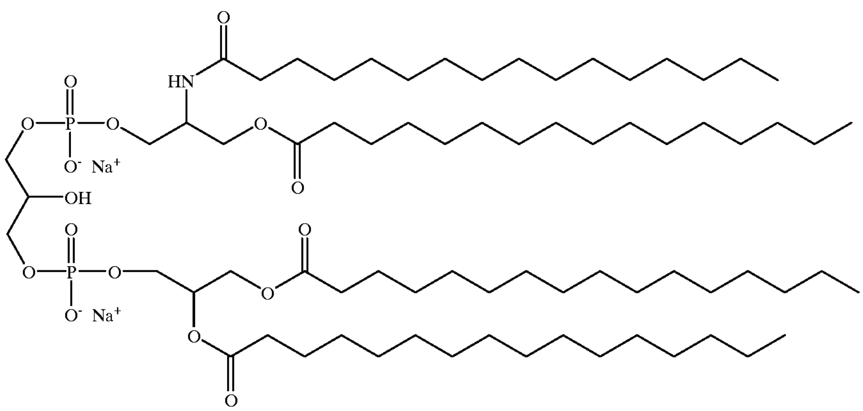 | |
| 112072 | 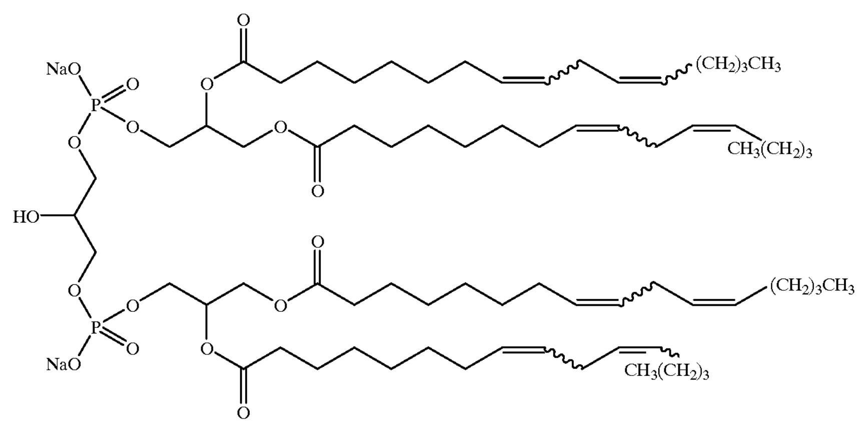 | |
| 112091 | 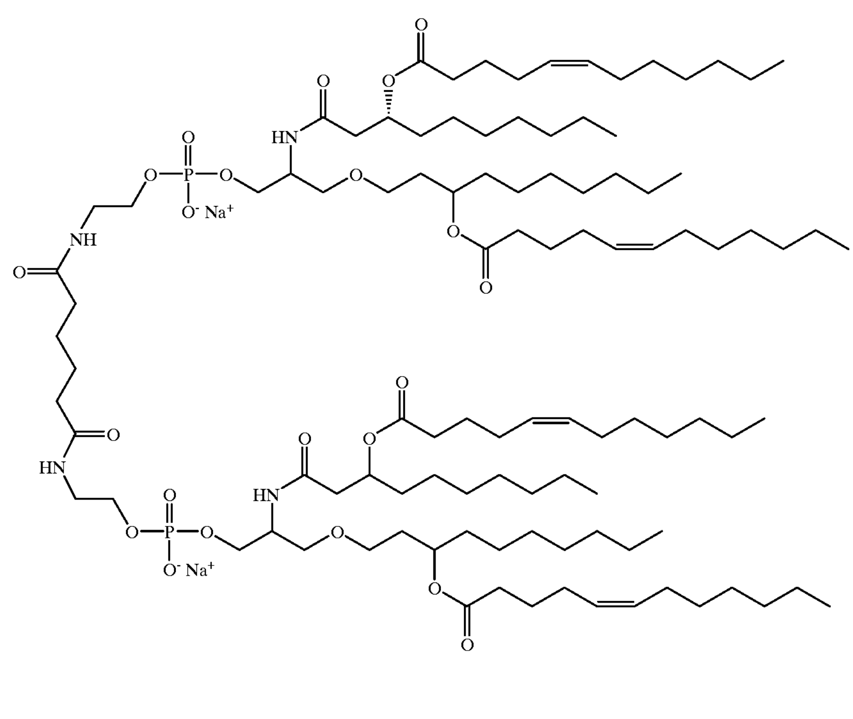 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 112092 | 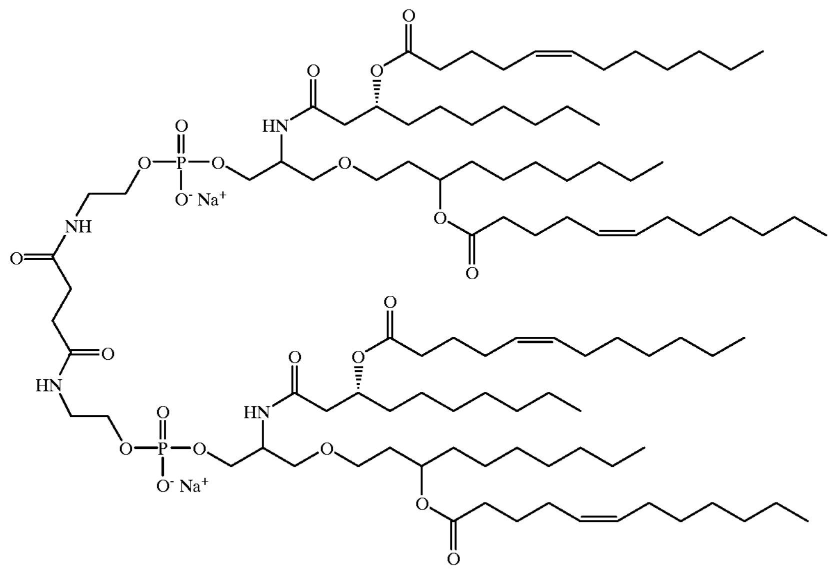 | |
| 112093 | 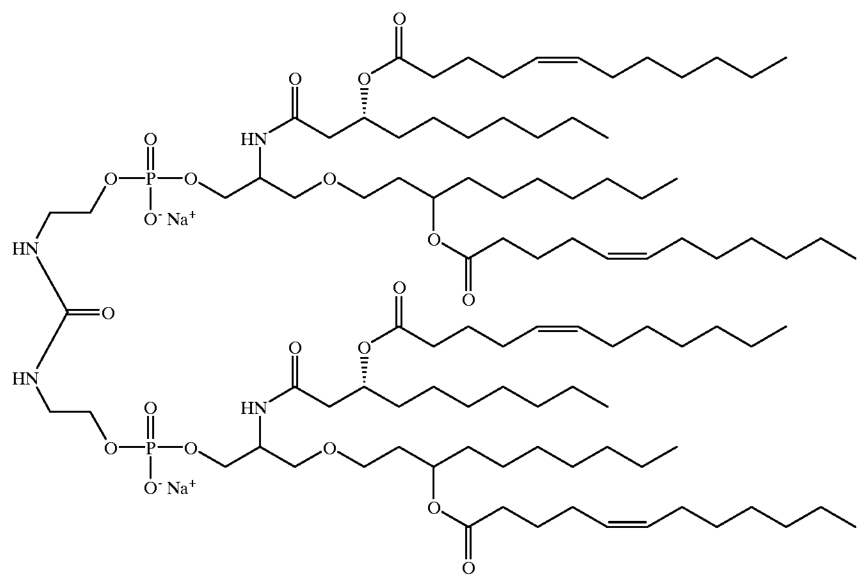 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 112098 | 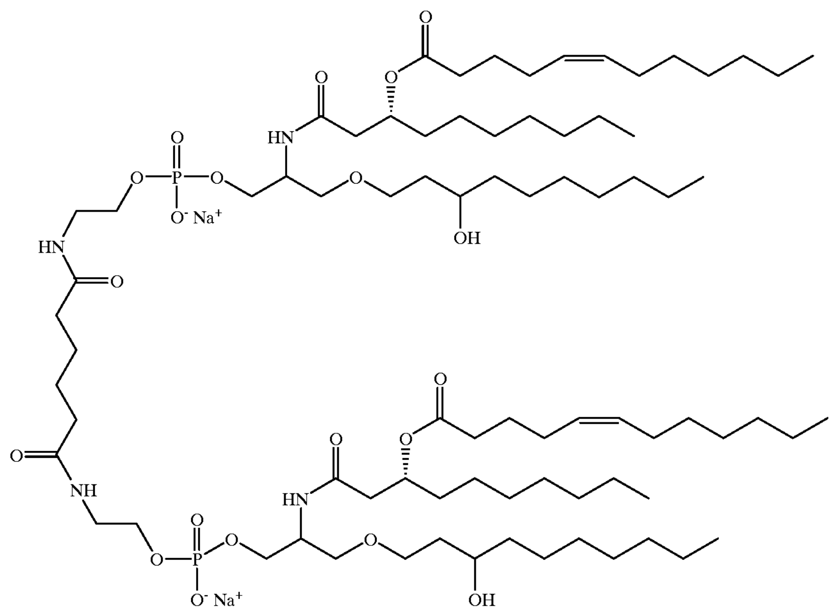 | |
| 112099 | 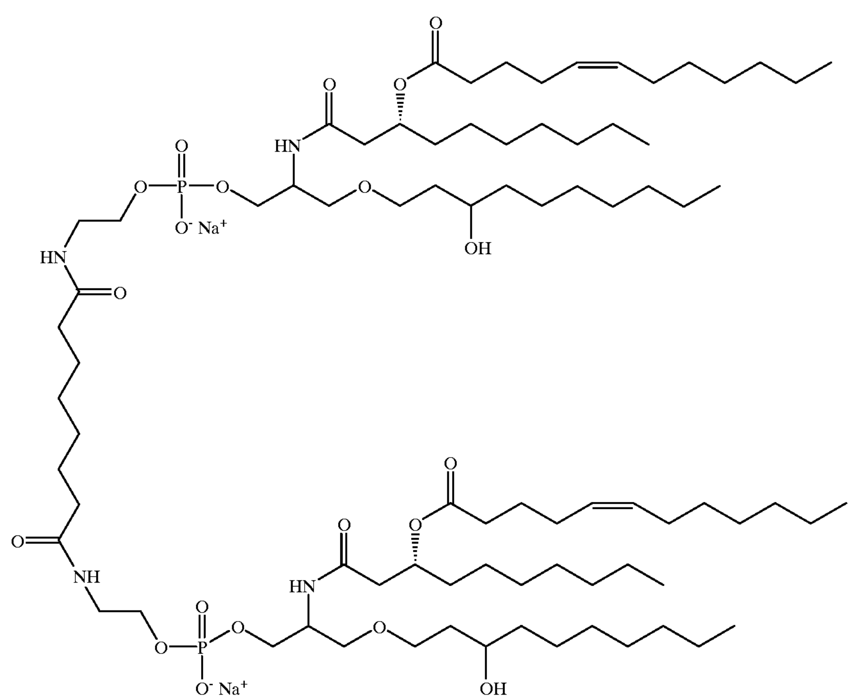 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 112100 | 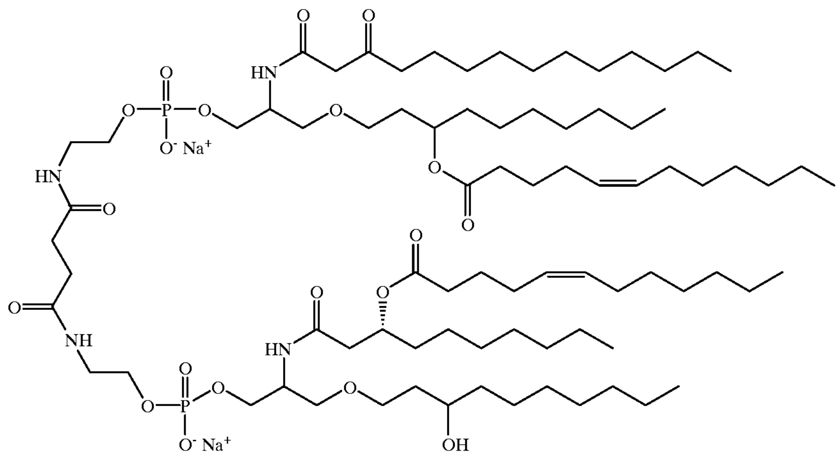 | |
| 112859 | 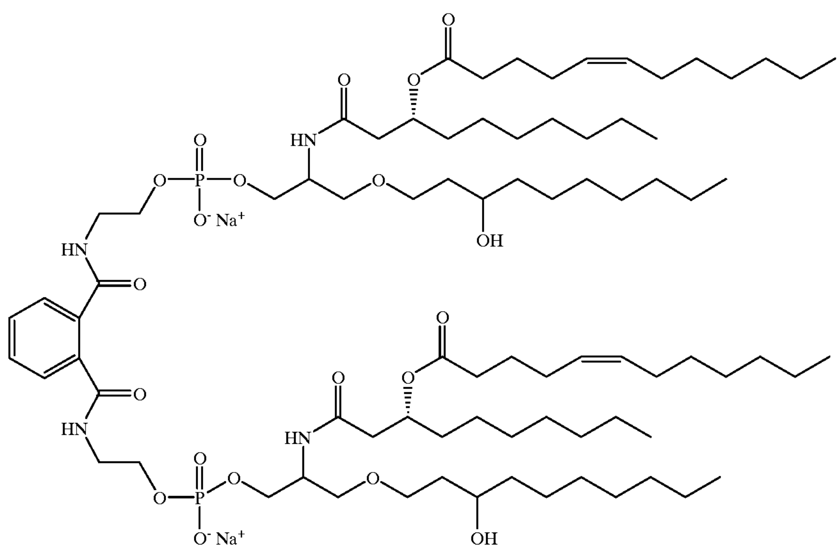 | |

TABLE 6-continued
WB ED$_{50}$ vs. % of LPS at 10 ng/ml
| ER# | Structure | WB ED$_{50}$ vs LPS @ 10 ng/ml |
|---|---|---|
| 112860 | 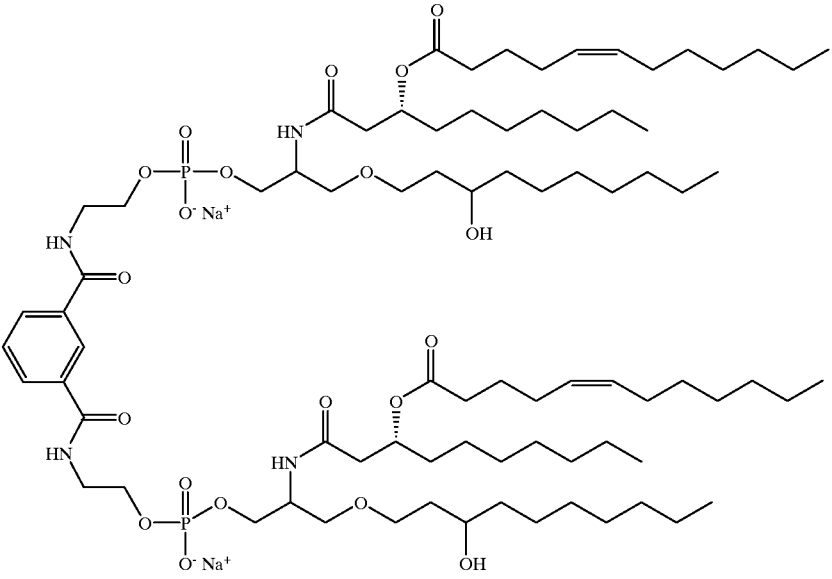 | |
| 112861 | 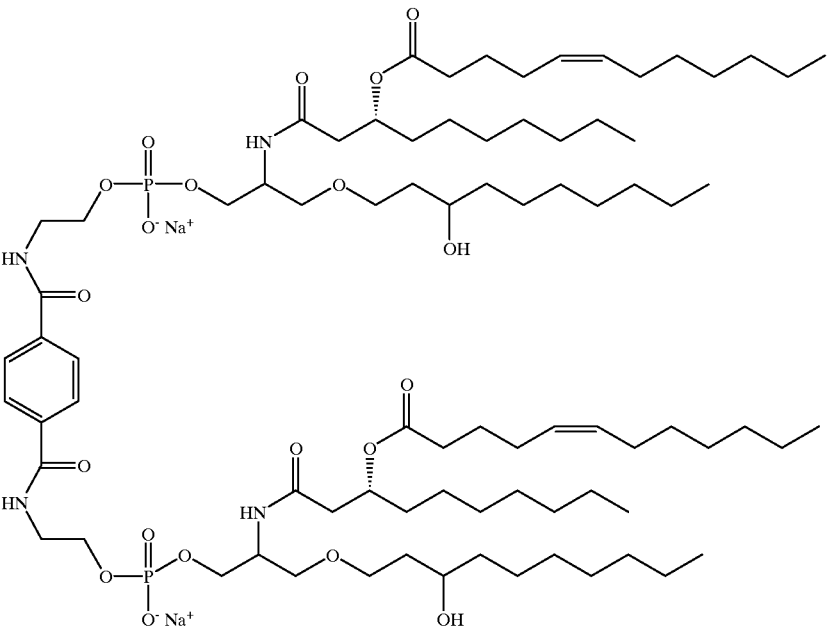 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 113634 | 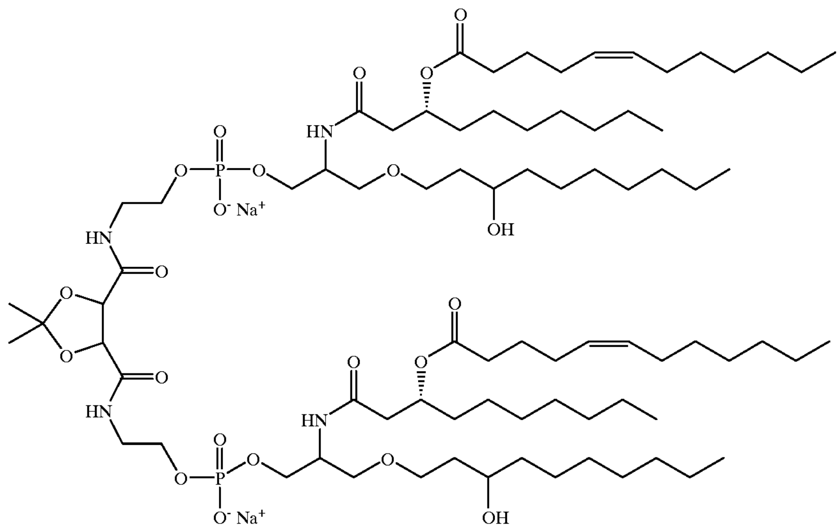 | |
| 113635 | 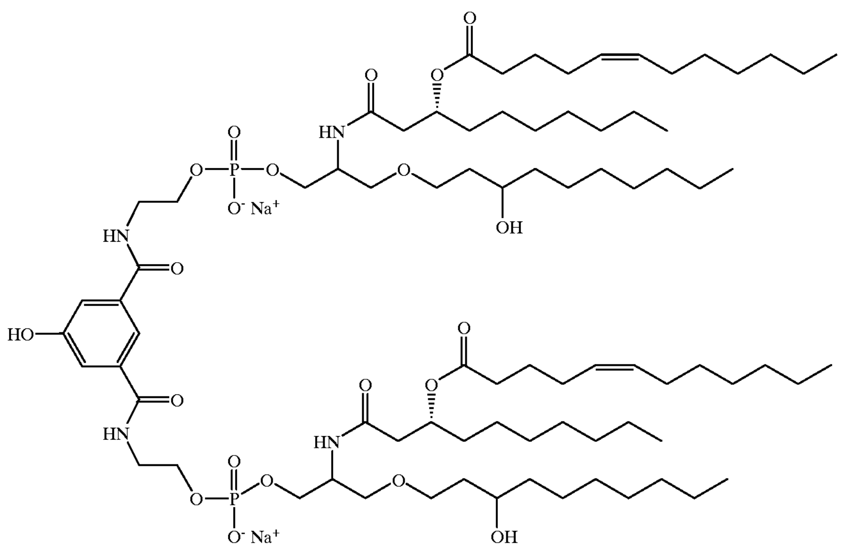 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 113643 | 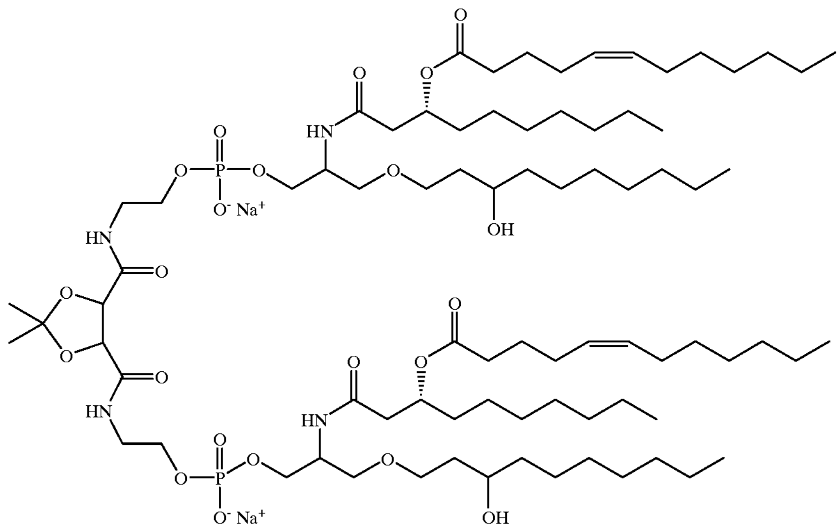 | |
| 113644 | 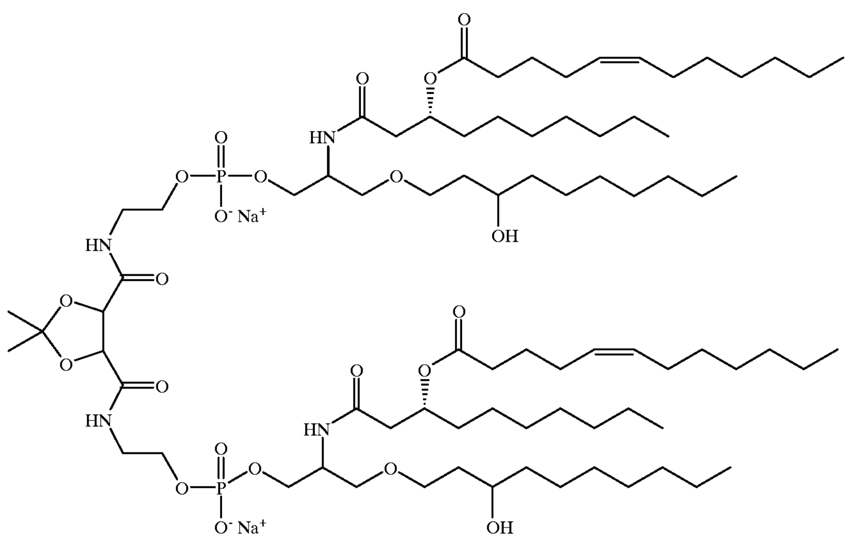 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 113651 | 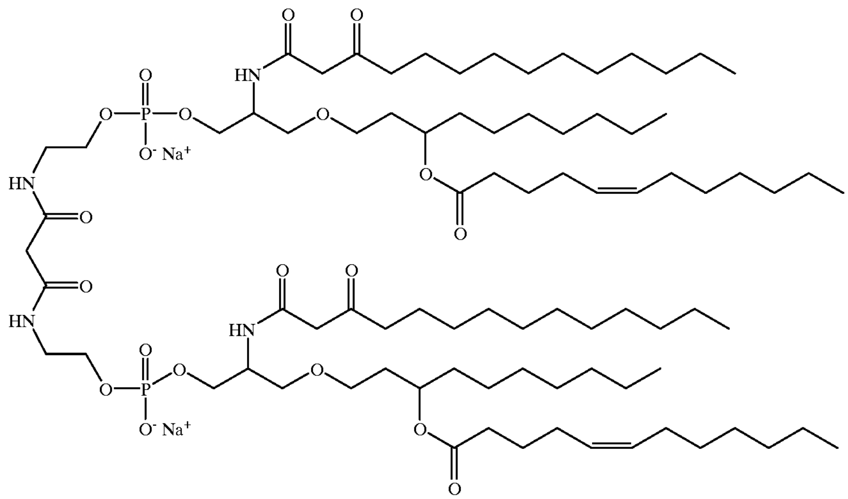 | 0.70 $\mu$M |
| 113665 | 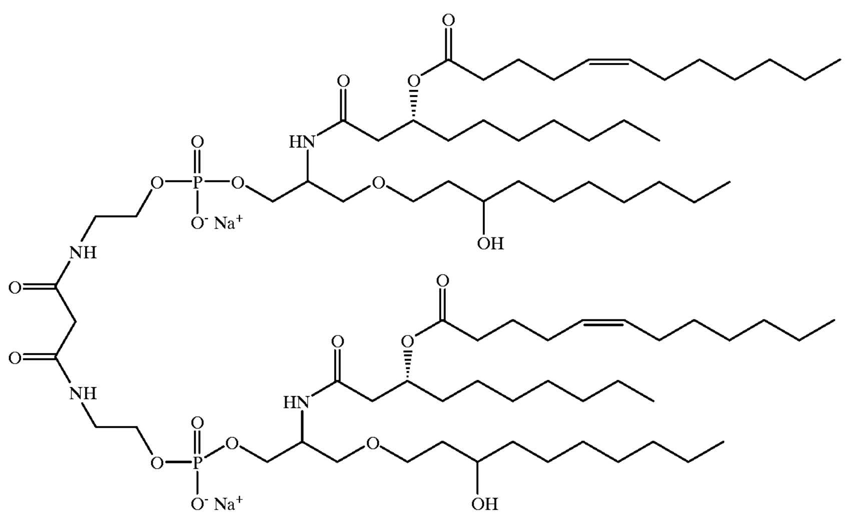 | |

TABLE 6-continued
WB ED$_{50}$ vs. % of LPS at 10 ng/ml
| ER# | Structure | WB ED$_{50}$ vs LPS @ 10 ng/ml |
|---|---|---|
| 113666 | 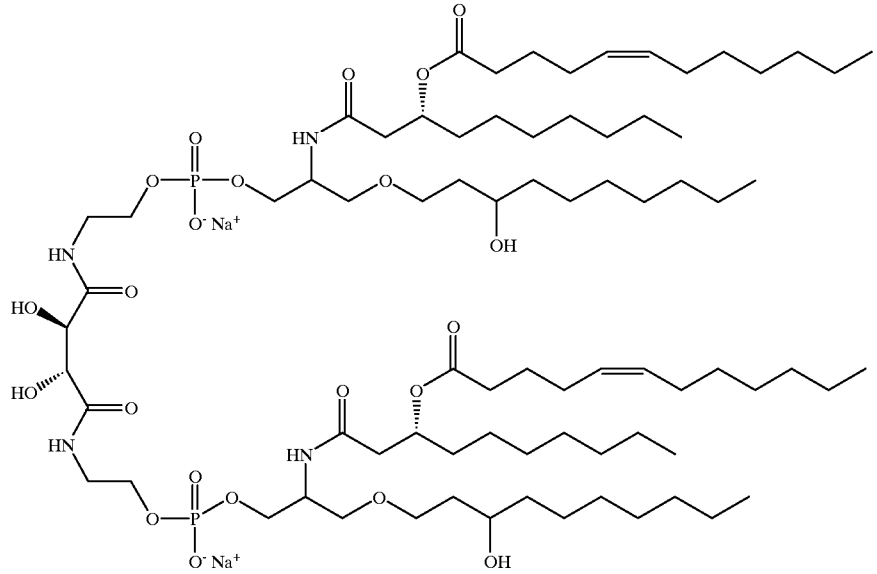 | |
| 118023 | 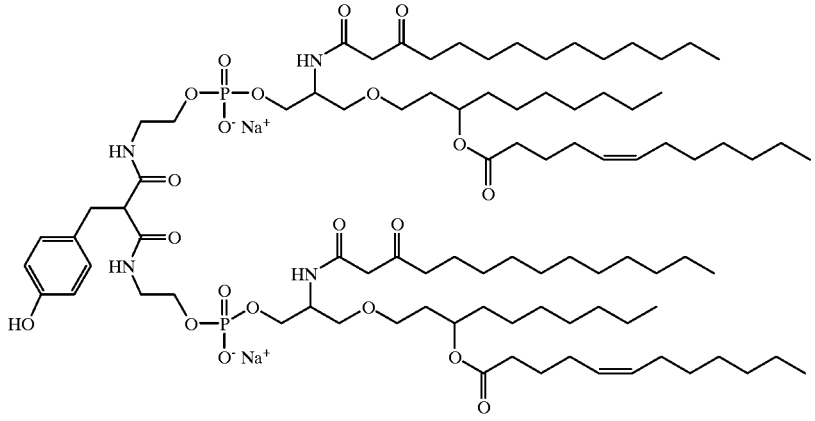 | |
| 019772 | 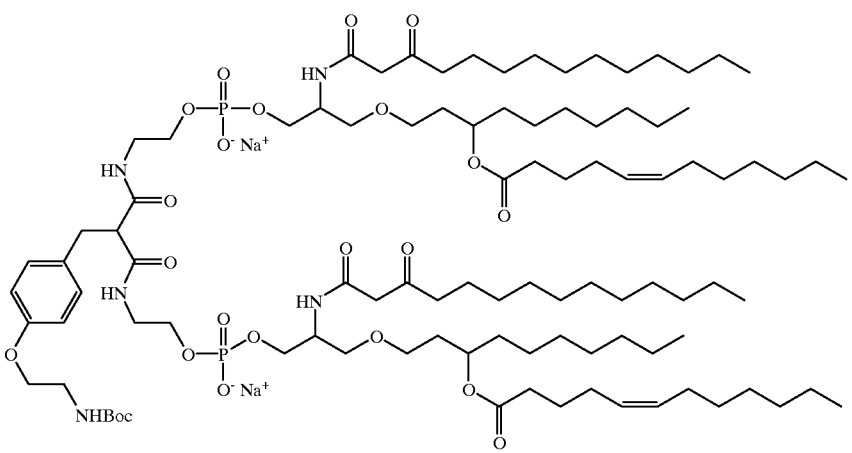 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 118989 | 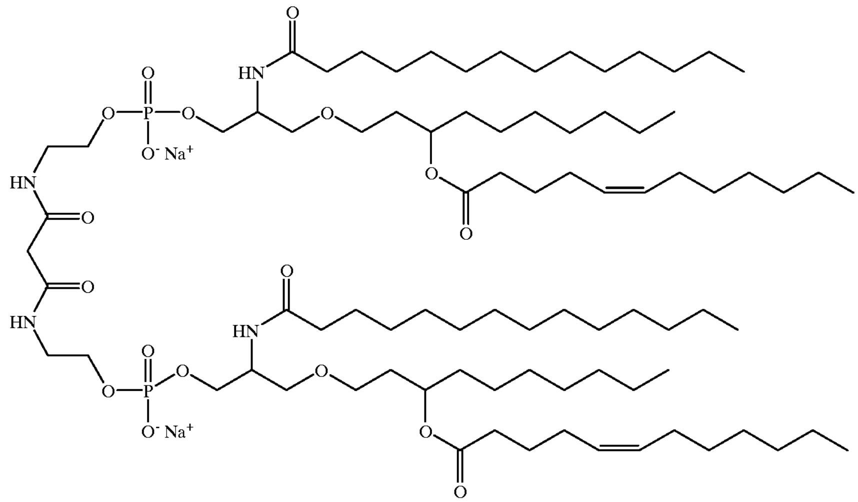 | 0.1 µM |
| 118999 | 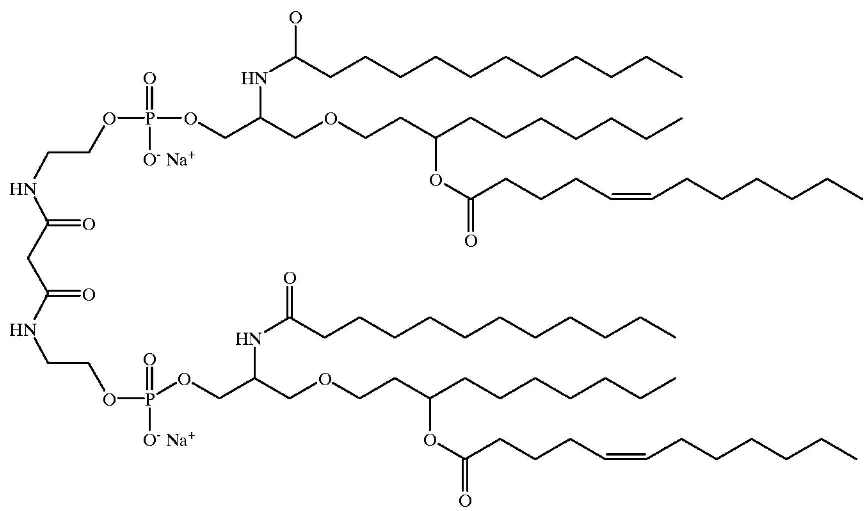 | |
| 119000 | 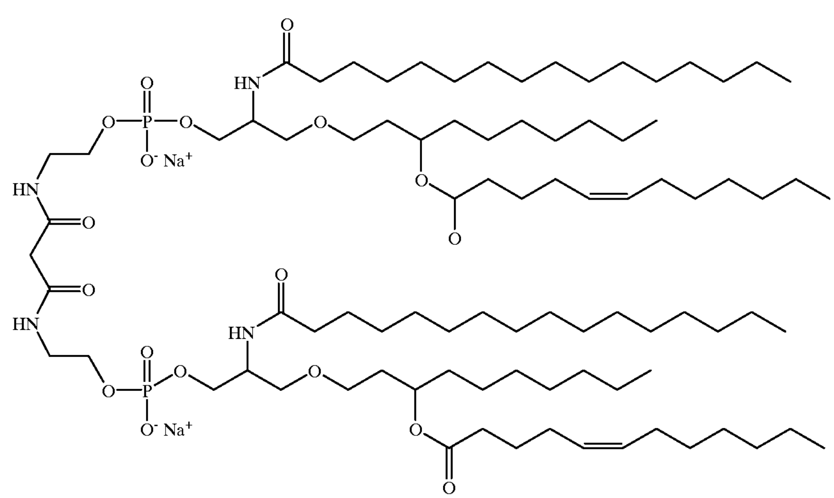 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 119001 | 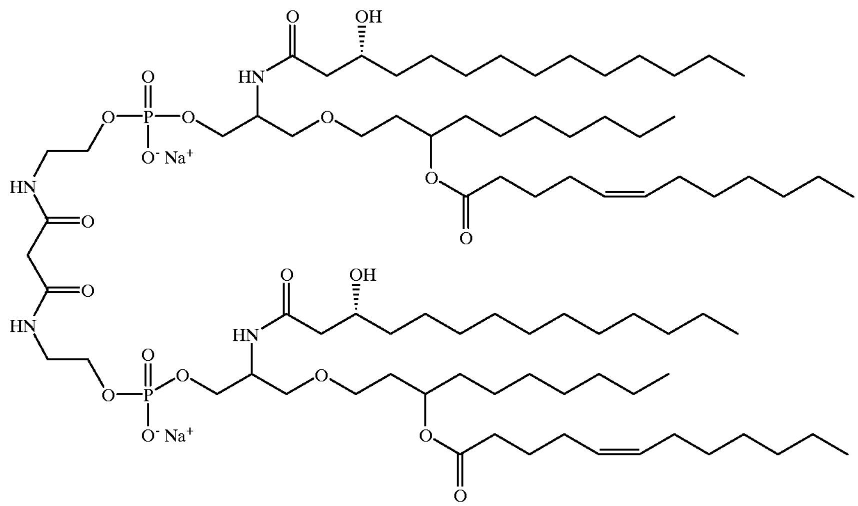 | 1.23 µM |
| 118949 | 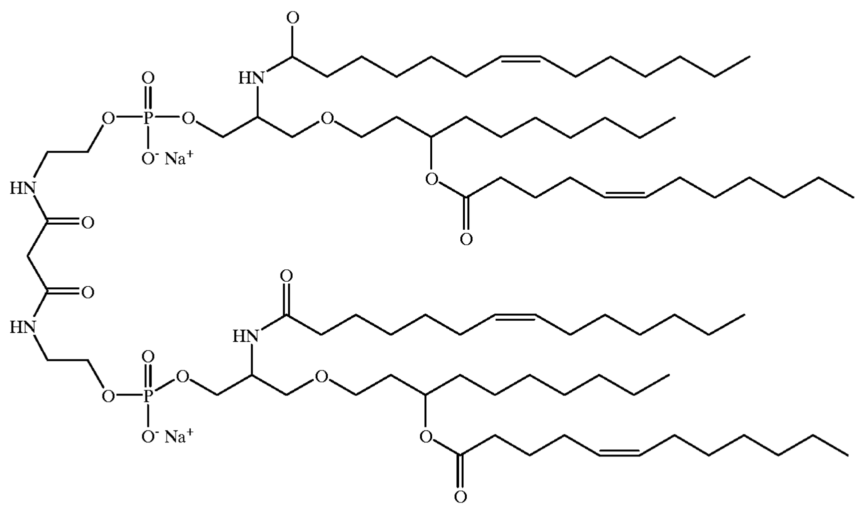 | |
| 119327 | 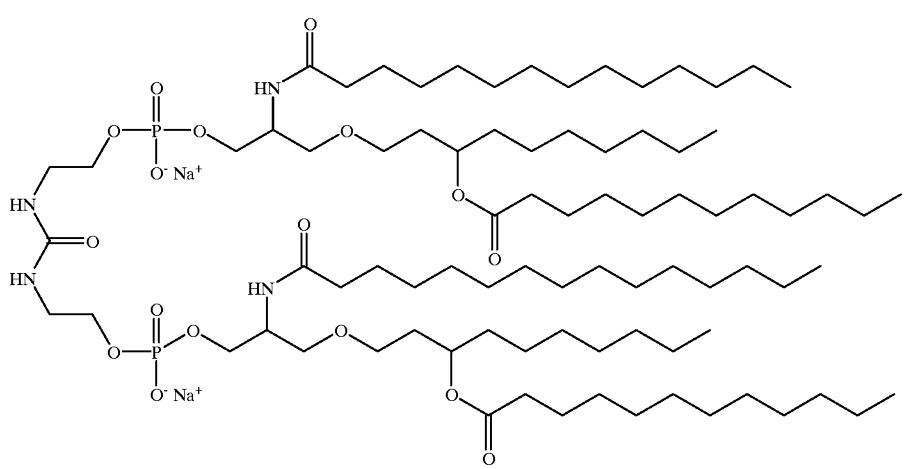 | 0.015 µM |

TABLE 6-continued

WB ED$_{50}$ vs. % of LPS at 10 ng/ml

| ER# | Structure | WB ED$_{50}$ vs LPS @ 10 ng/ml |
|---|---|---|
| 119328 | 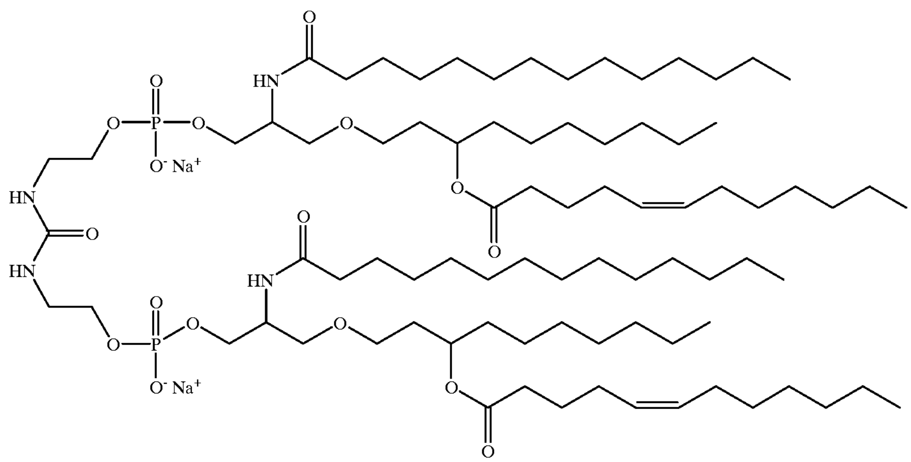 | >>10 μM |
| 119329 | 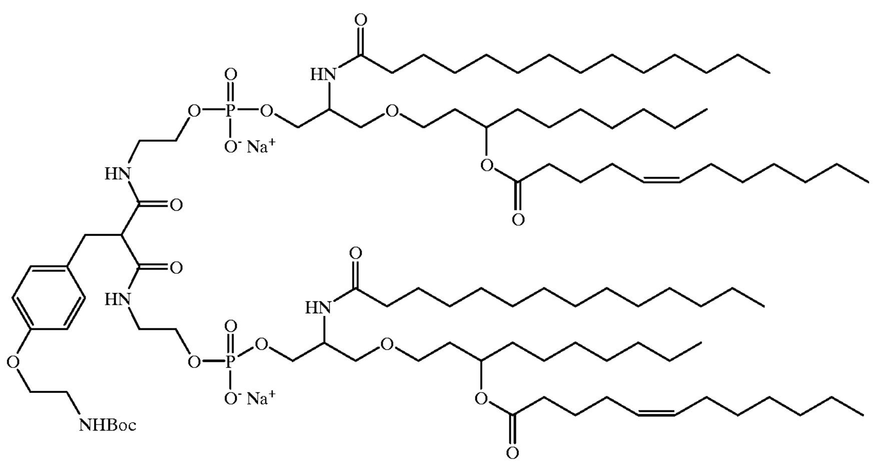 | |
| 119521 | 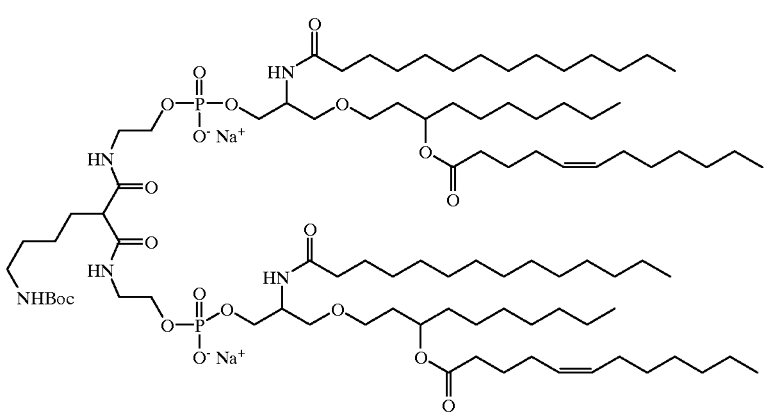 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 119522 | 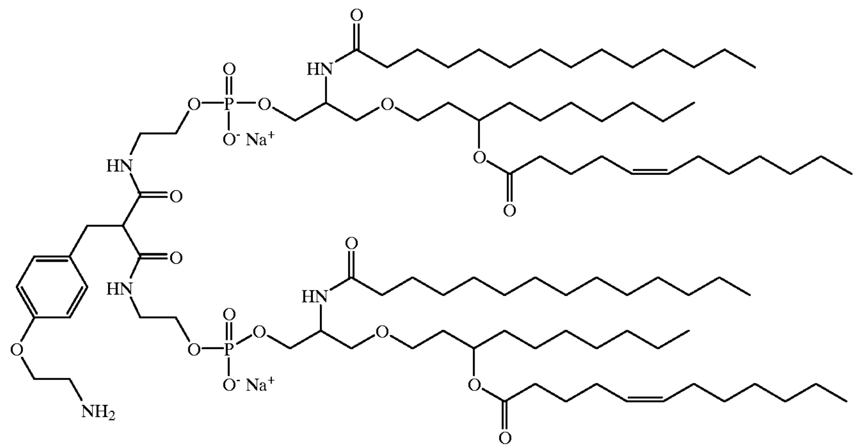 | |
| 119523 | 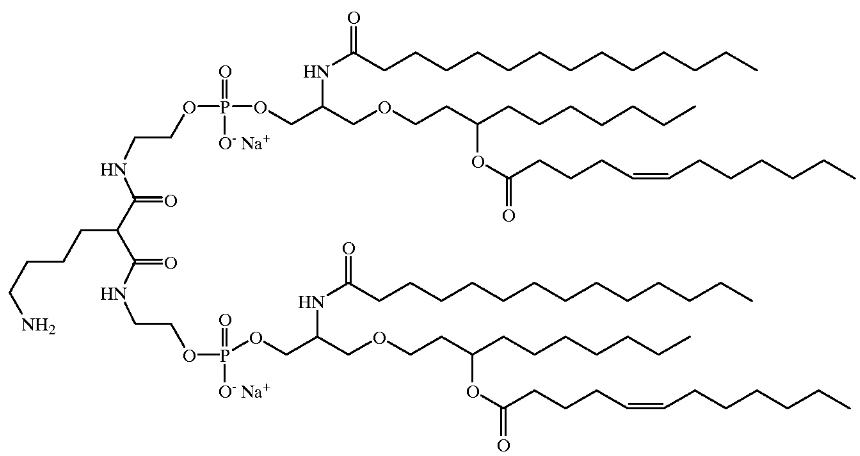 | |
| 803022 | 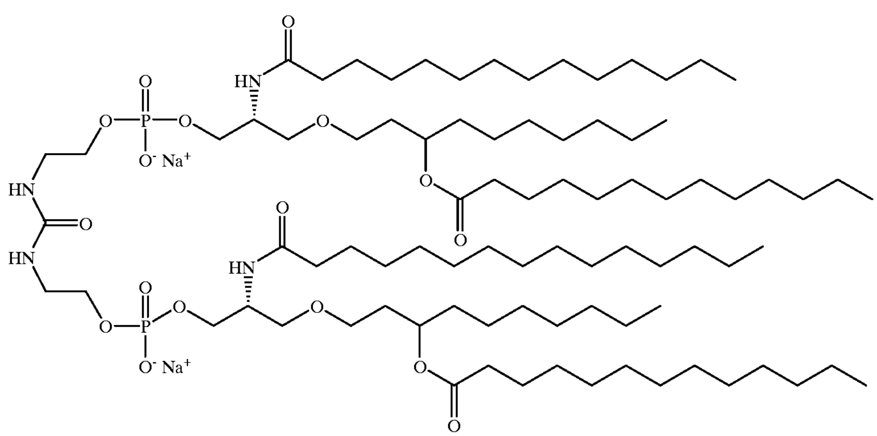 | 0.06 μM |

TABLE 6-continued

WB ED$_{50}$ vs. % of LPS at 10 ng/ml

| ER# | Structure | WB ED$_{50}$ vs LPS @ 10 ng/ml |
|---|---|---|
| 803028 | | |
| 803045 | | |
| 803056 | | |

TABLE 6-continued

WB ED$_{50}$ vs. % of LPS at 10 ng/ml

| ER# | Structure | WB ED$_{50}$ vs LPS @ 10 ng/ml |
|---|---|---|
| 803058 | | 0.022 μM |
| 803059 | | 0.89 μM |
| 803592 | | |

TABLE 6-continued

WB ED$_{50}$ vs. % of LPS at 10 ng/ml

| ER# | Structure | WB ED$_{50}$ vs LPS @ 10 ng/ml |
|---|---|---|
| 803596 | 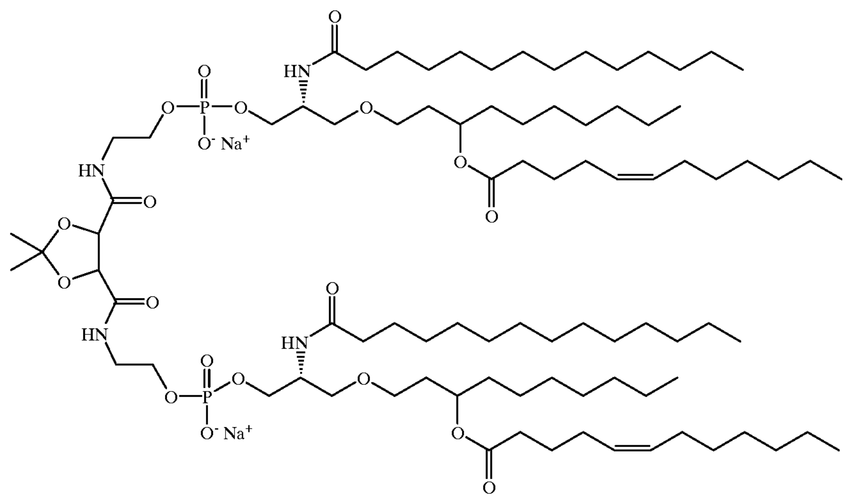 | |
| 803597 | 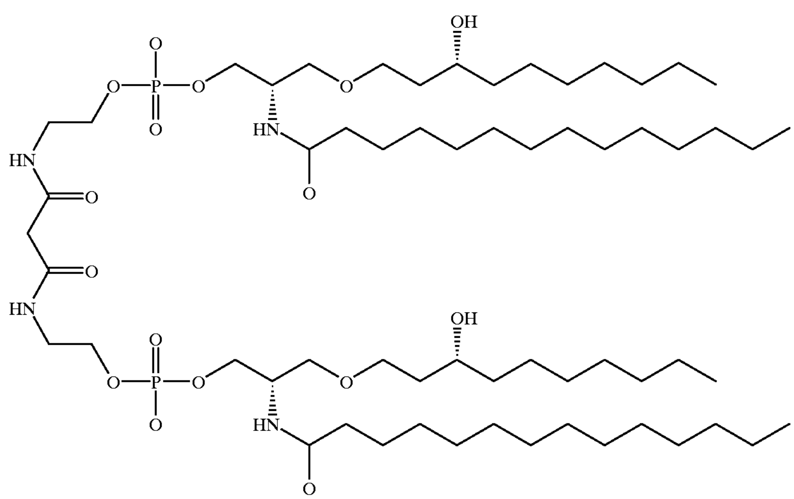 | |
| 803598 | 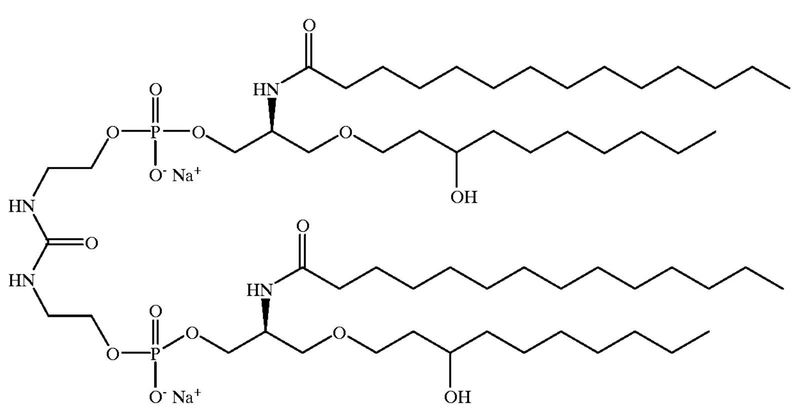 | |

TABLE 6-continued

WB ED$_{50}$ vs. % of LPS at 10 ng/ml

| ER# | Structure | WB ED$_{50}$ vs LPS @ 10 ng/ml |
|---|---|---|
| 803599 | 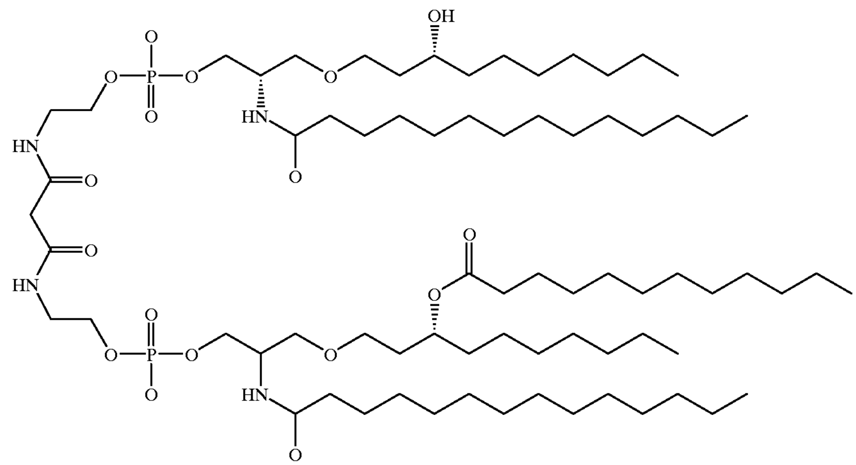 | |
| 803613 | 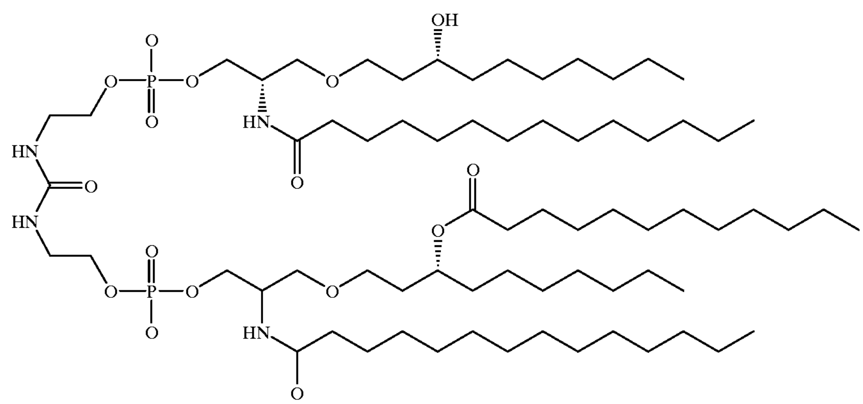 | |
| 803731 | 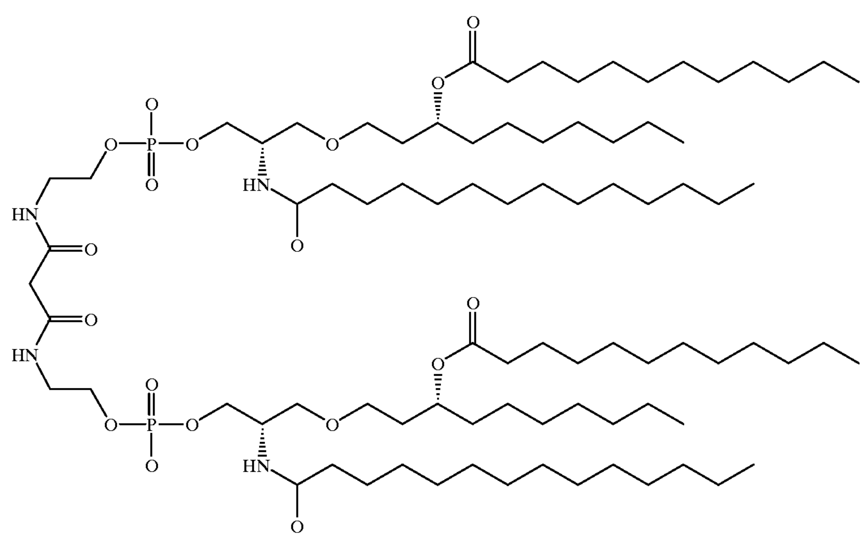 | >10 μM |

TABLE 6-continued

WB ED$_{50}$ vs. % of LPS at 10 ng/ml

| ER# | Structure | WB ED$_{50}$ vs LPS @ 10 ng/ml |
|---|---|---|
| 803732 | | 0.85 μM |
| 803733 | | 0.70 μM |
| 803751 | | |

TABLE 6-continued

WB ED$_{50}$ vs. % of LPS at 10 ng/ml

| ER# | Structure | WB ED$_{50}$ vs LPS @ 10 ng/ml |
|---|---|---|
| 803783 | 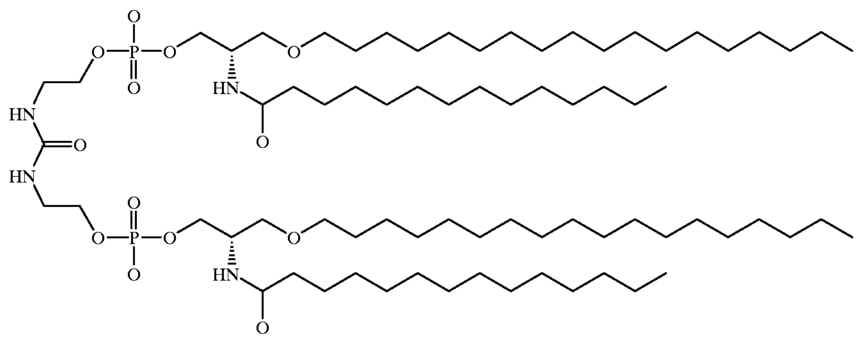 | |
| 803784 | 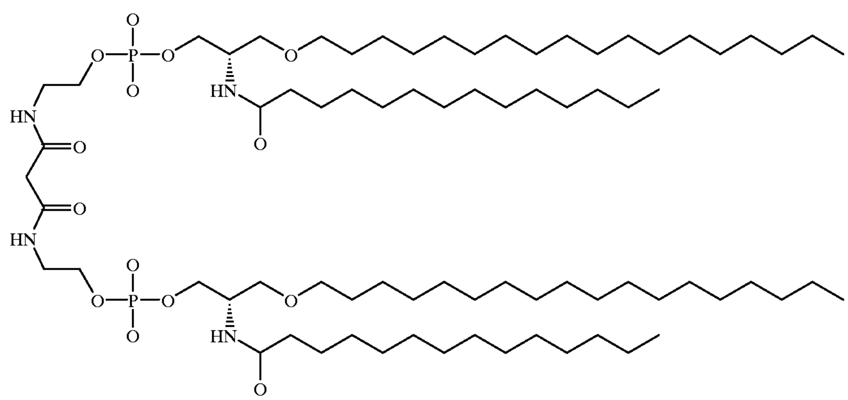 | |
| 803789 | 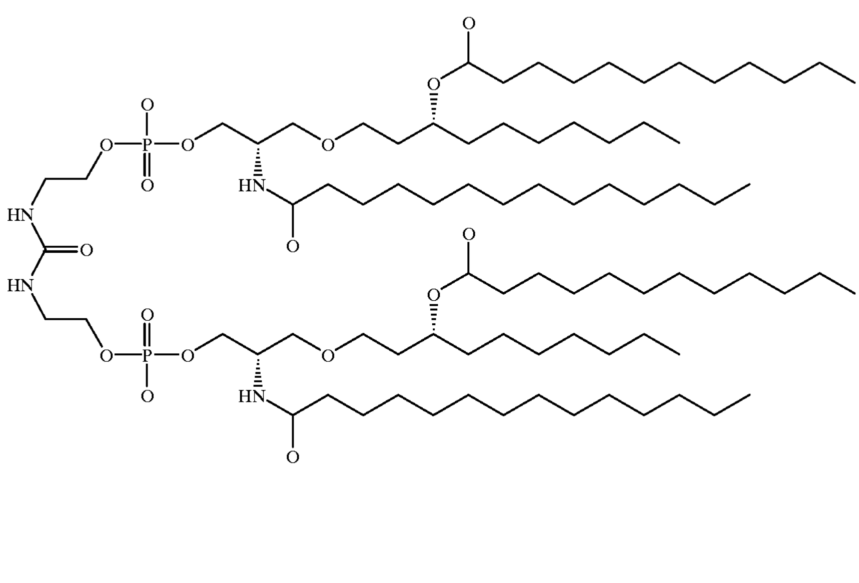 | 0.10 µM |

TABLE 6-continued
WB ED$_{50}$ vs. % of LPS at 10 ng/ml
| ER# | Structure | WB ED$_{50}$ vs LPS @ 10 ng/ml |
|---|---|---|
| 804053 | 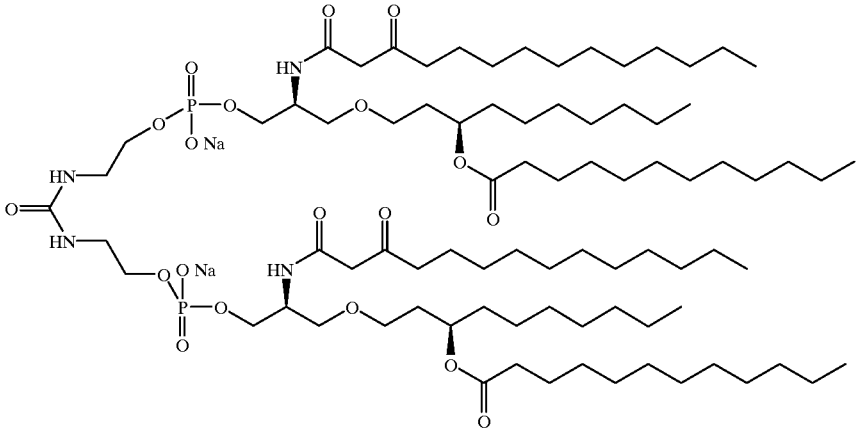 | 1.34 µM |
| 804057 | 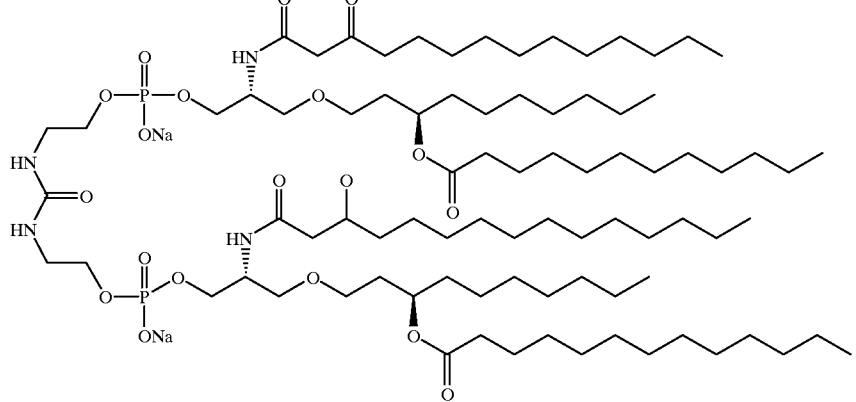 | 0.008 µM |
| 804058 | 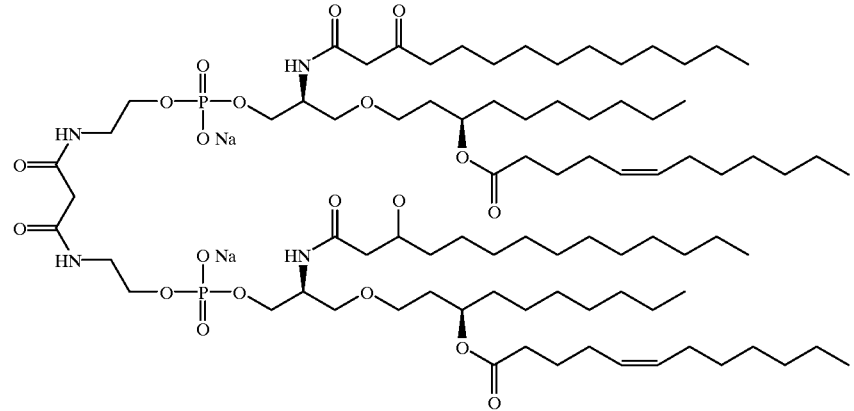 | 0.03 µM |

TABLE 6-continued
WB ED$_{50}$ vs. % of LPS at 10 ng/ml
| ER# | Structure | WB ED$_{50}$ vs LPS @ 10 ng/ml |
|---|---|---|
| 804059 | 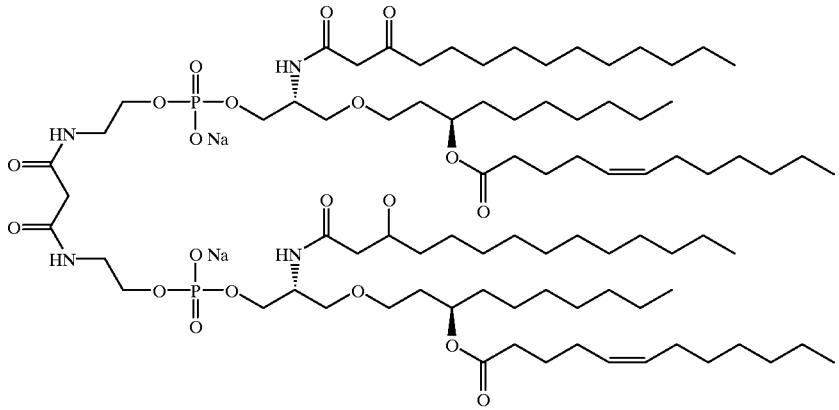 | >10 μM |
| 804061 | 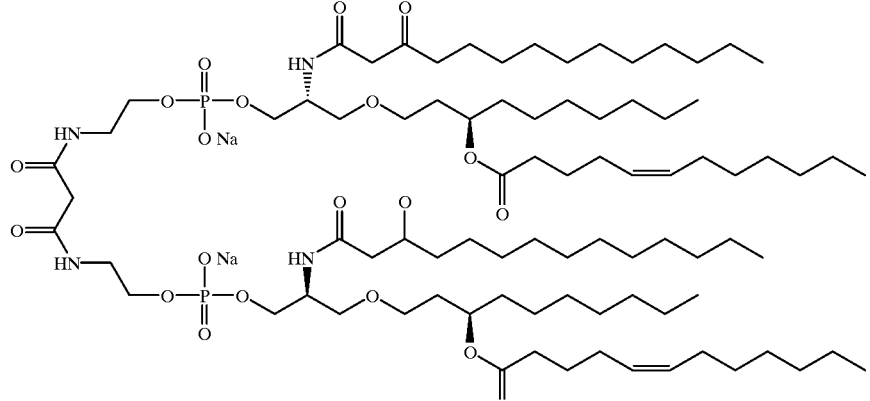 | 2.5 μM |
| 804097 | 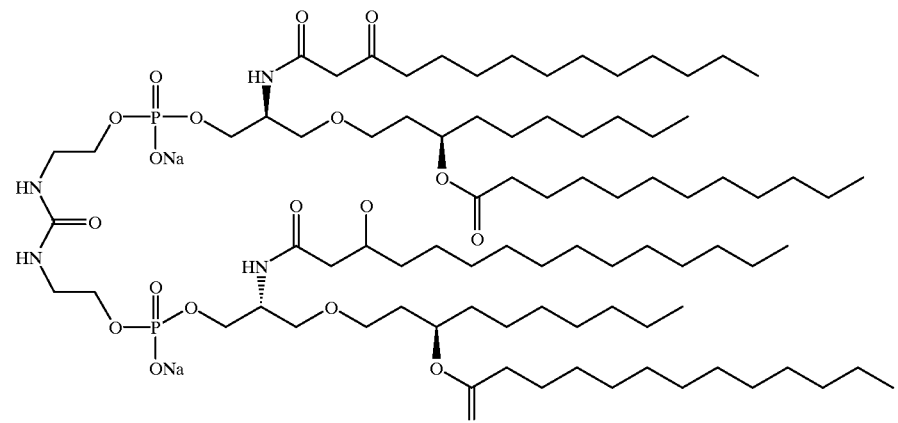 | 0.3 μM |

TABLE 6-continued

WB ED$_{50}$ vs. % of LPS at 10 ng/ml

| ER# | Structure | WB ED$_{50}$ vs LPS @ 10 ng/ml |
|---|---|---|
| 804121 | 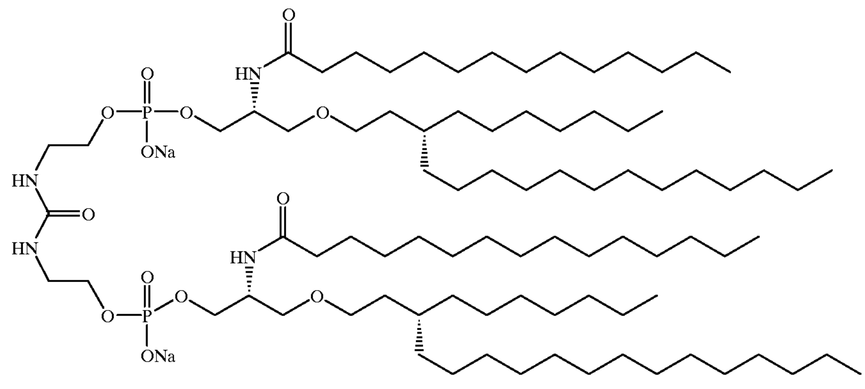 | 0.46 μM |
| 804130 | 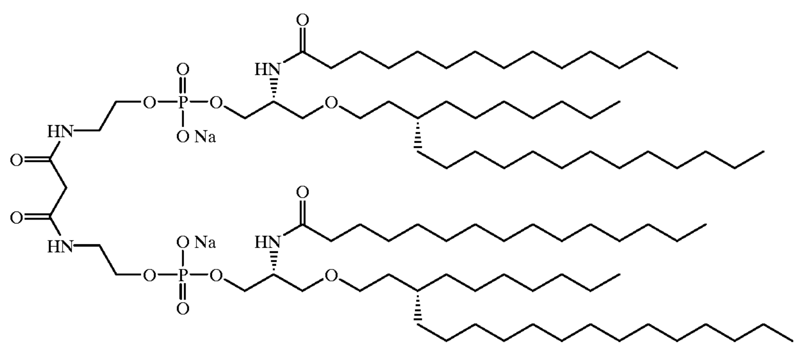 | 0.66 μM |
| 804221 | 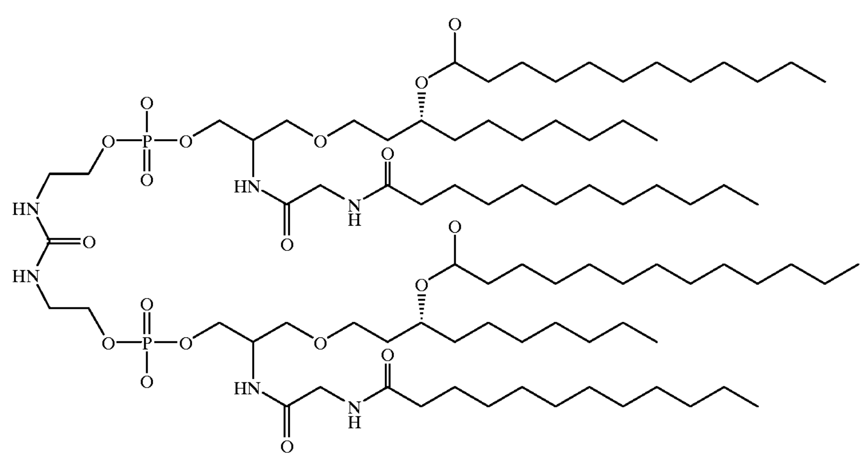 | 2.2 μM |

TABLE 6-continued

WB ED$_{50}$ vs. % of LPS at 10 ng/ml

| ER# | Structure | WB ED$_{50}$ vs LPS @ 10 ng/ml |
|---|---|---|
| 804222 | 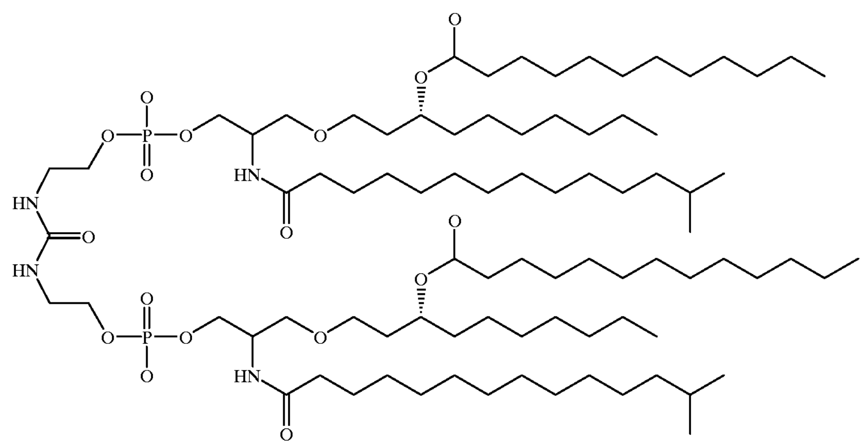 | 0.008 μM |
| 804252 | 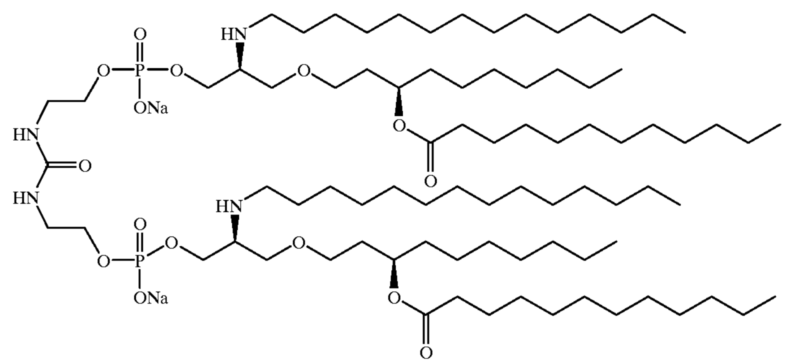 | 400 nM (576-021) + EtOH |
| 804253 | 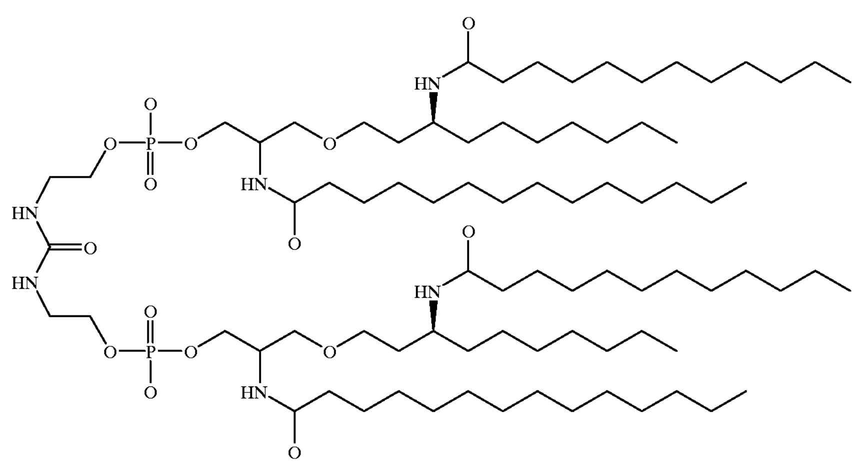 | >10 μM |

TABLE 6-continued
WB ED$_{50}$ vs. % of LPS at 10 ng/ml
| ER# | Structure | WB ED$_{50}$ vs LPS @ 10 ng/ml |
|---|---|---|
| 804281 | 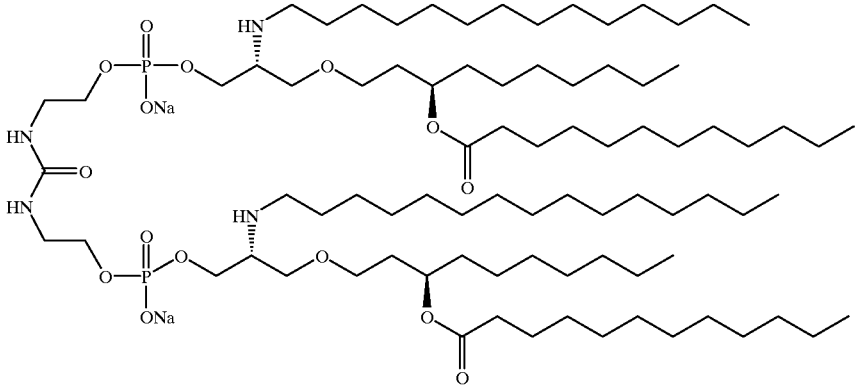 | 0.45 μM |
| 804313 | 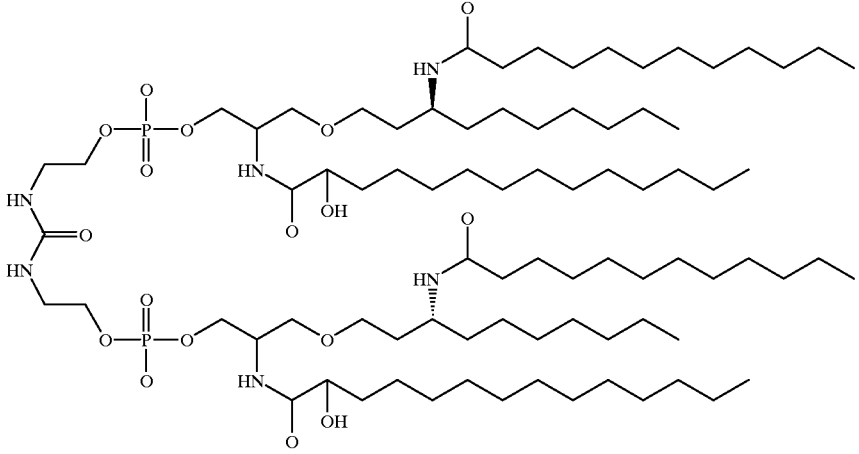 | 0.014 μM |
| 804339 | 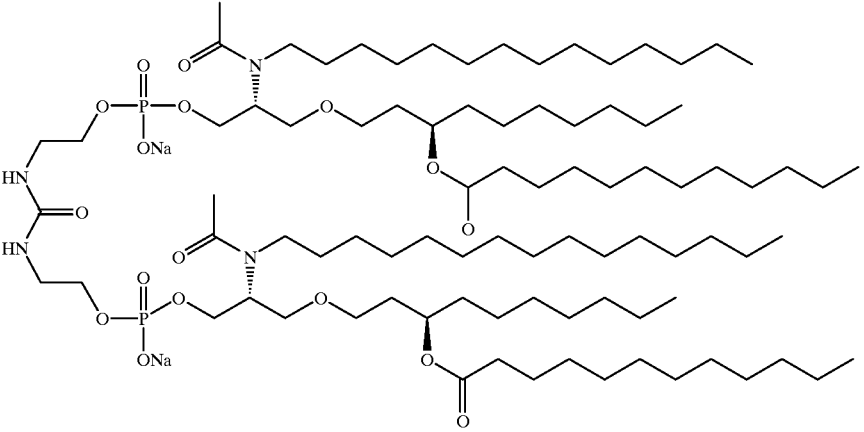 | 1.06 μM |

TABLE 6-continued

WB ED$_{50}$ vs. % of LPS at 10 ng/ml

| ER# | Structure | WB ED$_{50}$ vs LPS @ 10 ng/ml |
|---|---|---|
| 804372 | 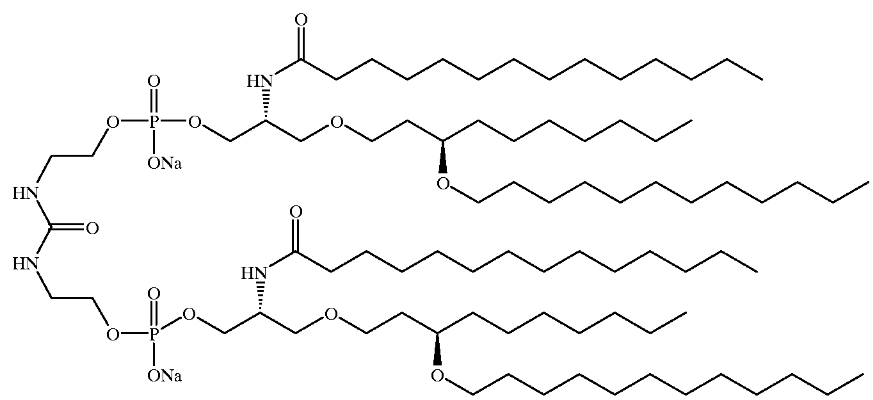 | 0.4 μM |
| 804442 | 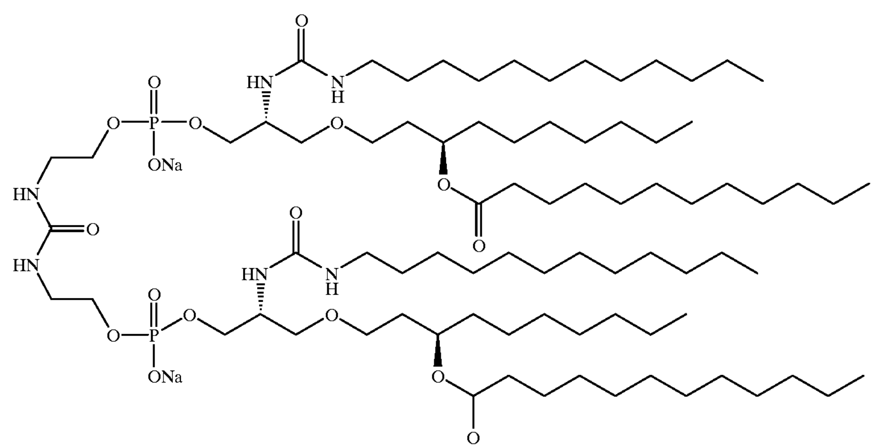 | 0.007 μM |
| 804503 | 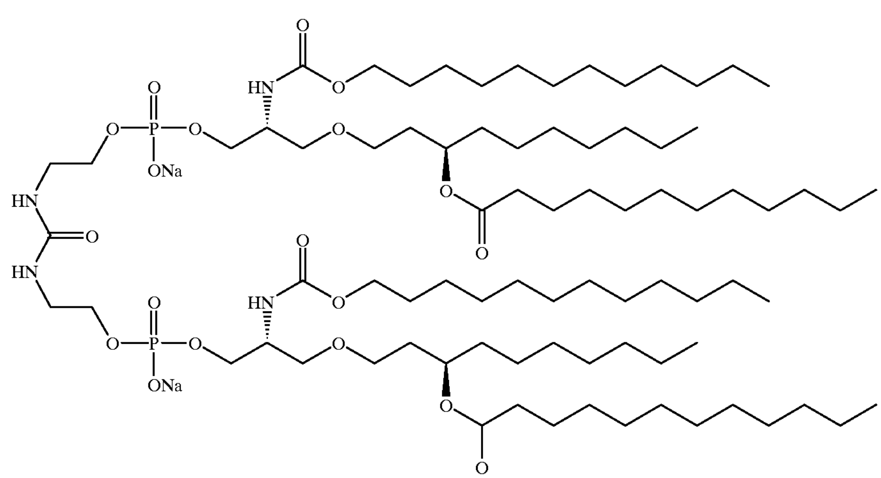 | 0.35 μM |

TABLE 6-continued

WB ED$_{50}$ vs. % of LPS at 10 ng/ml

| ER# | Structure | WB ED$_{50}$ vs LPS @ 10 ng/ml |
|---|---|---|
| 804558 | 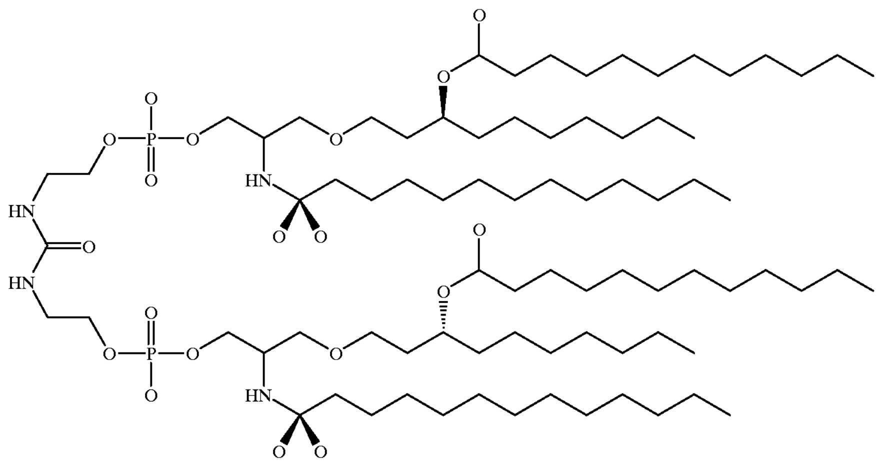 | 0.16 µM |
| 804596 | 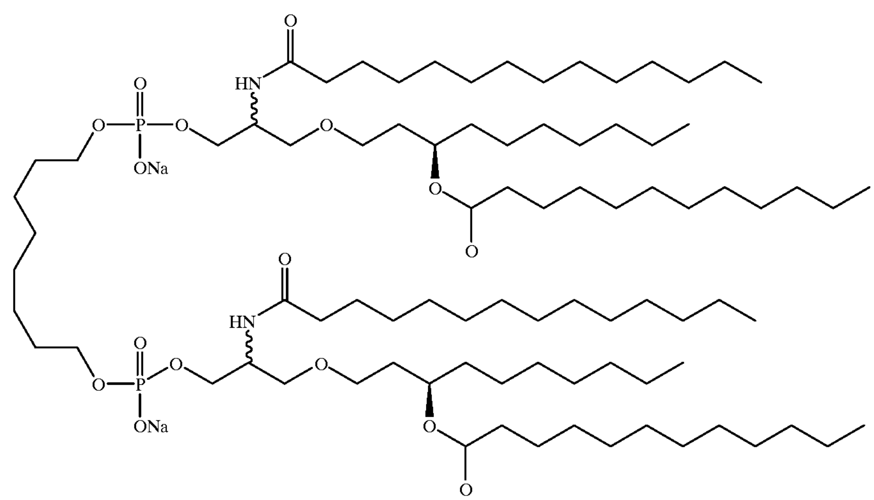 | >10 µM |
| 804674 | 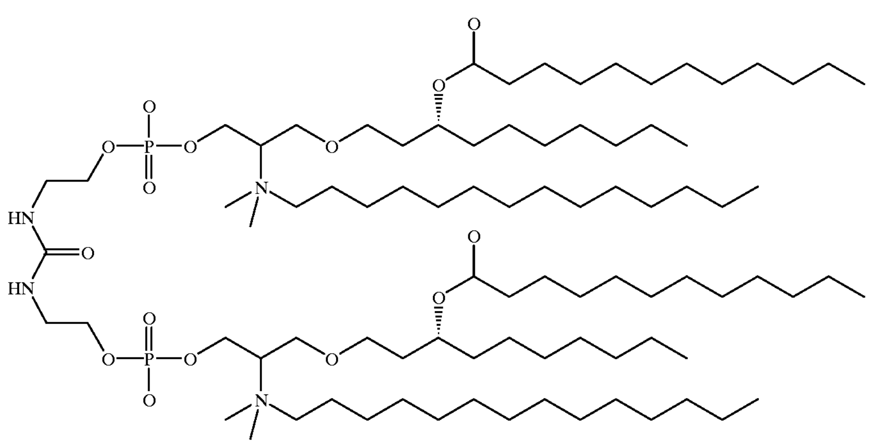 | 1.2 µM |

TABLE 6-continued
WB ED$_{50}$ vs. % of LPS at 10 ng/ml
| ER# | Structure | WB ED$_{50}$ vs LPS @ 10 ng/ml |
|---|---|---|
| 804678 | 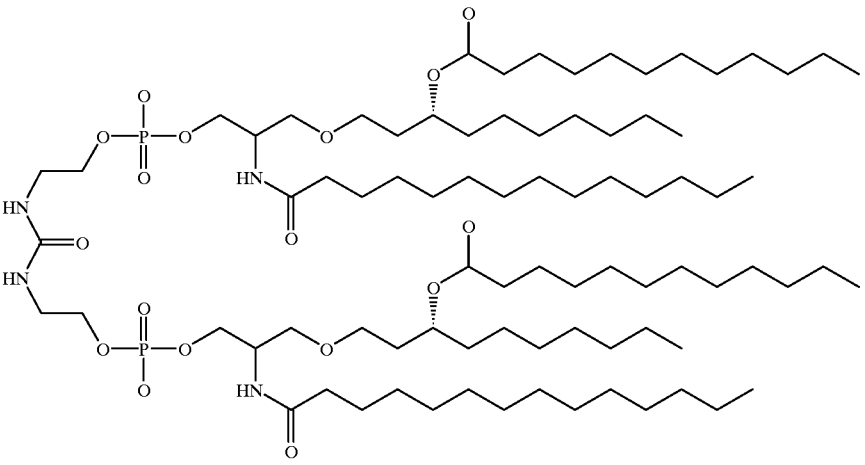 | 0.018 $\mu$M |
| 804679 | 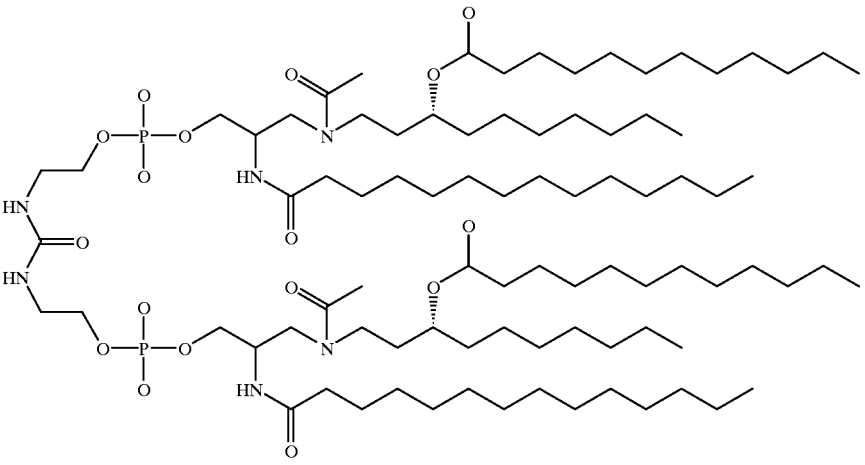 | 0.53 $\mu$M |
| 804680 | 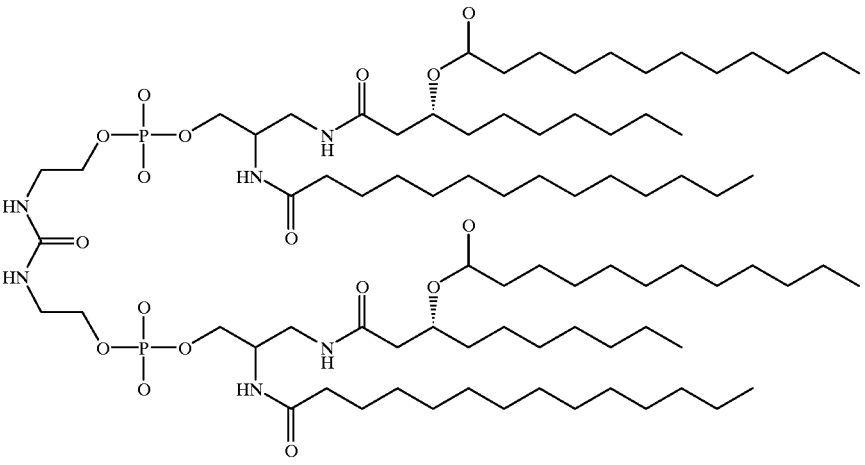 | 0.015 $\mu$M |

TABLE 6-continued
WB ED$_{50}$ vs. % of LPS at 10 ng/ml
| ER# | Structure | WB ED$_{50}$ vs LPS @ 10 ng/ml |
|---|---|---|
| 804732 | 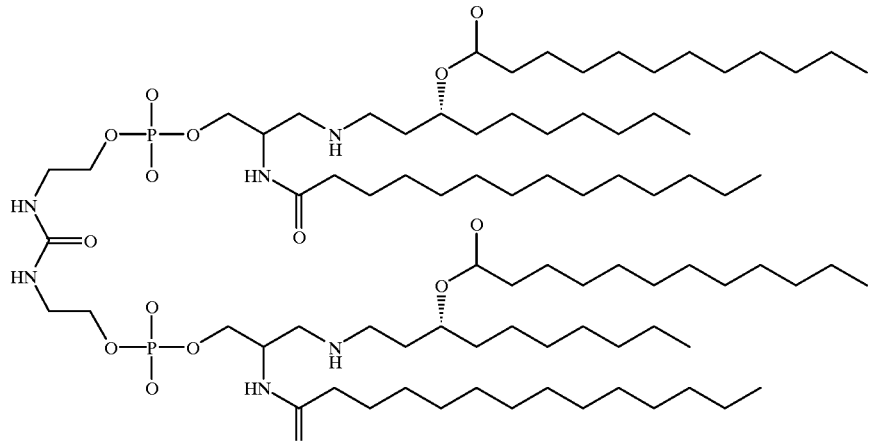 | <0.001 μM |
| 804764 | 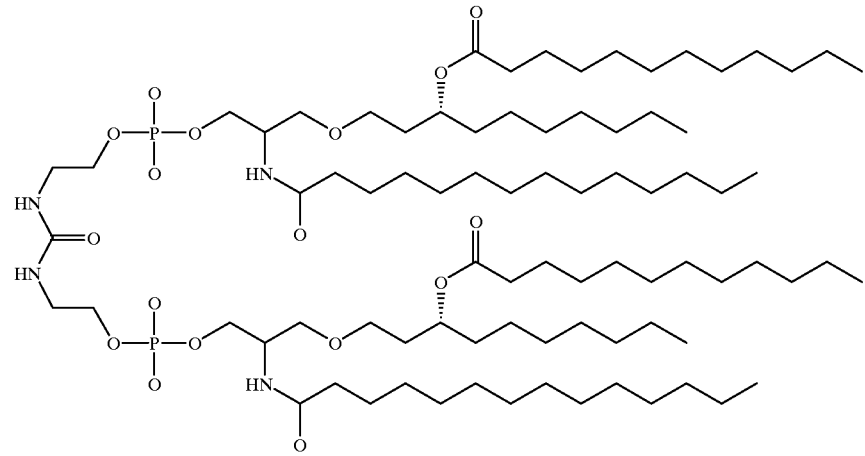 | 0.015 μM |

TABLE 6-continued
WB ED$_{50}$ vs. % of LPS at 10 ng/ml
| ER# | Structure | WB ED$_{50}$ vs LPS @ 10 ng/ml |
|---|---|---|
| 804772 | 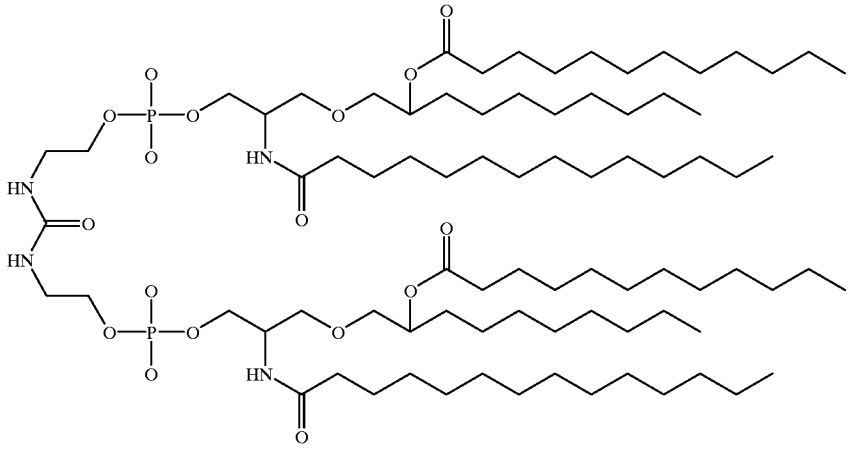 | 0.008 μM |
| 804947 | 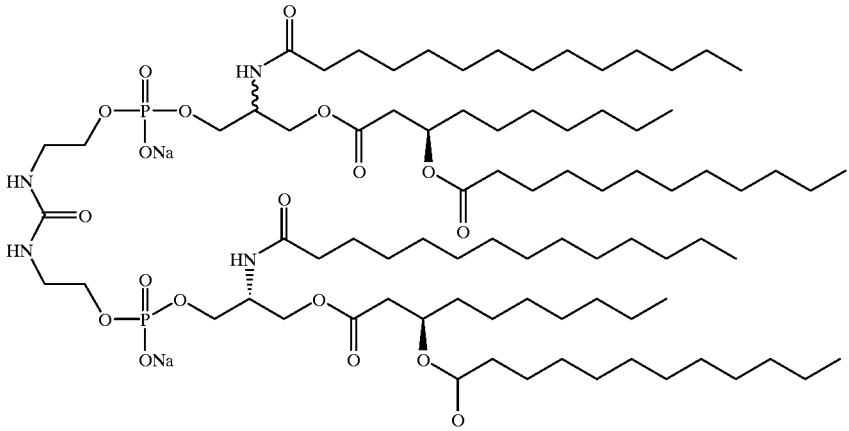 | >>10 μM |
Table 7 below contains the compound number as referenced herein to the corresponding ER number.
TABLE 7
Correspondence of Compound Nos. to ER Nos.
| Compound # | ER # |
|---|---|
| 16 | 112048 |
| 31 | 803058 |
| 48 | 803733 |
| 50 | 803022 |
| 62 | 803789 |
| 72 | 803592 |
| 100 | 112022 |
| 102 | 111230 |
| 104 | 111231 |
| 106 | 111232 |
| 108 | 111233 |
| 110 | 112043 |
| 112 | 112047 |
| 114 | 112047 |
| 116 | 112048 |
| 118 | 112049 |
| 120 | 112063 |
| 122 | 112064 |
TABLE 7-continued
Correspondence of Compound Nos. to ER Nos.
| Compound # | ER # |
|---|---|
| 124 | 112065 |
| 126 | 112066 |
| 128 | 112071 |
| 130 | 112072 |
| 132 | 112091 |
| 134 | 112092 |
| 136 | 112093 |
| 138 | 112098 |
| 140 | 112099 |
| 142 | 112100 |
| 146 | 112859 |
| 148 | 112860 |
| 150 | 112861 |
| 152 | 113634 |
| 154 | 113635 |
| 156 | 113643 |
| 158 | 113644 |
| 160 | 113651 |
| 164 | 113665 |
| 166 | 113666 |

TABLE 7-continued

Correspondence of Compound Nos. to ER Nos.

| Compound # | ER # |
|---|---|
| 168 | 118023 |
| 170 | 019772 |
| 172 | 118989 |
| 176 | 118999 |
| 178 | 119000 |
| 180 | 119001 |
| 182 | 118949 |
| 184 | 119327 |
| 186 | 119328 |
| 188 | 119329 |
| 190 | 119521 |
| 192 | 119522 |
| 194 | 119523 |
| 196 | 803022 |
| 198 | 803045 |
| 200 | 803056 |
| 202 | 803058 |
| 204 | 803059 |
| 206 | 803592 |

What is claimed is:

1. A compound of the formula I

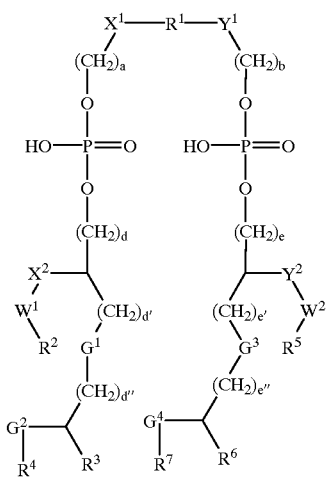

wherein:

$R^1$ is selected from the group consisting of (a) C(O);

(b) C(O)—$C_{1-14}$ alkyl-C(O), wherein said $C_{1-14}$ alkyl is optionally substituted with hydroxy, $C_{1-5}$ alkoxy, $C_{1-5}$ alkylenedioxy, $C_{1-5}$ alkylamino, or $C_{1-5}$-alkyl-aryl, wherein said aryl moiety of said $C_{1-5}$-alkyl-aryl is optionally substituted with $C_{1-5}$ alkoxy, $C_{1-5}$ alkylamino, $C_{1-5}$ alkoxy-amino, $C_{1-5}$ alkylamino-$C_{1-5}$ alkoxy, —O—$C_{1-5}$ alkylamino-$C_{1-5}$ alkoxy, —O—$C_{1-5}$ alkylamino-C(O)—$C_{1-5}$ alkyl C(O)OH, —O—$C_{1-5}$ alkylamino-C(O)—$C_{1-5}$ alkyl-C(O)—$C_{1-5}$ alkyl;

(c) $C_2$ to $C_{15}$ straight or branched chain alkyl optionally substituted with hydroxy or alkoxy; and (d) —C(O)—$C_{6-12}$ arylene-C(O)— wherein said arylene is optionally substituted with hydroxy, halogen, nitro or amino;

a and b are independently 0, 1, 2, 3 or 4;

d, d', d", e, e' and e" are independently an integer from 1 to 4;

$X^1$, $X^2$, $Y^1$ and $Y^2$ are independently selected from the group consisting of a null, oxygen, NH and N(C(O)$C_4$ alkyl), and N($C_{1-4}$ alkyl)$_2$;

$W^1$ and $W^2$ are independently selected from the group consisting of carbonyl, methylene, sulfone and sulfoxide;

$R^2$ and $R^5$ are independently selected from the group consisting of:

(a) $C_2$ to $C_{20}$ straight chain or branched chain alkyl which is optionally substituted with oxo, hydroxy or alkoxy, (b) $C_2$ to $C_{20}$ straight chain or branched chain alkenyl or dialkenyl which is optionally substituted with oxo, hydroxy or alkoxy;

(c) $C_2$ to $C_{20}$ straight chain or branched chain alkoxy which is optionally substituted with oxo, hydroxy or alkoxy;

(d) —NH—$C_2$ to $C_{20}$ straight chain or branched chain alkyl, wherein said alkyl group is optionally substituted with oxo, hydroxy or alkoxy; and (e)

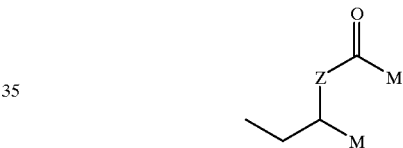

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;

$R^3$ and $R^6$ are independently selected from the group consisting of $C_2$ to $C_{20}$ straight chain or branched chain alkyl or alkenyl optionally substituted with oxo or fluoro;

$R^4$ and $R^7$ are independently selected from the group consisting of C(O)$C_2$ to $C_{20}$ straight chain or branched chain alkyl or alkenyl; $C_2$ to $C_{20}$ straight chain or branched chain alkyl; $C_2$ to $C_{20}$ straight chain or branched chain alkoxy; $C_2$ to $C_{20}$ straight chain or branched chain alkenyl; wherein said alkyl, alkenyl or alkoxy groups can be independently and optionally substituted with hydroxy, fluoro or $C_1$ to $C_5$ alkoxy;

$G^1$, $G^2$, $G^3$ and $G^4$ are independently selected from the group consisting of oxygen, methylene, amino, thiol, —NHC(O)—, and —N(C(O)$C_{1-4}$ alkyl)—;

or $G^2R^4$ or $G^4R^7$ may together be a hydrogen atom or hydroxyl;

or a pharmaceutically acceptable salt thereof;
with the proviso that the compound is not

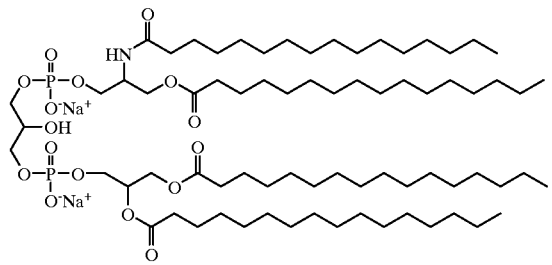

or

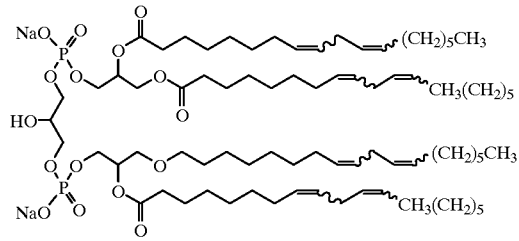

2. A compound of claim 1 wherein R' is selected from the group consisting of C(O) and C(O)—C$_{1-14}$ alkyl-C(O).

3. A compound of claim 2 wherein R$^1$ is C(O)—C$_{1-14}$ alkyl-C(O).

4. A compound of claim 1 wherein each of a and b are 2.

5. A compound of claim 1 wherein X$^1$ and Y$^1$ are both NH.

6. A compound of claim 1 wherein d and e are 1.

7. A compound of claim 1 wherein G$^2$R$^4$ and G$^4$R$^7$ are both hydroxy.

8. A compound of claim 1 which is selected from the group consisting of ER 803022, ER 803058, ER 803732, ER 804053, ER 804057, ER 804058, ER 804059, ER 804442, ER 804680 and ER 804764.

9. An immunological adjuvant formulation comprising a compound of the formula I

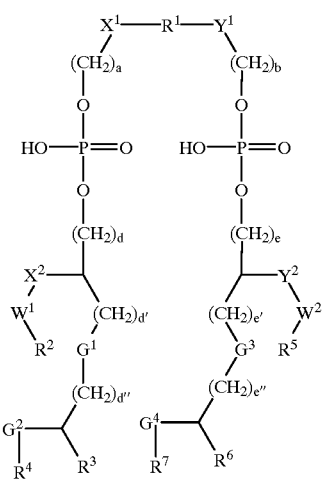

wherein:
R$^1$ is selected from the group consisting of
(a) C(O);
(b) C(O)—C$_{1-14}$ alkyl-C(O), wherein said C$_{1-14}$ alkyl is optionally substituted with hydroxy, C$_{1-5}$ alkoxy, C$_{1-5}$ alkylenedioxy, C$_{1-5}$ alkylamino, or C$_{1-5}$-alkyl-aryl, wherein said aryl moiety of said C$_{1-5}$-alkyl-aryl is optionally substituted with C$_{1-5}$ alkoxy, C$_{1-5}$ alkylamino, C$_{1-5}$ alkoxy-amino, C$_{1-5}$ alkylamino-C$_{1-5}$ alkoxy, —O—C$_{1-5}$ alkylamino-C$_{1-5}$ alkoxy, —O—C$_{1-5}$ alkylamino-C(O)—C$_{1-5}$ alkyl C(O)OH, —O—C$_{1-5}$ alkylamino-C(O)—C$_{1-5}$ alkyl-C(O)—C$_{1-5}$ alkyl;

(c) C$_2$ to C$_{15}$ straight or branched chain alkyl optionally substituted with hydroxy or alkoxy; and (d) —C(O)—C$_{6-12}$ arylene-C(O)— wherein said arylene is optionally substituted with hydroxy, halogen, nitro or amino;

a and b are independently 0, 1, 2, 3 or 4;

d, d', d'', e, e' and e'' are independently an integer from 1 to 4;

X$^1$, X$^2$, Y$^1$ and Y$^2$ are independently selected from the group consisting of a null, oxygen, NH and N(C(O)C$_{1-4}$ alkyl), and N(C$_{1-4}$ alkyl)$_2$;

W$^1$ and W$^2$ are independently selected from the group consisting of carbonyl, methylene, sulfone and sulfoxide;

R$^2$ and R$^5$ are independently selected from the group consisting of:
(a) C$_2$ to C$_{20}$ straight chain or branched chain alkyl which is optionally substituted with oxo, hydroxy or alkoxy,
(b) C$_2$ to C$_{20}$ straight chain or branched chain alkenyl or dialkenyl which is optionally substituted with oxo, hydroxy or alkoxy;
(c) C$_2$ to C$_{20}$ straight chain or branched chain alkoxy which is optionally substituted with oxo, hydroxy or alkoxy;
(d) —NH—C$_2$ to C$_{20}$ straight chain or branched chain alkyl, wherein said alkyl group is optionally substituted with oxo, hydroxy or alkoxy; and
(e)

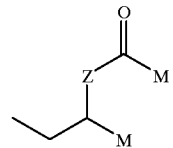

wherein Z is selected from the group consisting of O and NH, and M and N are independently selected from the group consisting of C$_2$ to C$_{20}$ straight chain or branched chain alkyl, alkenyl, alkoxy, acyloxy, alkylamino, and acylamino;

R$^3$ and R$^6$ are independently selected from the group consisting of C$_2$ to C$_{20}$ straight chain or branched chain alkyl or alkenyl optionally substituted with fluoro or oxo;

R$^4$ and R$^7$ are independently selected from the group consisting of C(O)C$_2$ to C$_{20}$ straight chain or branched chain alkyl or alkenyl; C$_2$ to C$_{20}$ straight chain or branched chain alkyl; C$_2$ to C$_{20}$ straight chain or branched chain alkoxy; C$_2$ to C$_{20}$ straight chain or branched chain alkenyl; wherein said alkyl, alkenyl or alkoxy groups can be independently and optionally substituted with hydroxy, fluoro or C$_1$ to C$_5$ alkoxy;

G$^1$, G$^2$, G$^3$ and G$^4$ are independently selected from the group consisting of oxygen, methylene, amino, thiol, —NHC(O)—, and —N(C(O)C$_{1-4}$ alkyl)—;

or $G^2R^4$ or $G^4R^7$ may together be a hydrogen atom or hydroxyl;

or a pharmaceutically acceptable salt thereof.

10. A vaccine formulation comprising an antigen and an adjuvant compound of formula I $$\begin{array}{c}
X^1\text{---}R^1\text{---}Y^1 \\
(CH_2)_a \qquad (CH_2)_b \\
O \qquad O \\
HO\text{---}P\text{=}O \qquad HO\text{---}P\text{=}O \\
O \qquad O \\
(CH_2)_d \qquad (CH_2)_e \\
X^2 \qquad Y^2 \\
W^1 \quad (CH_2)_{d'} \qquad (CH_2)_{e'} \quad W^2 \\
R^2 \quad G^1 \qquad G^3 \quad R^5 \\
(CH_2)_{d''} \qquad (CH_2)_{e''} \\
G^2 \qquad G^4 \\
R^4 \quad R^3 \qquad R^7 \quad R^6
\end{array}$$

wherein:

$R^1$ is selected from the group consisting of (a) C(O);

(b) C(O)—$C_{1-14}$ alkyl-C(O), wherein said $C_{1-14}$ alkyl is optionally substituted with hydroxy, $C_{1-5}$ alkoxy, $C_{1-5}$ alkylenedioxy, $C_{1-5}$ alkylamino, or $C_{1-5}$-alkyl-aryl, wherein said aryl moiety of said $C_{1-5}$-alkyl-aryl is optionally substituted with $C_{1-5}$ alkoxy, $C_{1-5}$ alkyl-amino, $C_{1-5}$ alkoxy-amino, $C_{1-5}$ alkylamino-$C_{1-5}$ alkoxy, —O—$C_{1-5}$ alkylamino-$C_{1-5}$ alkoxy, —O—$C_{1-5}$ alkylamino-C(O)—$C_{1-5}$ alkyl C(O)OH, —O—$C_{1-5}$ alkylamino-C(O)—$C_{1-5}$ alkyl-C(O)—$C_{1-5}$ alkyl;

(c) $C_2$ to $C_{15}$ straight or branched chain alkyl optionally substituted with hydroxy or alkoxy; and (d) —C(O)—$C_{6-12}$ arylene-C(O)— wherein said arylene is optionally substituted with hydroxy, halogen, nitro or amino;

a and b are independently 0, 1, 2, 3 or 4;

d, d', d'', e, e' and e'' are independently an integer from 1 to 4;

$X^1$, $X^2$, $Y^1$ and $Y^2$ are independently selected from the group consisting of a null, oxygen, NH and N(C(O)$C_{1-4}$ alkyl), and N($C_{1-4}$ alkyl)$_2$;

$W^1$ and $W^2$ are independently selected from the group consisting of carbonyl, methylene, sulfone and sulfoxide;

$R^2$ and $R^5$ are independently selected from the group consisting of:

(a) $C_2$ to $C_{20}$ straight chain or branched chain alkyl which is optionally substituted with oxo, hydroxy or alkoxy, (b) $C_2$ to $C_{20}$ straight chain or branched chain alkenyl or dialkenyl which is optionally substituted with oxo, hydroxy or alkoxy;

(c) $C_2$ to $C_{20}$ straight chain or branched chain alkoxy which is optionally substituted with oxo, hydroxy or alkoxy;

(d) —NH—$C_2$ to $C_{20}$ straight chain or branched chain alkyl, wherein said alkyl group is optionally substituted with oxo, hydroxy or alkoxy; and (e)

$$\begin{array}{c}
O \\
\parallel \\
Z\text{---}C\text{---}M \\
| \\
M
\end{array}$$

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;

$R^3$ and $R^6$ are independently selected from the group consisting of $C_2$ to $C_{20}$ straight chain or branched chain alkyl or alkenyl optionally substituted with fluoro or oxo;

$R^4$ and $R^7$ are independently selected from the group consisting of C(O)$C_2$ to $C_{20}$ straight chain or branched chain alkyl or alkenyl; $C_2$ to $C_{20}$ straight chain or branched chain alkyl; $C_2$ to $C_{20}$ straight chain or branched chain alkoxy; $C_2$ to $C_{20}$ straight chain or branched chain alkenyl; wherein said alkyl, alkenyl or alkoxy groups can be independently and optionally substituted with hydroxy, fluoro or $C_1$ to $C_5$ alkoxy;

$G^1$, $G^2$, $G^3$ and $G^4$ are independently selected from the group consisting of oxygen, methylene, amino, thiol, —NHC(O)—, and —N(C(O)$C_{1-4}$ alkyl)—;

or $G^2R^4$ or $G^4R^7$ may together be a hydrogen atom or hydroxyl;

or a pharmaceutically acceptable salt thereof.

11. The formulation of claim 8, wherein said adjuvant and antigen are covalently bonded through an amino, carbonyl, hydroxyl, or phosphate moiety of said adjuvant.

12. The formulation of claim 8, wherein $R^1$ is a C(O) or C(O)—$C_{3-14}$ alkyl-C(O), and wherein said adjuvant and antigen are covalently bonded to a carbonyl moiety of said C, carbonyl of said C(O) or C(O)—$C_{3-14}$ alkyl-C(O).

13. A method for stimulating an immune response to an antigen, comprising administering an effective amount of an antigen and an effective amount for stimulating an immune response to said antigen of an adjuvant compound of the formula I $$\begin{array}{c}
X^1\text{---}R^1\text{---}Y^1 \\
(CH_2)_a \qquad (CH_2)_b \\
O \qquad O \\
HO\text{---}P\text{=}O \qquad HO\text{---}P\text{=}O \\
O \qquad O \\
(CH_2)_d \qquad (CH_2)_e \\
X^2 \qquad Y^2 \\
W^1 \quad (CH_2)_{d'} \qquad (CH_2)_{e'} \quad W^2 \\
R^2 \quad G^1 \qquad G^3 \quad R^5 \\
(CH_2)_{d''} \qquad (CH_2)_{e''} \\
G^2 \qquad G^4 \\
R^4 \quad R^3 \qquad R^7 \quad R^6
\end{array}$$

wherein:

$R^1$ is selected from the group consisting of (a) C(O);

UNITED STATES PATENT AND TRADEMARK OFFICE
CERTIFICATE OF CORRECTION

PATENT NO.   : 6,290,973 B1
DATED        : September 18, 2001
INVENTOR(S)  : Hawkins et al.

Page 1 of 1

It is certified that error appears in the above-identified patent and that said Letters Patent is hereby corrected as shown below:

<u>Column 211,</u>
Line 40, "$C_2$ to $C_1 5$ straight . . .", "$C_1 5$" should be changed to -- $C_{15}$ --.

<u>Column 212,</u>
Line 39, "moiety of said C, carbonyl", "C" should be changed to -- $C_1$ --.

Signed and Sealed this

Twenty-eighth Day of May, 2002

Attest:

JAMES E. ROGAN
*Attesting Officer*   *Director of the United States Patent and Trademark Office*